US008134000B2

(12) United States Patent
Venkataramani

(10) Patent No.: US 8,134,000 B2
(45) Date of Patent: Mar. 13, 2012

(54) IMIDAZOLYL PYRIMIDINE INHIBITOR COMPOUNDS

(75) Inventor: Chandrasekar Venkataramani, Redwood City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 337 days.

(21) Appl. No.: 12/502,870

(22) Filed: Jul. 14, 2009

(65) Prior Publication Data
US 2010/0009990 A1 Jan. 14, 2010

Related U.S. Application Data

(60) Provisional application No. 61/080,426, filed on Jul. 14, 2008.

(51) Int. Cl.
C07D 401/00 (2006.01)
(52) U.S. Cl. ........ 544/331; 544/179; 544/180; 544/185; 544/215; 546/268.4; 514/183; 514/242; 514/245; 514/252.05; 514/336
(58) Field of Classification Search .................. 544/179, 544/185, 215, 180, 331; 546/268.4
See application file for complete search history.

(56) References Cited

U.S. PATENT DOCUMENTS

| | | | | |
|---|---|---|---|---|
| 5,760,246 | A | 6/1998 | Biller et al. | 548/309.7 |
| 6,403,588 | B1 | 6/2002 | Hayakawa et al. | 514/249 |
| 6,855,719 | B1 * | 2/2005 | Thomas et al. | 514/269 |
| 7,253,204 | B2 | 8/2007 | Delorme et al. | 514/422 |
| 2002/0168761 | A1 | 11/2002 | Gour et al. | 435/325 |
| 2004/0006011 | A1 | 1/2004 | Gour et al. | 514/9 |
| 2005/0054850 | A1 | 3/2005 | Wu et al. | 544/238 |
| 2005/0187266 | A1 | 8/2005 | Su | 514/359 |
| 2005/0234066 | A1 | 10/2005 | Bailey et al. | 514/252.03 |
| 2005/0288282 | A1 | 12/2005 | Delorme et al. | 514/228.2 |
| 2006/0293320 | A1 | 12/2006 | Schmitz et al. | 514/233.2 |
| 2007/0093492 | A1 | 4/2007 | Jiaang et al. | 514/249 |
| 2007/0213330 | A1 | 9/2007 | Delorme et al. | 514/235.5 |
| 2009/0005374 | A1 | 1/2009 | Melvin et al. | 514/233 |
| 2009/0076021 | A1 | 3/2009 | Plato | 514/252 |
| 2010/0009990 | A1 | 1/2010 | Venkataramani | 514/233.2 |
| 2010/0022543 | A1 | 1/2010 | Melvin et al. | 514/236.8 |
| 2010/0029638 | A1 | 2/2010 | Melvin et al. | 514/233.2 |
| 2010/0310500 | A1 | 12/2010 | Graupe et al. | |
| 2010/0311794 | A1 | 12/2010 | Venkataramani | |

FOREIGN PATENT DOCUMENTS

| | | | | |
|---|---|---|---|---|
| CA | 2644933 | | 9/2007 | 184/46 |
| EP | 0847992 | A1 | 6/1998 | |
| EP | 1 277 754 | | 1/2003 | |
| JP | 2003-313126 | | 11/2003 | |
| JP | 2004-002826 | | 1/2004 | |
| JP | 2007-001885 | | 1/2007 | |
| WO | WO 97/26240 | | 7/1997 | |
| WO | WO-00/18733 | A1 | 4/2000 | |
| WO | WO 01/14375 | | 3/2001 | |
| WO | WO 01/19788 | | 3/2001 | |
| WO | WO-01/53331 | A2 | 7/2001 | |
| WO | WO 01/56989 | | 8/2001 | |
| WO | WO 01/83481 | | 8/2001 | |
| WO | WO 02/00651 | | 1/2002 | |
| WO | WO 02/26712 | | 4/2002 | |
| WO | WO 02/34748 | | 5/2002 | |
| WO | WO 02/46170 | | 6/2002 | |
| WO | WO 02/065979 | | 8/2002 | |
| WO | WO 02/066480 | | 8/2002 | |
| WO | WO 02/066481 | | 8/2002 | |
| WO | WO 03/000682 | | 1/2003 | |
| WO | WO 03/000689 | | 1/2003 | |
| WO | WO 03/002524 | | 1/2003 | |
| WO | WO 03/031446 | | 4/2003 | |
| WO | WO 03/041649 | | 5/2003 | |
| WO | WO 03/084948 | | 10/2003 | |
| WO | WO 03/084997 | | 10/2003 | |
| WO | WO 03/099221 | | 12/2003 | |
| WO | WO 03/099817 | | 12/2003 | |
| WO | WO-03/103151 | A1 | 12/2003 | |
| WO | WO 2004/021989 | | 3/2004 | |
| WO | WO 2004/035525 | | 4/2004 | |
| WO | WO 2004/039325 | | 5/2004 | |
| WO | WO 2004/041191 | | 5/2004 | |
| WO | WO 2004/048343 | | 6/2004 | |
| WO | WO 2006/058007 | | 6/2004 | |
| WO | WO-2004/060318 | A2 | 7/2004 | |
| WO | WO 2004/069133 | | 8/2004 | |
| WO | WO 2004/069803 | | 8/2004 | |
| WO | WO 2004/076452 | | 9/2004 | |
| WO | WO 2004/080390 | | 9/2004 | |
| WO | WO 2004/084901 | | 10/2004 | |
| WO | WO 2004/092115 | | 10/2004 | |

(Continued)

OTHER PUBLICATIONS

U.S. Appl. No. 61/185,126, filed Jun. 8, 2009, Gaupe et al.

(Continued)

Primary Examiner — James O Wilson
Assistant Examiner — Alexander R Pagano
(74) Attorney, Agent, or Firm — J. Elin Hartrum

(57) ABSTRACT

A compound of general Formula (I) having histone deacetylase (HDAC) and/or Cyclin-dependent kinase (CDK) inhibitory activity, a pharmaceutical composition comprising the compound, and a method useful to treat diseases using the compound.

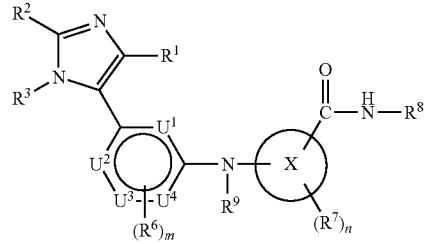

Formula (I)

13 Claims, No Drawings

FOREIGN PATENT DOCUMENTS

| | | |
|---|---|---|
| WO | WO 2004/092145 | 10/2004 |
| WO | WO 2004/110350 | 12/2004 |
| WO | WO 2005/006945 | 1/2005 |
| WO | WO 2005/030140 | 4/2005 |
| WO | WO-2005/030705 A1 | 4/2005 |
| WO | WO 2005/046594 | 5/2005 |
| WO | WO-2005/054850 A2 | 6/2005 |
| WO | WO 2005/060571 | 7/2005 |
| WO | WO-2005/070180 A2 | 8/2005 |
| WO | WO 2005/077368 | 8/2005 |
| WO | WO 2005/077373 | 8/2005 |
| WO | WO 2005/082871 | 9/2005 |
| WO | WO 2005/092899 | 10/2005 |
| WO | WO 2005/102318 | 11/2005 |
| WO | WO 2005/102325 | 11/2005 |
| WO | WO-2005/102326 A2 | 11/2005 |
| WO | WO 2005/102346 | 11/2005 |
| WO | WO 2005/102455 | 11/2005 |
| WO | WO 2005/103022 | 11/2005 |
| WO | WO 2005/112920 | 12/2005 |
| WO | WO 2005/115304 | 12/2005 |
| WO | WO 2005/115385 | 12/2005 |
| WO | WO 2006/010750 | 2/2006 |
| WO | WO 2006/038001 | 4/2006 |
| WO | WO 2006/044509 | 4/2006 |
| WO | WO 2006/058905 | 6/2006 |
| WO | WO-2006064251 A1 | 6/2006 |
| WO | WO 2006/070943 | 7/2006 |
| WO | WO 2006/077401 | 7/2006 |
| WO | WO 2006/108059 | 10/2006 |
| WO | WO 2006/104983 | 11/2006 |
| WO | WO 2006/122011 | 11/2006 |
| WO | WO 2007/008664 | 1/2007 |
| WO | WO 2007/026251 | 3/2007 |
| WO | WO 2007/030362 | 3/2007 |
| WO | WO 2007/036732 | 4/2007 |
| WO | WO 2007/037187 | 4/2007 |
| WO | WO-2007040440 A1 | 4/2007 |
| WO | WO 2007/055941 | 5/2007 |
| WO | WO 2007/076034 | 7/2007 |
| WO | WO 2007/076035 | 7/2007 |
| WO | WO 2007/079185 | 7/2007 |
| WO | WO 2007/087129 | 8/2007 |
| WO | WO 2007/087717 | 8/2007 |
| WO | WO-2007/093492 A1 | 8/2007 |
| WO | WO 2007/095124 | 8/2007 |
| WO | WO 2007/106192 | 8/2007 |
| WO | WO 2007/100795 | 9/2007 |
| WO | WO-2007/127137 A2 | 11/2007 |
| WO | WO 2007/135036 | 11/2007 |
| WO | WO 2008/033743 | 3/2008 |
| WO | WO 2009/002534 | 12/2008 |
| WO | WO 2009/079391 | 6/2009 |
| WO | WO 2010/009139 | 1/2010 |
| WO | WO-2010/009139 A2 | 1/2010 |
| WO | WO 2010/009155 | 1/2010 |
| WO | WO-2010/009155 A2 | 1/2010 |
| WO | WO 2010/009166 | 1/2010 |
| WO | WO-2010/009166 A1 | 1/2010 |
| WO | WO 2010/014611 | 2/2010 |
| WO | WO-2010/014611 A1 | 2/2010 |

OTHER PUBLICATIONS

U.S. Appl. No. 61/185,134, filed Jun. 8, 2009, Gaupe et al.

Acharya et al., "Rational Development of Histone Deacetylase Inhibitors as Anticancer Agents: A Review", *Molecular Pharmacology*, 2005, 68:917-932.

Alam et al., "Synthesis and SAR of aminopyridines as novel c-Jun N-terminal kinase (JNK) inhibitors", *Bioorg. Med. Chem. Lett.*, 2007, 17:3463-3467.

Buggy et al,. "CRA-024781: a novel synthetic inhibitor of histone deacetylase enzymes with antitumor activity in vitro and in vivo", *Mol. Cancer Ther.*, 2006, 5:1309-1317.

Bush & McKinsey, "Targeting Histone Deacetylases for Heart Failure," *Expert Opin. Ther. Targets*, 2009, 13(7): 767-784.

Feng et al., "Synthesis and SAR of 2-(4-fluorophenyl)-3-pyrimidin-4-ylimidazo[1,2-α]pyridine derivatives as anticoccidial agents", *Bioorg. Med. Chem. Lett.*, 2006, 5978-5981.

Gudmundsson et al., "Imidazo[1,2-α]pyridines with potent activity against herpesviruses", *Bioorg. Med. Chem. Lett.*, 2007, 17:2735-2739.

Hayakawa et al., "Synthesis and biological evaluation of imidazo[1,2-α]pyridine derivatives as novel PI3 kinase p110α inhibitors", *Bioorg. Med. Chem. Lett.*, 2007, 15:403-412.

Liang et al., "Synthesis and SAR studies of potent imidazopyridine anticoccidial agents", *Bioorg. Med. Chem. Lett.*, 2007, 17:3558-3561.

Mahboobi et al., "2-Aroylindoles and ω-Aroylbenzofurans with N-Hydroxyacrylamide Substructures as a Novel Series of Rationally Designed Histone Deacetylase Inhibitors," *J. Chem. Soc.*, 2007, 50(18): 4405-4418.

Marcou et al., "Optimizing Fragment and Scaffold Docking by Use of Molecular Interaction Fingerprints", *J. Chem. Inf. Model*, 2007, 47(1):195-207.

Moradei et al., "Histone Deacetylase Inhibitors: Latest Developments, Trends, and Prospects", *Current Med. Chem.—Anti-Cancer Agents*, 2005, 529-560.

Paris et al., "Histone Deacetylase Inhibitors: From Bench to Clinic", *J. Med. Chem*, 2008, 51(6):1505-1529.

Park et al., "A Simple and Efficient Docking Method to the Cyclin-Dependent Kinase 2", *Bull. Korean Chem. Soc.*, 2007, 28(2):211-219.

Price et al., "Histone deacetylase inhibitors: an analysis of recent patenting activity", *Expert Opinion, Ther. Patents*, 2007, 745-765.

Rosato et al., *Cancer Research*, 2003, 63:3637-3645.

Vadivelan et al., "Virtual Screening Studies to Design Potent CDK2-Cyclin A Inhibitors", *J. Chem. Inf. Model*, 2007, 47(4): 1526-1535.

Vigushin et al., "Targeted Histone Deacetylase Inhibition for Cancer Therapy", *Current Cancer Drug Targets*, 2004, 4(2):205-218.

International Search Report, dated Oct. 1, 2008, issued in PCT/US2008/007963.

International Search Report, dated Mar. 23, 2009, issued in PCT/US2008/086643.

International Search Report, dated Oct. 2, 2009, issued in PCT/US2009/051964.

International Search Report, dated Oct. 12, 2009, issued in PCT/US2009/050558.

International Search Report, dated Nov. 11, 2009, issued in PCT/US2009/050577.

International Search Report and Written Opinion, dated Nov. 18, 2009, issued in PCT/US2009/050595.

Office Action for Election/Restrictions, dated Jan. 22, 2010, issued in U.S. Appl. No. 12/146,894.

International Search Report for PCT/US2009/050558, International Filing Date Jul. 14, 2009, mailed May 20, 2010.

Lee, M. et al. (2003) "Molecular Targets for Cell Cycle Inhibition and Cancer Therapy" *Expert Opinion on Therapeutic Patents* 13(3):329-346.

Price, S. et al. (2007) "Histone Deacetylase Inhibitors: An Analysis of Recent Patenting Activity" *Expert Opinion on Therapeutic Patents* 17(7):745-765.

Arbiser, J.L. (2007) "Why Targeted Therapy Hasn't Worked in Advanced Cancer", *The Journal of Clinical Investigation*, vol. 17, No. 10 pp. 2762-2765.

Fischer, B. et al. (2007) "Targeting Receptor Tyrosine Kinase Signalling in Small Cell Lung Cancer (SCLC): What Have We Learned So Far?", *Cancer Treatment Reviews*, vol. 33, pp. 391-406.

International Search Report for PCT/US2010/037647, International Filing Date Jun. 7, 2010, mailed Nov. 9, 2010.

Madhusudan, S. et al. (2004) "Tyrosine Kinase Inhibitors in Cancer Therapy", *Clinincal Biochemistry*, vol. 37, 00.618-635.

U.S. Office Action for U.S. Appl. No. 12/747,159, mailed Dec. 10, 2010.

U.S. Appl. No. 12/943,799, filed Nov. 10, 2010.

\* cited by examiner

IMIDAZOLYL PYRIMIDINE INHIBITOR COMPOUNDS

CROSS REFERENCE TO RELATED APPLICATION

This application claims the benefit of U.S. provisional application Ser. No. 61/080,426 filed Jul. 14, 2008. The disclosure of the application is hereby incorporated by reference.

FIELD

The present invention generally relates to a compound having enzyme inhibitory activity, pharmaceutical compositions comprising the compound, and methods useful for treating diseases.

BACKGROUND

Histones are protein components making up chromatin in association with DNA. Histones are subject to covalent modifications of various enzymes such as, for example, histone deacetylase (HDAC), histone methyltransferase (HMT) and histone acetyltransferase (HAT). Covalent modifications of core histones influence protein-protein interaction and protein access to DNA.

HDACs catalyze deacetylation of lysine residues on histones and other proteins. It is known that low levels of histone-acetylation are associated with repression of gene expression. Therefore, abnormal HDAC activities could destroy the delicate balance in cell regulation. The HDACs belong to four structurally and functionally different phylogenetic classes: class I (HDAC-1, -2,-3, and -8) compounds are closely related to yeast RPD3; class IIa (HDAC-4,-5, 7, and -9) and class IIb (HDAC-6 and -10) share domains with yeast HDAC-1; class IV, recently described (comprising HDAC-11), exhibits properties of both class I and class II HDACs. All the above HDACs are zinc dependent proteases. Class III HDACs have been identified on the basis of sequence similarity with Sir2, a yeast transcription repressor, and require the cofactor NAD+ for their deacetylase function. See, for example, Marielle Paris et al., *Histone Deacetylase Inhibitors: From Bench to Clinic*, JOURNAL OF MEDICINAL CHEMISTRY 51(11): 3330-3330 (2008).

It has been reported that HDAC activities play an important role in a variety of human disease states. Accordingly, an HDAC inhibitor can provide therapeutic benefits to a broad range of patients. Due to the therapeutic significance, various types of HDAC inhibitors have been developed to date. See, for example, Moradei et al., *Histone Deacetylase Inhibitors: Latest Developments, Trends, and Prospects*, CURR. MED. CHEM.: ANTI-CANCER AGENTS 5(5):529-560 (2005).

Cyclin-dependent kinases (CDKs) are protein kinase enzymes controlling transcription and mRNA processing for the regulation of the cell cycle. CDKs belong to a group of serine/threonine kinases phosphorylating proteins on serine and threonine amino acid residues. A CDK is activated by association with a cyclin forming a cyclin-dependent kinase complex. The CDK family has been identified to include at least 9 members, i.e., CDK1, CDK2, CDK3, CDK4, CDK5, CDK6, CDK7, CDK8 and CDK9, and CDKs pair with a specific cyclin in the various phases of the cell cycle for the progression. CDKs are considered a target for anti-cancer medication since the enzymes are major control switches for the cell cycle.

WO 2005/092899 mentions a series of compounds useful for inhibiting HDAC enzymatic activity where the compounds are amino or hydroxyl substituted aniline derivatives attached to various cyclic groups.

There is a continued need to develop new inhibitors to provide appropriate therapy for a variety of disease conditions implicated in HDAC and/or CDK activity.

SUMMARY

In various embodiments, a compound having HDAC inhibitory activity, a composition comprising the compound and a method useful to treat diseases arising from abnormal cell proliferation or differentiation are provided.

The compound is of Formula (I) or a pharmaceutically acceptable salt thereof:

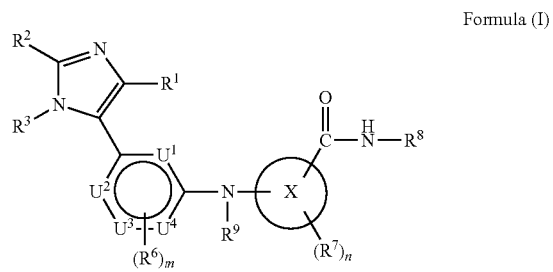

Formula (I)

where $R^1$, $R^2$ and $R^3$ can each be hydrogen, and when they are non-hydrogen they represent substitutable groups that provide the compounds of Formula (I) with HDAC and/or CDK binding activity. The variables m and n can be zero, and when they are non-zero, the respective $R^6$ and $R^7$ groups are substituents that provide for HDAC and/or CDK inhibitory activity in the compounds. In Formula (I), the substituents $R^1$, $R^2$ and $R^3$ are attached to an imidazole ring; $R^6$ is attached to a 6-membered nitrogen containing heteroaryl; and $R^7$ is attached to an aryl group. The $R^9$ group is hydrogen or a substitutable group providing for HDAC and/or CDK inhibitory activity in the compounds. The group

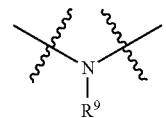

provides a "linker" between the 6-membered heteroaryl and the ring X.

In the 6-membered nitrogen heteroaryl, at least one of $U^1$, $U^2$, $U^3$, and $U^4$ is a ring nitrogen. In some embodiments, at least $U^4$ is a ring nitrogen. In some embodiments, both $U^1$ and $U^4$ are ring nitrogens. In some embodiments, only $U^4$ is a ring nitrogen. In some embodiments, only $U^1$ and $U^4$ are ring nitrogens.

In various embodiments, the substituents are further defined as follows:

$R^1$, $R^2$ and $R^3$ are independently selected from the group consisting of H, halo, nitro, cyano, hydroxy, hydroxy ($C_{1-10}$ alkyl), amino($C_{1-10}$ alkyl), haloalkyl, haloalkoxy, amino, azido, carboxyl, carbamoyl, mercapto, sulphamoyl, $C_{1-10}$ alkyl, $C_{2-10}$ alkenyl, $C_{2-10}$ alkynyl, $C_{1-10}$ alkoxy, hydroxy($C_{1-10}$ alkoxy)($C_{1-10}$ alkoxy), ($C_{1-10}$ alkoxy)($C_{1-10}$ alkoxy), ($C_{1-10}$ alkoxy)($C_{1-10}$ alkyl), $C_{1-10}$ alkanoyl, $C_{1-10}$ alkanoyloxy, N—($C_{1-10}$ alkyl)amino, N,N—($C_{1-10}$ alkyl)$_2$amino, $C_{1-10}$ alkanoylamino, N—($C_{1-10}$ alkyl)carbamoyl, N,N—($C_{1-10}$ alkyl)$_2$carbamoyl, $C_{1-10}$ alkyl-S(O)$_a$ wherein a is 0, 1 or 2, $C_{1-10}$ alkoxycarbonyl, NH$_2$—S(O)$_2$NH—, NH$_2$—CO—NH—, N—($C_{1-10}$ alkyl)sulphamoyl, N,N—($C_{1-10}$ alkyl)$_2$sulphamoyl, aryl, arylalkyl, aryloxy, arylthio, cycloalkyl, cycloalkylalkyl, cycloalkyloxy, heterocyclyl, heterocyclylalkyl, heterocyclyl(C=O)—, heterocyclyloxy and heterocyclylthio, wherein each $R^1$, $R^2$ and $R^3$ is optionally substituted by one or more A where such an optional substitution is chemically feasible;

$U^1$, $U^2$, $U^3$ and $U^4$ are independently selected from —N—, —CH—, and —$CR^6$—, with the proviso that at least one of $U^1$, $U^2$, $U^3$ and $U^4$ is —N—; in one embodiment, at least $U^4$ is —N—;

m is the number of non-hydrogen substituents $R^6$ on the N-containing 6-membered nitrogen containing heteroaryl and can be 0, 1, 2, or 3;

each $R^6$ is independently selected from hydroxy, halo, nitro, cyano, trifluoromethyl, trifluoromethoxy, amino, carboxyl, carbamoyl, sulphamoyl, $C_{1-10}$ alkyl, $C_{2-10}$ alkenyl, $C_{2-10}$ alkynyl, $C_{1-10}$ alkoxy, $C_{1-10}$ alkanoyl, N—($C_{1-10}$ alkyl)amino, N,N—($C_{1-10}$ alkyl)$_2$ amino, $C_{1-10}$ alkanoylamino, N—($C_{1-10}$ alkyl)carbamoyl, N,N—($C_{1-10}$ alkyl)$_2$ carbamoyl, $C_{1-10}$ alkyl-S(O)$_a$ wherein a is 0, 1 or 2, NH$_2$—S(O)$_2$NH—, N—($C_{1-10}$ alkyl)sulphamoyl or N,N—($C_{1-10}$ alkyl)$_2$sulphamoyl, wherein $R^6$ is optionally substituted by one or more B where such an optional substitution is chemically feasible;

X is phenyl, 5-membered heteroaryl, or 6-membered heteroaryl, wherein the heteroaryl contains one or more heteroatoms selected from N, S and O;

n is the number of non-hydrogen substituents $R^7$ on the ring X and can be 0, 1, 2, 3, or 4, wherein the maximum value of n depends on the nature of the ring X;

$R^7$ represents one or more optional non-hydrogen substituents on ring X, wherein when present, each $R^7$ is independently selected from hydroxy, halo, nitro, cyano, trifluoromethyl, trifluoromethoxy, amino, carboxyl, carbamoyl, sulphamoyl, $C_{1-10}$ alkyl, $C_{2-10}$ alkenyl, $C_{2-10}$ alkynyl, $C_{1-10}$ alkoxy, $C_{1-10}$ alkanoyl, N—($C_{1-10}$ alkyl)amino, N,N—($C_{1-10}$ alkyl)$_2$ amino, $C_{1-10}$ alkanoylamino, N—($C_{1-10}$ alkyl)carbamoyl, N,N—($C_{1-10}$ alkyl)$_2$ carbamoyl, $C_{1-10}$ alkyl-S(O)$_a$ wherein a is 0, 1 or 2, NH$_2$—S(O)$_2$NH—, N—($C_{1-10}$ alkyl)sulphamoyl, N,N—($C_{1-10}$ alkyl)$_2$sulphamoyl, cycloalkyl, heterocyclyl, and aryl;

$R^8$ is hydroxy, aryl or heteroaryl, wherein aryl or heteroaryl is substituted with —NH$_2$ or —OH and aryl or heteroaryl is optionally further substituted with one or more groups selected from amino, halo, alkyl, alkenyl, alkynyl, haloalkyl, cycloalkyl, heterocyclyl, aryl, haloaryl, haloheterocyclyl, wherein alkyl, alkenyl, or alkynyl is optionally further substituted with one or more groups selected from halo, hydroxy, alkyl, haloalkyl and cycloalkyl;

$R^9$ is H, alkyl, haloalkyl, aminoalkyl, cycloalkyl, aryl, or heterocyclyl, wherein $R^9$ is optionally substituted by one or more D where such an optional substitution is chemically feasible; and A, B and D are independently selected from halo, nitro, cyano, hydroxy, hydroxyalkyl, haloalkyl, haloalkoxy, amino, azido, carboxyl, carbamoyl, mercapto, oxo, sulphamoyl, $C_{1-10}$ alkyl, $C_{2-10}$ alkenyl, $C_{2-10}$ alkynyl, $C_{1-10}$ alkoxy, $C_{1-10}$ alkanoyl, $C_{1-10}$ alkanoyloxy, N—($C_{1-10}$ alkyl)amino, N,N—($C_{1-10}$ alkyl)$_2$amino, $C_{1-10}$ alkanoylamino, N—($C_{1-10}$ alkyl)carbamoyl, N,N—($C_{1-10}$ alkyl)$_2$carbamoyl, $C_{1-10}$ alkyl-S(O)$_a$ wherein a is 0, 1 or 2, $C_{1-10}$ alkoxycarbonyl, N—($C_{1-10}$ alkyl)sulphamoyl, N,N—($C_{1-10}$ alkyl)$_2$sulphamoyl, H$_2$NS(O)$_2$NH—, N—($C_{1-10}$ alkyl)NHS(O)$_2$NH—, N,N—($C_{1-10}$ alkyl)$_2$NS(O)$_2$NH—, aryl, aryloxy, arylthio, cycloalkyl, cycloalkyloxy, heterocyclyl, heterocyclyl(C=O)—, heterocyclyloxy and heterocyclylthio.

In various embodiments, the substitution with —NH$_2$ or —OH on aryl or heteroaryl of $R^8$ is adjacent to the attachment of the X—C(O)NH— group to the aryl or heteroaryl.

In an embodiment, $R^8$ is hydroxy and the compounds are characterized as hydroxamates. In another embodiment, $R^8$ is substituted aryl or heteroaryl and the compounds are characterized as arylamides.

In an embodiment, $R^9$ is H.

In an embodiment, X is phenyl. In various embodiments, the N—$R^9$ linker and —C(O)NH—$R^8$ groups are disposed on the phenyl in a 1,4-configuration, where the N—$R^9$ linker is considered as the 1-position.

In an embodiment, X is thiophene. In various embodiments, the N—$R^9$ linker and —C(O)NH—$R^8$ groups are disposed on the thiophene in a 2,5-configuration, where the linker is considered as the 2-position (with the S atom of the thiophene ring taken as the 1-position).

In an embodiment, X is pyridine. In various embodiments, the N—$R^9$ linker and —C(O)NH—$R^8$ groups are disposed on the pyridine in a 2,5-configuration, where the linker is considered as the 2-position, or in a 3,6-configuration, where the linker is considered as the 3-position (in all cases, the N atom of the pyridine ring is taken as the 1-position).

In an embodiment, X is thiazole. In various embodiments, the N—$R^9$ linker and —C(O)NH—$R^8$ groups are disposed on the thiazole in a 2,4- or 2,5-configuration, where the linker is considered as the 2-position (with the S atom of the thiazole ring taken as the 1-position).

In an embodiment, the 6-membered nitrogen containing heteroaryl is pyrimidine, with $U^1$ and $U^4$ being ring nitrogens. In various embodiments, the pyrimidine is substituted with an imidazole ring which itself is optionally substituted with $R^1$, $Q^1$, and $Q^2$.

In the Formulae herein, non-limiting examples of A and B include halo, alkyl, nitro, cyano, hydroxy, oxo, cycloalkyl, trifluoromethoxy, trifluoromethyl, trifluoroethyl, amino, carboxyl, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl, N-methyl-N-ethylsulphamoyl, aryl, heterocyclyl, and cycloalkyl.

In the definitions herein of $R^1$, $R^2$, $R^3$, $R^6$, $R^7$, A and B, the carbon ranges for the groups alkyl, alkenyl, alkynyl, alkoxy, alkanoyl, alkanoyloxy, alkanoylamino, and the like include all ranges encompassed in the recited ranges $C_{1-10}$ and $C_{2-10}$. For example, in non-limiting fashion $C_{1-10}$ includes a disclosure of $C_{1-6}$ and $C_{1-3}$, and $C_{2-10}$ includes a disclosure of $C_{2-6}$ and $C_{2-3}$. In various embodiments, $C_{1-10}$ carbon-chain containing groups such as $C_{1-10}$ alkyl, $C_{2-10}$ alkenyl, $C_{2-10}$ alkynyl and so forth include the respective $C_{1-6}$ and $C_{1-3}$ shorter carbon-chains such as $C_{1-6}$ alkyl, $C_{1-3}$ alkyl, $C_{2-6}$ alkenyl, $C_{2-3}$ alkenyl, $C_{2-6}$ alkynyl and $C_{2-3}$ alkynyl.

In the Tables that follow, examples are given with n=0 or n=1. When n=0, the entry in the $R^7$ column reads H (hydrogen atom) to indicate that all substituents are hydrogen. When n=1, the entry in the $R^7$ column gives the identity and position of the single non-hydrogen substituent.

Pharmaceutical compositions comprise an HDAC and/or CDK-inhibitory effective amount of one or more compounds described herein and a pharmaceutically-acceptable carrier.

Methods of inhibiting or treating diseases arising from abnormal cell proliferation and differentiation comprise administering to a subject a therapeutically effective amount of one or more compounds described herein. Other methods involve co-therapies by administering one or more of the compounds together with other anti-cancer agents.

DETAILED DESCRIPTION

The following description is merely exemplary in nature and is not intended to limit the present disclosure, application, or uses.

Definitions

"Alkenyl" refers to a straight or branched hydrocarbyl group with at least one site of unsaturation, i.e. a carbon-carbon, $sp^2$ double bond. In an embodiment, alkenyl has from 2 to 12 carbon atoms. In some embodiments, alkenyl is a $C_2$-$C_{10}$ alkenyl group or a $C_2$-$C_6$ alkenyl group. Examples of alkenyl group include, but are not limited to, ethylene or vinyl (—CH═CH$_2$), allyl (—CH$_2$CH═CH$_2$), cyclopentenyl (—C$_5$H$_7$), and 5-hexenyl (—CH$_2$CH$_2$CH$_2$CH$_2$CH═CH$_2$).

"Alkanoyl" is the group RC(O)—; "alkanoyloxy" is RC(O)O—; and "alkanoylamino" is RC(O)NR'—; where R is an alkyl group as defined herein, and R' is hydrogen or alkyl. In various embodiments, R is a $C_1$-$C_{10}$ alkyl group or a $C_1$-$C_6$ alkyl group.

"Alkoxy" is RO— where R is alkyl. Non-limiting examples of alkoxy groups include methoxy, ethoxy and propoxy.

"Alkoxyalkyl" refers to an alkyl moiety substituted with an alkoxy group. Examples of alkoxyalkyl groups include methoxymethyl, methoxyethyl, methoxypropyl and ethoxyethyl.

"Alkoxycarbonyl" is ROC(O)—, where R is an alkyl group as defined herein. In various embodiments, R is a $C_1$-$C_{10}$ alkyl group or a $C_1$-$C_6$ alkyl group.

"Alkyl" refers to a straight or branched chain saturated hydrocarbyl group. In an embodiment, alkyl has from 1 to 12 carbon atoms. In some embodiments, alkyl is a $C_1$-$C_{10}$ alkyl group or a $C_1$-$C_6$ alkyl group. Examples of alkyl groups include, but are not limited to, methyl, ethyl, propyl, isopropyl, butyl, isobutyl, t-butyl, pentyl, hexyl, heptyl, octyl, nonyl and decyl.

"Alkylamino" refers to an amino group substituted with one or more alkyl groups. "N-(alkyl)amino" is RNH— and "N,N-(alkyl)$_2$amino" is R$_2$N—, where the R groups are alkyl as defined herein and are the same or different. In various embodiments, R is a $C_1$-$C_{10}$ alkyl group or a $C_1$-$C_6$ alkyl group. Examples of alkylamino groups include methylamino, ethylamino, propylamino, butylamino, dimethylamino, diethylamino, and methylethylamino.

"Alkylaminoalkyl" refers to an alkyl moiety substituted with an alkylamino group, wherein alkylamino is as defined herein. Examples of alkylaminoakyl groups include methylaminomethyl and ethylaminomethyl.

"Alkynyl" refers to a straight or branched carbon-chain group with at least one site of unsaturation, i.e. a carbon-carbon, sp triple bond. In an embodiment, alkynyl has from 2 to 12 carbon atoms. In some embodiments, alkynyl is a $C_2$-$C_{10}$ alkynyl group or a $C_2$-$C_6$ alkynyl group. Examples of alkynyl groups include acetylenic (—C≡CH) and propargyl (—CH$_2$C≡CH).

"Aryl" refers to any monocyclic, bicyclic or tricyclic carbon ring system wherein at least one ring is aromatic. In various embodiments, aryl encompasses a ring system of up to 14 carbon atoms. Aryl includes a carbocyclic aromatic ring fused with a 5-or 6-membered cycloalkyl group. Examples of aryl groups include, but are not limited to, phenyl, naphthyl, tetrahydronaphthyl and indanyl.

"Aryloxy" is RO—, where R is aryl. "Arylthio" is RS—, where R is aryl.

"Carbamoyl" is the group NH$_2$—C(O)—; the nitrogen can be substituted with alkyl groups. N-(alkyl)carbamoyl is RNH—C(O)— and N,N-(alkyl)$_2$ carbamoyl is R$_2$N—C(O)—, where the R groups are alkyl as defined herein and are the same or different. In various embodiments, R is a $C_1$-$C_{10}$ alkyl group or a $C_1$-$C_6$ alkyl group.

"Cycloalkyl" is a hydrocarbyl group containing at least one saturated or partially unsaturated ring structure, and attached via a ring carbon. In various embodiments, it refers to a saturated or a partially unsaturated $C_3$-$C_{12}$ cyclic moiety, examples of which include cyclopropyl, cyclobutyl, cyclopentyl, cyclopentenyl, cyclohexyl, cyclohexenyl, cycloheptyl and cyclooctyl.

"Cycloalkyloxy" is RO—, where R is cycloalkyl.

"Cycloalkylalkyl" refers to an alkyl moiety substituted with a cycloalkyl group, wherein cycloalkyl is as defined herein. Examples of cycloalkylalkyl groups include cyclopropylmethyl, cyclobutylmethyl, cyclopentylethyl and cyclohexylmethyl.

"Dialkylamino" refers to an RR'N— group where R and R' are independently alkyl as defined herein. Examples of dialkylamino groups include, but are not limited to, dimethylamino, diethylamino, methylethylamino and methylpropylamino. In various embodiments, R and R' are independently a $C_1$-$C_{10}$ alkyl group or a $C_1$-$C_6$ alkyl group.

"Dialkylaminoalkyl" refers to an alkyl moiety substituted with a dialkylamino group, wherein dialkylamino is as defined herein. Examples of dialkylaminoalkyl groups include, but are not limited to, dimethylaminomethyl and diethylaminomethyl.

"Feasible" refers to a structure or process that is capable of being accomplished; one that is possible, suitable, or logical. When a structure or process is "chemically feasible", that structure or process is synthetically attainable, chemically stable to the typical ambient conditions and/or contributes to favorable biological properties such as efficacy, bioavailability and minimal toxicity for the intended use. Chemically feasible structures are bound by the rules of electron bonding, whereby bonds can only be formed between atoms that are capable of forming bonds with one another. Likewise, chemically feasible processes can only produce structures that are chemically feasible.

"Halo" refers to chloro (—Cl), bromo (—Br), fluoro (—F) or iodo (—I).

"Haloalkoxy" refers to an alkoxy group substituted with one or more halo groups. Examples of haloalkoxy groups include, but are not limited to, —OCF$_3$, —OCHF$_2$ and —OCH$_2$F.

"Haloalkoxyalkyl" refers to an alkyl moiety substituted with a haloalkoxy group, wherein haloalkoxy is as defined herein. Examples of haloalkoxyalkyl groups include trifluoromethoxymethyl, trifluoroethoxymethyl and trifluoromethoxyethyl.

"Haloalkyl" refers to an alkyl moiety substituted with one or more halo groups. Examples of haloalkyl groups include —CF$_3$ and —CHF$_2$.

"Heterocyclyloxy" is RO—, where R is heterocyclyl. "Heterocyclylthio" is RS—, where R is heterocyclyl.

"Heteroaryl" refers to a monocyclic, bicyclic or tricyclic ring having up to 7 atoms in each ring, wherein at least one ring is aromatic and contains from 1 to 4 heteroatoms in the ring selected from the group consisting of N, O and S. Non-limiting examples of heteroaryl include pyridyl, thienyl, furanyl, pyrimidyl, imidazolyl, imidazopyridyl, pyranyl, pyrazolyl, pyrzolopyridyl, thiazolyl, thiadiazolyl, isothiazolyl, oxazolyl, isoxazoyl, pyrrolyl, pyridazinyl, pyrazinyl, quinolinyl, isoquinolinyl, benzofuranyl, dibenzofuranyl, dibenzothiophenyl, benzothienyl, indolyl, benzothiazolyl, benzooxazolyl, benzimidazolyl, isoindolyl, benzotriazolyl, purinyl, thianaphthenyl and pyrazinyl. Attachment of heteroaryl can occur via an aromatic ring, or, if heteroaryl is bicyclic or tricyclic and one of the rings is not aromatic or contains no heteroatoms, through a non-aromatic ring or a ring containing no heteroatoms. "Heteroaryl" is also understood to include the N-oxide derivative of any nitrogen containing heteroaryl.

"Heteroaryloxy" is RO—, where R is heteroaryl.

"Heterocyclyl" includes the heteroaryls defined herein and refers to an unsaturated, saturated or partially unsaturated monocyclic, bicyclic or tricyclic group of 2 to 14 ring-carbon atoms and, in addition to ring-carbon atoms, 1 or more heteroatoms selected from P, N, O and S. In various embodiments the heterocyclic group is attached to another moiety through carbon or through a heteroatom, and is optionally substituted on carbon or a heteroatom. Examples of heterocyclyl include azetidinyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrahydrothiopyranyl, tetrahydroisoquinolinyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

"Hydroxyalkoxy" refers to an alkoxy group substituted with a hydroxyl group (—OH), wherein alkoxy is as defined herein. An example of hydroxyalkoxy is hydroxyethoxy.

"Hydroxyalkyl" refers to a linear or branched monovalent $C_1$-$C_{10}$ hydrocarbon group substituted with at least one hydroxy group. Examples of hydroxyalkyl groups include, but are not limited to, hydroxymethyl, hydroxyethyl, hydroxypropyl and hydroxybutyl.

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less.

"Sulphamoyl" is $NH_2$—$S(O)_2$—; "N-(alkyl)sulphamoyl" is $RNH$—$S(O)_2$—; and "N,N-(alkyl)$_2$ sulphamoyl" is $R_2N$—$S(O)_2$—, where the R groups are alkyl as defined herein and are the same or different. In various embodiments, R is a $C_1$-$C_{10}$ alkyl group or a $C_1$-$C_6$ alkyl group.

"Pharmaceutically-acceptable" means suitable for use in pharmaceutical preparations, generally considered as safe for such use, officially approved by a regulatory agency of a national or state government for such use, or being listed in the U.S. Pharmacopoeia or other generally recognized pharmacopoeia for use in animals, and more particularly in humans.

"Pharmaceutically-acceptable carrier" refers to a diluent, adjuvant, excipient, carrier, other ingredient, or combination of ingredients that is pharmaceutically-acceptable and with which a compound of the invention is administered.

"Pharmaceutically-acceptable salt" refers to a salt that may enhance desired pharmacological activity. Examples of pharmaceutically-acceptable salts include acid addition salts formed with inorganic or organic acids, metal salts and amine salts. Examples of acid addition salts formed with inorganic acids include salts with hydrochloric acid, hydrobromic acid, sulfuric acid, nitric acid and phosphoric acid. Examples of acid addition salts formed with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)-benzoic acid, cinnamic acid, mandelic acid, methanesulfonic acid, ethanesulfonic acid, 1,2-ethanedisulfonic acid, 2-hydroxyethane-sulfonic acid, benzenesulfonic acid, p-chlorobenzenesulfonic acid, 2-naphthalenesulfonic acid, p-toluenesulfonic acid, camphorsulfonic acid, 4-methyl-bicyclo[2.2.2]oct-2-ene1-carboxylic acid, gluco-heptonic acid, 4,4'-methylenebis(3-hydroxy-2-naphthoic) acid, 3-phenylpropionic acid, trimethyl-acetic acid, tertiary butylacetic acid, lauryl sulfuric acid, gluconic acid, glutamic acid, hydroxy-naphthoic acids, salicylic acid, stearic acid and muconic acid. Examples of metal salts include salts with sodium, potassium, calcium, magnesium, aluminum, iron, and zinc ions. Examples of amine salts include salts with ammonia and organic nitrogenous bases strong enough to form salts with carboxylic acids.

"Therapeutically-effective amount" refers to an amount of a compound that, when administered to a subject for treating a disease, is sufficient to effect treatment for the disease. "Therapeutically effective amount" can vary depending on the compound, the disease and its severity, the age, the weight, etc. of the subject to be treated.

Embraced herein, where applicable, are permissible isomers such as tautomers, racemates, enantiomers, diastereomers, atropisomers, configurational isomers of double bonds (E- and/or Z-), cis- and trans-configurations in ring substitution patterns, and isotopic variants.

In one embodiment, the invention provides a compound of Formula (I) or a pharmaceutically acceptable salt thereof:

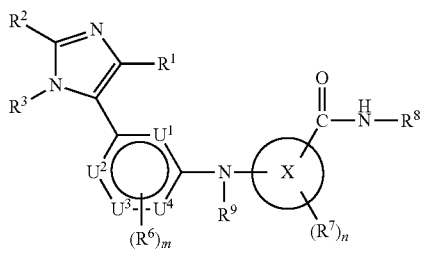

Formula (I)

wherein n, m, $U^1$, $U^2$, $U^3$, $U^4$, $R^1$, $R^2$, $R^3$, $R^6$, $R^7$, $R^8$, $R^9$ and X are as defined above.

In particular embodiments, the variables are further exemplified as follows:

$R^1$, $R^2$ and $R^3$ are independently selected from the group consisting of H, halo, nitro, cyano, hydroxy, hydroxyalkyl, haloalkyl, haloalkoxy, amino, azido, carboxyl, carbamoyl, mercapto, sulphamoyl, alkyl, $C_{2-6}$ alkenyl, $C_{2-6}$ alkynyl, $C_{1-6}$ alkoxy, $C_{1-6}$ alkanoyl, $C_{1-6}$ alkanoyloxy, N—($C_{1-6}$ alkyl)amino, N,N—($C_{1-6}$ alkyl)$_2$amino, $C_{1-6}$ alkanoylamino, N—($C_{1-6}$ alkyl)carbamoyl, N,N—($C_{1-6}$ alkyl)$_2$carbamoyl, $C_{1-6}$ alkyl-S(O)a wherein a is 0, 1 or 2, $C_{1-6}$ alkoxycarbonyl, NH$_2$—S(O)$_2$NH—, N—($C_{1-6}$ alkyl)sulphamoyl, N,N—($C_{1-6}$ alkyl)$_2$sulphamoyl, aryl, aryloxy, arylthio, cycloalkyl, cycloalkyloxy, heterocyclyl, heterocyclyl(C=O)-, heterocyclyloxy and heterocyclylthio; wherein each $R^1$, $R^2$ and $R^3$ is optionally substituted by one or more A where such an optional substitution is chemically feasible;

$U^1$, $U^2$, $U^3$ and $U^4$ are as defined above;

m is 0, 1, or 2;

n is 0, 1, or 2;

each $R^6$ is halo, hydroxy, nitro, cyano, trifluoromethyl, trifluoromethoxy, amino, carboxyl, carbamoyl, sulphamoyl, $C_{1-3}$ alkyl, $C_{2-3}$ alkenyl, $C_{2-3}$ alkynyl, $C_{1-3}$ alkoxy, $C_{1-3}$ alkanoyl, N—($C_{1-3}$ alkyl)amino, N,N—($C_{1-2}$ alkyl)$_2$ amino, $C_{1-3}$ alkanoylamino, N—($C_{1-3}$ alkyl)carbamoyl, N,N—($C_{1-2}$ alkyl)$_2$ carbamoyl, $C_{1-3}$ alkyl-S(O)$_a$ wherein a is 0, 1 or 2, NH$_2$—S(O)$_2$NH—, N—($C_{1-3}$ alkyl)sulphamoyl or N,N—($C_{1-3}$ alkyl)$_2$sulphamoyl; wherein $R^6$ is optionally substituted by one or more B where such an optional substitution is chemically feasible;

X is phenyl, 5-membered heteroaryl, or 6-membered heteroaryl, wherein the heteroaryl contains one or more heteroatoms selected from N, S and O;

each $R^7$ is halo, nitro, cyano, trifluoromethyl, trifluoromethoxy, amino, carboxyl, carbamoyl, sulphamoyl, $C_{1-3}$ alkyl, $C_{2-3}$ alkenyl, $C_{2-3}$ alkynyl, $C_{1-3}$ alkoxy, $C_{1-3}$ alkanoyl, N—($C_{1-3}$ alkyl)amino, N,N—($C_{1-2}$ alkyl)$_2$ amino, $C_{1-3}$ alkanoylamino, N—($C_{1-3}$ alkyl)carbamoyl, N,N—($C_{1-2}$ alkyl)$_2$ carbamoyl, $C_{1-3}$ alkyl-S(O)$_a$ wherein a is 0, 1 or 2, NH$_2$—S(O)$_2$NH—, N—($C_{1-3}$ alkyl)sulphamoyl or N,N—($C_{1-3}$ alkyl)$_2$sulphamoyl,and n is as defined above;

$R^8$ is hydroxy, aryl or heteroaryl, wherein aryl or heteroaryl are substituted with —NH$_2$ or —OH and aryl or heteroaryl is optionally further substituted with one or more groups selected from amino, halo, alkyl, alkenyl, alkynyl, haloalkyl, cycloalkyl, heterocyclyl, aryl, haloaryl, haloheterocyclyl, wherein alkyl, alkenyl, or alkynyl is optionally further substituted with one or more groups selected from halo, hydroxy, alkyl, haloalkyl and cycloalkyl;

$R^9$ is H, alkyl, haloalkyl, aminoalkyl, cycloalkyl, heterocyclyl or aryl, wherein $R^9$ is optionally substituted by one or more D where such an optional substitution is chemically feasible; and A, B and D are independently selected from halo, nitro, cyano, hydroxy, oxo, hydroxyalkyl, haloalkyl, haloalkoxy, amino, azido, carboxyl, carbamoyl, mercapto, sulphamoyl, $C_{1-6}$ alkyl, $C_{2-6}$ alkenyl, $C_{2-6}$ alkynyl, $C_{1-6}$ alkoxy, $C_{1-6}$ alkanoyl, $C_{1-6}$ alkanoyloxy, N—($C_{1-6}$ alkyl)amino, N,N—($C_{1-6}$ alkyl)$_2$amino, $C_{1-6}$ alkanoylamino, N—($C_{1-6}$ alkyl)carbamoyl, N,N—($C_{1-6}$ alkyl)$_2$carbamoyl, $C_{1-6}$ alkyl-S(O)$_a$ wherein a is 0, 1 or 2, $C_{1-6}$ alkoxycarbonyl, N—($C_{1-6}$ alkyl)sulphamoyl, N,N—($C_{1-6}$ alkyl)$_2$sulphamoyl, H$_2$NS(O)$_2$NH—, N—($C_{1-6}$ alkyl)NHS(O)$_2$NH—, N,N—($C_{1-6}$ alkyl)$_2$NS(O)$_2$NH—, aryl, aryloxy, arylthio, cycloalkyl, cycloalkyloxy, heterocyclyl, heterocyclyl(C=O)—, heterocyclyloxy and heterocyclylthio.

In particular embodiments, compounds are selected from those of Formulae ($I^a$), ($I^b$) and ($I^c$), with substituents defined as in Formula (I):

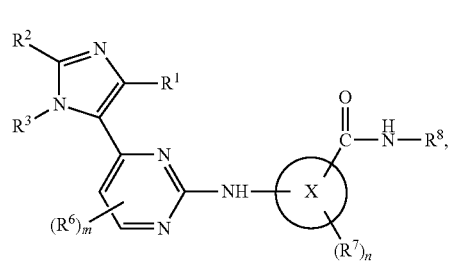

Formula ($I^a$)

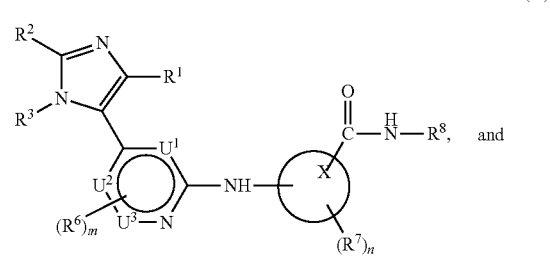

Formula ($I^b$), and

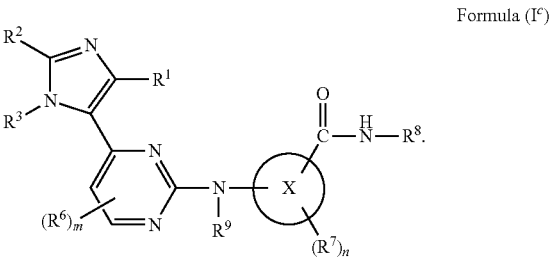

Formula ($I^c$)

Formula ($I^a$) represents pyrimidine compounds, while Formula ($I^b$) represents inhibitors where at least $U^4$ is nitrogen. Formula ($I^b$) represents pyridine compounds when $U^1$, $U^2$, and $U^3$ all comprise ring carbons. In various embodiments, $U^1$, $U^2$ and $U^3$ are selected to be any of (a) $U^1$, $U^2$ and $U^3$ are —CH— or —CR$^6$—; (b) $U^1$ and $U^2$ are —CH— or —CR— and $U^3$ is —N—; (c) $U^1$ and $U^3$ are —CH— or —CR— and $U^2$ is —N—; (d) $U^1$ and $U^3$ are —N— and $U^2$ is —CH— or —CR$^6$—; and (e) $U^1$ and $U^2$ are —N— and $U^3$ is —CH— or —CR$^6$—.

Formula ($I^c$) represents pyrimidine compounds containing a —NR$^9$— linker where $R^9$ is a non-hydrogen substituent selected from alkyl, haloalkyl, aminoalkyl, cycloalkyl, heterocyclyl, aryl, haloaryl and haloheterocyclyl, and $R^9$ can be optionally substituted as described herein.

Compounds defined above are useful to inhibit HDACs and/or CDKs. In a particular embodiment, a compound of the invention inhibits both HDAC and CDK. In one embodiment, therefore, a compound of the invention is used in inhibiting HDAC and/or CDK enzymes such as, for example, mammalian HDAC and/or CDK. More specifically, a compound of the invention can be used to treat or inhibit HDAC and/or CDK-mediated diseases or abnormalities.

In an embodiment of the compounds, one or more (including all) of the substituents $R^1$, $R^2$, $R^3$, $R^6$, $R^7$, $R^8$, $R^9$, $U^1$, $U^2$, $U^3$, $U^4$, and X are exemplified as follows:

$R^1$, $R^2$ and $R^3$ are independently selected from the group consisting of H, chloro, fluoro, bromo, methyl, ethyl, propyl, isopropyl, methoxy, ethoxy, acetyl, carboxyl, methylcarboxyl, cyano, methoxymethyl, ethoxyethyl, propoxyethyl, methoxyethoxy, trifluoromethyl, hydroxyethoxy, dimethylamino, diethylamino, dimethylaminomethyl, dimethylaminoethyl, diethylaminomethyl, dimethylaminoethoxy, dimethylaminocarbonyl, dimethylaminoethylamide, trifluoromethoxymethyl, trifluoroethoxymethyl, isopropylcarbonyl, 1-hydroxyethyl, 3-oxetanoxy, trifluoroethylaminomethyl, N-methyl-N-methoxyethyl-aminomethyl, cyclopropanylmethyl, cyclobutoxy, 1-cyclopropanylethoxy, cyclopropanylmethylaminomethyl, 4-methylpiperazin-1-carbonyl, isoindolin-2-yl, N-methoxyethylcarbamoyl, N-(morpholin-4-yl)-ethylcarbamoyl, dimethylaminoethylamino, N,N-dimethylaminoethylcarbamoyl, benzyl, phenylethyl, trifluoromethylphenylethyl, phenoxymethyl, fluorophenoxymethyl, phenylethylaminomethyl, benzylaminomethyl, triazinylmethyl, piperidinylmethyl, piperidinyloxy, trifluoromethylpiperidinylmethyl, pyridinyloxymethyl, pyridinylmethoxy, tetrahydropyrazinyloxy, methylpiperazinylmethyl, methanesulfonyl, pyrrolidin-1-yl, pyrrolidin-2-yl, pyrrolidin-3-yl, pyrrolidin-1-ylmethyl, pyrrolidin-2-ylmethyl, pyrrolidin-3-ylmethyl, pyrrolidin-1-ylethoxy, pyrrolidin-2-ylethoxy, pyrrolidin-3-ylethoxy, thiazol-4-yl, 2-methyl-thiazol-4-yl, imidazol-1-ylmethyl, imidazol-2-ylmethyl, imidazol-4-ylmethyl, imidazolidin-1-yl, imidazolidin-2-yl, imidazolidin-4-yl, imidazolidin-1-ylmethyl, imidazolidin-2-ylmethyl, imidazolidin-4-ylmethyl, imidazolin-1-yl, imidazolin-2-yl, imidazolin-4-yl, pyrazolidin-1-yl, pyrazolidin-3-yl, pyrazolidin-4-yl, pyrazolin-1-yl, pyrazolin-3-yl, pyrazolin-4-yl, piperidin-1-yl, piperidin-2-yl, piperidin-3-yl, piperidin-4-yl, piperidin-1-ylmethyl, piperidin-2-ylmethyl, piperidin-3-ylmethyl, piperidin-4-ylmethyl, piperazin-1-yl, piperazin-2-yl, piperazin-3-yl, morpholin-2-yl, morpholin-3-yl, morpholin-4-yl, morpholin-2-ylmethyl, morpholin-3-ylmethyl, morpholin-4-ylmethyl, morpholin-4-ylsulfonyl, morpholin-2-ylethoxy, morpholin-3-ylethoxy and morpholin-4-ylethoxy;

In various embodiments, $U^1$, $U^2$, $U^3$ and $U^4$ are selected to form any of the following 6-membered heteroaryl moieties:

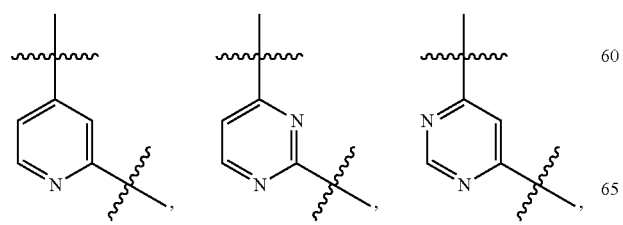

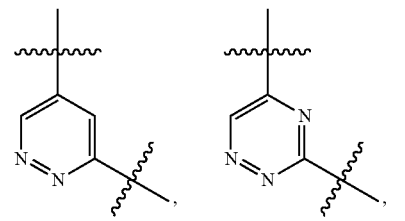

optionally the 6-membered nitrogen containing heteroaryls are substituted with one or more $R^6$;

$R^6$ is methyl, ethyl, hydroxy, flouoro, bromo or trifluoromethyl and m is 0 or 1;

X is phenyl or 5- or 6-membered heteroaryl;

$R^7$ is independently fluoro, chloro, bromo, or methyl and n is 0, 1 or 2; and $R^8$ is hydroxy, aryl or heteroaryl, wherein aryl or heteroaryl are substituted with —$NH_2$ or —OH at a ring position adjacent to attachment of the —CONH-moiety, and $R^8$ is optionally further substituted with one or more groups selected from amino, halo, alkyl, alkenyl, alkynyl, haloalkyl, cycloalkyl, heterocyclyl, aryl, haloaryl, haloheterocyclyl, wherein alkyl, alkenyl, or alkynyl is optionally further substituted with one or more groups selected from halo, hydroxy, alkyl, haloalkyl and cycloalkyl.

In particular embodiments, $R^8$ is hydroxy,

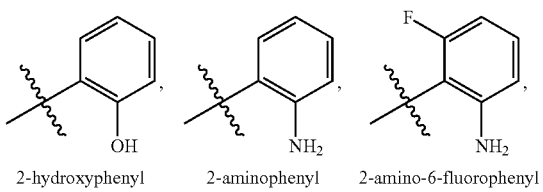

2-hydroxyphenyl, 2-aminophenyl, 2-amino-6-fluorophenyl

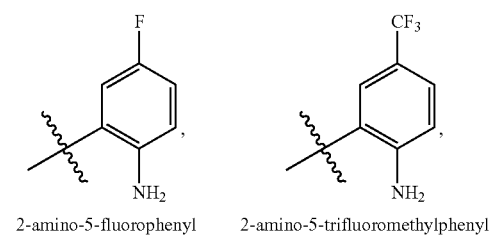

2-amino-5-fluorophenyl, 2-amino-5-trifluoromethylphenyl

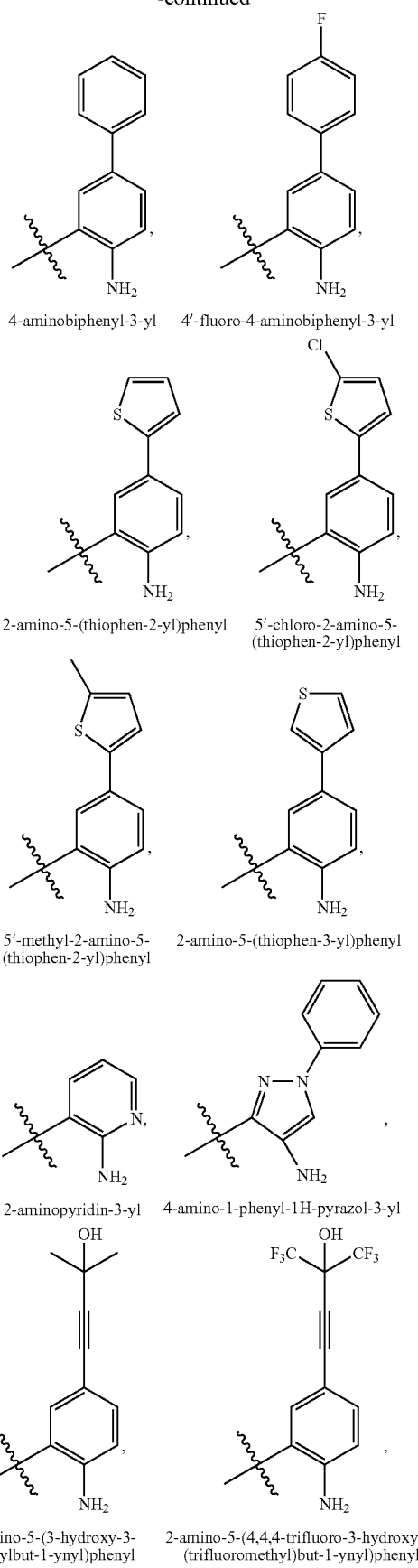

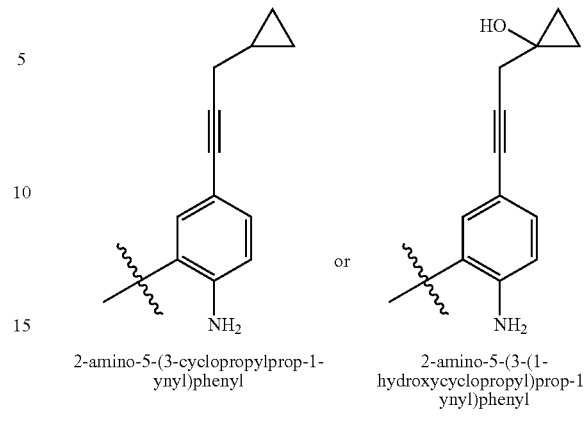

In various embodiments, X is a phenyl ring and the NH (or N—$R^9$) linker and —CONHR$^8$ moiety are disposed about the phenyl ring of Formulae ($I^a$), ($I^b$), or ($I^c$) in either a 1,3-(meta) or a 1,4-(para) configuration. $R^7$ can be attached to any ring position of the phenyl ring not occupied by the linker and —CONHR$^8$ moiety. Such attachment includes 1,2-(ortho), 1,3-(meta) and 1,4-(para) configurations wherein the linker is at position 1. In the Tables that follow, ortho-, meta- and para-configurations of $R^7$ mean attachment to positions 2, 3, and 4, respectively, of the phenyl ring as shown in Formulae ($I^a$-a), ($I^b$-a), ($I^b$-b), ($I^b$-c), ($I^b$-d), and ($I^c$a). Where $R^7$ is an ortho-substitution (i.e., position 2), meta-CONHR$^8$ moiety is intended to be at position 5.

In various embodiments, the invention provides a compound of Formula ($I^a$) and a pharmaceutically acceptable salt thereof:

Formula ($I^a$)

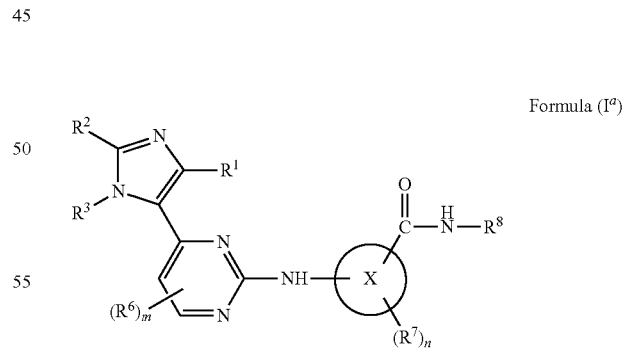

wherein m, n, $R^1$, $R^2$, $R^3$, $R^6$, $R^7$ and $R^8$ are as defined above for various aspects of Formula (I).

In particular embodiments, the invention provides a compound of Formula ($I^a$-a) (i.e., Formula ($I^a$) where X is phenyl) and a pharmaceutically acceptable salt thereof:

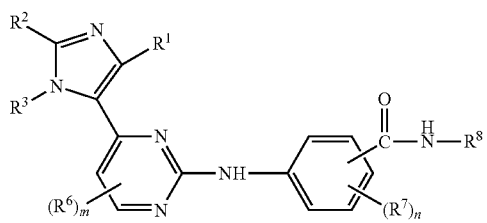

Formula (I$^a$-a)

wherein R$^1$, R$^2$, R$^3$, R$^6$, R$^7$ and R$^8$ are as defined for various aspects of Formula (I) above. In Formula (I$^a$-a), an imidazole ring is substituted on a pyrimidine. The compounds are hydroxamates when R$^8$ is hydroxy, and arylamides when R$^8$ is substituted aryl or substituted heteroaryl. Table 1 provides non-limiting examples of compounds of Formula (I$^a$-a) where m is zero and R$^{7'}$ is H or R$^7$, as shown in Structure (A).

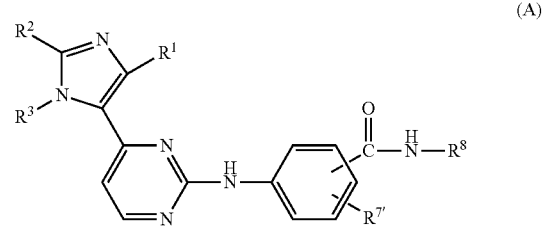

(A)

TABLE 1

Exemplary compounds of Structure (A):

| Compound No. | R$^1$ | R$^2$ | R$^3$ | R$^{7'}$ | —CONHR$^8$ attachment | R$^8$ |
|---|---|---|---|---|---|---|
| a-01 | H | —CH$_3$ | isopropyl | H | para | —OH |
| a-02 | H | —CH$_3$ | isopropyl | H | para | 2-aminophenyl |
| a-03 | H | —CH$_3$ | isopropyl | H | meta | —OH |
| a-04 | H | —CH$_3$ | isopropyl | H | meta | 2-aminophenyl |
| a-05 | —CH$_3$ | —CH$_3$ | isopropyl | H | para | —OH |
| a-06 | —CH$_3$ | —CH$_3$ | isopropyl | H | para | 2-aminophenyl |
| a-07 | —CH$_3$ | —CH$_3$ | isopropyl | H | meta | —OH |
| a-08 | —CH$_3$ | —CH$_3$ | isopropyl | H | meta | 2-aminophenyl |
| a-09 | H | —CH$_3$ | CH$_3$C(O)— | H | para | —OH |
| a-10 | H | methoxyethylaminomethyl | H | H | para | —OH |
| a-11 | H | (pyridin-2-ylamino)methyl | H | H | para | —OH |
| a-12 | H | (2,2,2-trifluoroethylamino)methyl | H | H | para | —OH |
| a-13 | H | (cyclopropylmethylamino)methyl | H | H | para | —OH |
| a-14 | H | —CH$_3$ | CH$_3$C(O)— | H | meta | —OH |
| a-15 | H | methoxyethylaminomethyl | H | H | meta | —OH |
| a-16 | H | (pyridin-2-ylamino)methyl | H | H | meta | —OH |
| a-17 | H | (2,2,2-trifluoroethylamino)methyl | H | H | meta | —OH |

TABLE 1-continued

Exemplary compounds of Structure (A):

| Compound No. | R¹ | R² | R³ | R⁷ | —CONHR⁸ attachment | R⁸ |
|---|---|---|---|---|---|---|
| a-18 | H | cyclopropylmethyl-NH- | H | H | meta | —OH |
| a-19 | H | —CH₃ | CH₃C(O)— | H | para | 2-aminophenyl |
| a-20 | H | methoxyethyl-NH- | H | H | para | 2-aminophenyl |
| a-21 | H | pyridin-2-yl-NH- | H | H | para | 2-aminophenyl |
| a-22 | H | CF₃CH₂-NH- | H | H | para | 2-aminophenyl |
| a-23 | H | cyclopropylmethyl-NH- | H | H | para | 2-aminophenyl |
| a-24 | H | —CH₃ | CH₃C(O)— | H | meta | 2-aminophenyl |
| a-25 | H | methoxyethyl-NH- | H | H | meta | 2-aminophenyl |
| a-26 | H | pyridin-2-yl-NH- | H | H | meta | 2-aminophenyl |
| a-27 | H | CF₃CH₂-NH- | H | H | meta | 2-aminophenyl |
| a-28 | H | cyclopropylmethyl-NH- | H | H | meta | 2-aminophenyl |
| a-29 | H | —CH₃ | isopropyl | H | para | 2-amino-6-fluorophenyl |
| a-30 | H | —CH₃ | isopropyl | H | meta | 2-amino-6-fluorophenyl |
| a-31 | H | —CH₃ | isopropyl | H | para | 2-amino-5-fluorophenyl |
| a-32 | H | —CH₃ | isopropyl | H | meta | 2-amino-5-fluorophenyl |
| a-33 | H | —CH₃ | isopropyl | H | para | 2-amino-5-trifluoromethyl phenyl |
| a-34 | H | —CH₃ | isopropyl | H | meta | 2-amino-5-trifluoromethyl phenyl |

TABLE 1-continued
Exemplary compounds of Structure (A):
| Compound No. | R¹ | R² | R³ | R⁷' | —CONHR⁸ attachment | R⁸ |
|---|---|---|---|---|---|---|
| a-35 | H | —CH₃ | isopropyl | H | para | |
| a-36 | H | —CH₃ | isopropyl | H | meta | |
| a-37 | H | —CH₃ | isopropyl | ortho-F | para | —OH |
| a-38 | H | —CH₃ | isopropyl | ortho-F | para | 2-aminophenyl |
| a-39 | H | —CH₃ | isopropyl | H | para | —OH |
| a-40 | H | —CH₃ | isopropyl | H | para | |
| a-41 | H | —CH₃ | isopropyl | ortho-F | para | —OH |
| a-42 | H | —CH₃ | isopropyl | ortho-F | para | |
Compound a-43
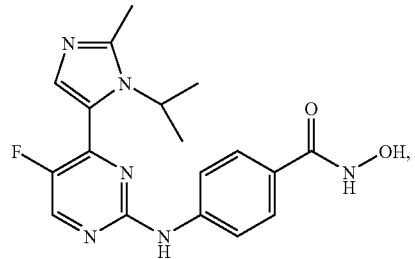
Compound a-44
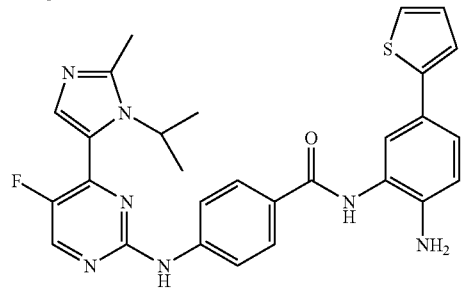

In another embodiment, the invention provides a compound of Formulae (I$^a$-b) (i.e., Formula (I$^a$) where X is thiophene) and a pharmaceutically acceptable salt thereof:

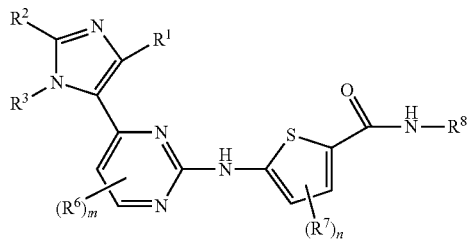

Formula (I$^a$-b)

wherein m, $R^1$, $R^2$, $R^3$, $R^6$, $R^7$ and $R^8$ are as defined for various aspects of Formula (I) above, and where n is 0, 1, or 2.

Non-limiting examples of such compounds include those shown in Table 2 and selected from Structure (B) and pharmaceutically acceptable salts thereof, wherein $R^{7'}$ is $R^7$ or H:

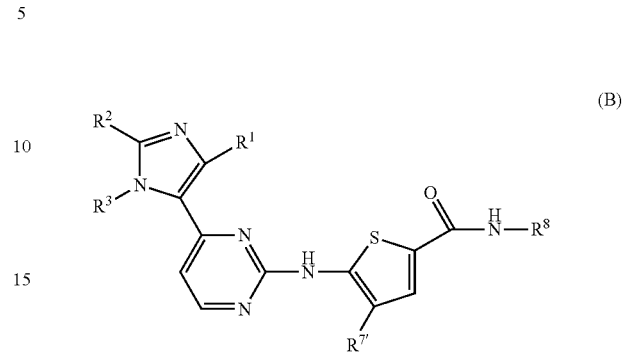

(B)

TABLE 2

Exemplary compounds of Structure (B):

| Compound No. | $R^1$ | $R^2$ | $R^3$ | $R^{7'}$ | $R^8$ |
|---|---|---|---|---|---|
| b-01 | H | —CH$_3$ | isopropyl | H | —OH |
| b-02 | H | —CH$_3$ | isopropyl | H | 2-aminophenyl |
| b-03 | H | —CH$_3$ | isopropyl | H | —OH |
| b-04 | H | —CH$_3$ | isopropyl | H | 2-aminophenyl |
| b-05 | —CH$_3$ | —CH$_3$ | isopropyl | H | —OH |
| b-06 | —CH$_3$ | —CH$_3$ | isopropyl | H | 2-aminophenyl |
| b-07 | —CH$_3$ | —CH$_3$ | isopropyl | H | —OH |
| b-08 | —CH$_3$ | —CH$_3$ | isopropyl | H | 2-aminophenyl |
| b-09 | H | —CH$_3$ | CH$_3$C(O)— | H | —OH |
| b-10 | H | methoxyethylaminomethyl | H | H | —OH |
| b-11 | H | (pyridin-2-ylamino)methyl | H | H | —OH |
| b-12 | H | (2,2,2-trifluoroethylamino)methyl | H | H | —OH |
| b-13 | H | (cyclopropylmethylamino)methyl | H | H | —OH |
| b-14 | H | —CH$_3$ | CH$_3$C(O)— | H | —OH |
| b-15 | H | methoxyethylaminomethyl | H | H | —OH |
| b-16 | H | (pyridin-2-ylamino)methyl | H | H | —OH |
| b-17 | H | (2,2,2-trifluoroethylamino)methyl | H | H | —OH |

TABLE 2-continued

Exemplary compounds of Structure (B):

| Compound No. | R¹ | R² | R³ | R⁷ | R⁸ |
|---|---|---|---|---|---|
| b-18 | H | cyclopropylmethyl-NH- | H | H | —OH |
| b-19 | H | —CH₃ | CH₃C(O)— | H | 2-aminophenyl |
| b-20 | H | 2-methoxyethyl-NH- | H | H | 2-aminophenyl |
| b-21 | H | pyridin-2-yl-NH- | H | H | 2-aminophenyl |
| b-22 | H | 2,2,2-trifluoroethyl-NH- | H | H | 2-aminophenyl |
| b-23 | H | cyclopropylmethyl-NH- | H | H | 2-aminophenyl |
| b-24 | H | —CH₃ | CH₃C(O)— | H | 2-aminophenyl |
| b-25 | H | 2-methoxyethyl-NH- | H | H | 2-aminophenyl |
| b-26 | H | pyridin-2-yl-NH- | H | H | 2-aminophenyl |
| b-27 | H | 2,2,2-trifluoroethyl-NH- | H | H | 2-aminophenyl |
| b-28 | H | cyclopropylmethyl-NH- | H | H | 2-aminophenyl |
| b-29 | H | —CH₃ | isopropyl | H | 2-amino-6-fluorophenyl |
| b-30 | H | —CH₃ | isopropyl | H | 2-amino-5-fluorophenyl |
| b-31 | H | —CH₃ | isopropyl | H | 2-amino-5-trifluoromethyl phenyl |
| b-32 | H | —CH₃ | isopropyl | H | 2-amino-4-(thiophen-2-yl)phenyl |

TABLE 2-continued

Exemplary compounds of Structure (B):

| Compound No. | R¹ | R² | R³ | R⁷ | R⁸ |
|---|---|---|---|---|---|
| b-33 | H | —CH₃ | isopropyl | H | ![structure with 4-fluorobiphenyl and H₂N] |
| b-34 | H | —CH₃ | isopropyl | —CH₃ | ![structure with 4-fluorobiphenyl and H₂N] |

Compound b-35

[structure]

Compound b-36

[structure]

In another embodiment, such compounds include the following compounds and pharmaceutically acceptable salts thereof:

wherein m, $R^1$, $R^2$, $R^3$, $R^6$, $R^7$ and $R^8$ are as defined for various aspects of Formula (I) above; and n is 0 or 1. These are compounds of Formula ($I^a$) where X is thiazole.

Non-limiting examples of such compounds include the following compounds and pharmaceutically acceptable salts thereof:

Formula ($I^a$-c)

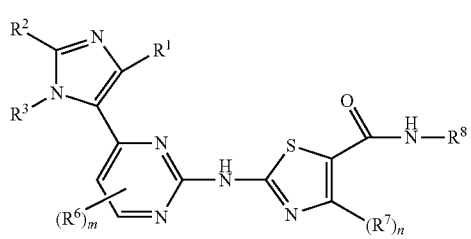

(C)

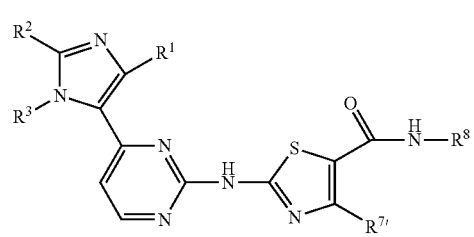

TABLE 3

Exemplary compounds of Structure (C):

| Compound No. | R$^1$ | R$^2$ | R$^3$ | R$^7$ | R$^8$ |
|---|---|---|---|---|---|
| c-01 | H | —CH$_3$ | isopropyl | H | —OH |
| c-02 | H | —CH$_3$ | isopropyl | H | 2-aminophenyl |
| c-03 | H | —CH$_3$ | isopropyl | H | —OH |
| c-04 | H | —CH$_3$ | isopropyl | H | 2-aminophenyl |
| c-05 | —CH$_3$ | —CH$_3$ | isopropyl | H | —OH |
| c-06 | —CH$_3$ | —CH$_3$ | isopropyl | H | 2-aminophenyl |
| c-07 | —CH$_3$ | —CH$_3$ | isopropyl | H | —OH |
| c-08 | —CH$_3$ | —CH$_3$ | isopropyl | H | 2-aminophenyl |
| c-09 | H | —CH$_3$ | CH$_3$C(O)— | H | —OH |
| c-10 | H | CH$_3$OCH$_2$CH$_2$NH— | H | H | —OH |
| c-11 | H | 2-pyridyl-NH— | H | H | —OH |
| c-12 | H | CF$_3$CH$_2$NH— | H | H | —OH |
| c-13 | H | cyclopropyl-CH$_2$NH— | H | H | —OH |
| c-14 | H | —CH$_3$ | CH$_3$C(O)— | H | —OH |
| c-15 | H | CH$_3$OCH$_2$CH$_2$NH— | H | H | —OH |
| c-16 | H | 2-pyridyl-NH— | H | H | —OH |
| c-17 | H | CF$_3$CH$_2$NH— | H | H | —OH |
| c-18 | H | cyclopropyl-CH$_2$NH— | H | H | —OH |
| c-19 | H | —CH$_3$ | CH$_3$C(O)— | H | 2-aminophenyl |
| c-20 | H | CH$_3$OCH$_2$CH$_2$NH— | H | H | 2-aminophenyl |
| c-21 | H | 2-pyridyl-NH— | H | H | 2-aminophenyl |
| c-22 | H | CF$_3$CH$_2$NH— | H | H | 2-aminophenyl |

TABLE 3-continued

Exemplary compounds of Structure (C):

| Compound No. | R¹ | R² | R³ | R⁷ | R⁸ |
|---|---|---|---|---|---|
| c-23 | H | cyclopropylmethyl-NH-C(CH₃)₂- | H | H | 2-aminophenyl |
| c-24 | H | —CH₃ | CH₃C(O)— | H | 2-aminophenyl |
| c-25 | H | methoxyethyl-NH-CH- | H | H | 2-aminophenyl |
| c-26 | H | (pyridin-2-yl)-NH-C(CH₃)₂- | H | H | 2-aminophenyl |
| c-27 | H | F₃C-CH₂-NH-C(CH₃)₂- | H | H | 2-aminophenyl |
| c-28 | H | cyclopropylmethyl-NH-C(CH₃)₂- | H | H | 2-aminophenyl |
| c-29 | H | —CH₃ | isopropyl | H | 2-amino-6-fluorophenyl |
| c-30 | H | —CH₃ | isopropyl | H | 2-amino-5-fluorophenyl |
| c-31 | H | —CH₃ | isopropyl | H | 2-amino-5-trifluoromethyl phenyl |
| c-32 | H | —CH₃ | isopropyl | H | 2-amino-4-(thiophen-2-yl)phenyl |
| c-33 | H | —CH₃ | isopropyl | H | 4-amino-4'-fluoro-[1,1'-biphenyl]-3-yl |
| c-34 | H | —CH₃ | isopropyl | —CH₃ | 4-amino-4'-fluoro-[1,1'-biphenyl]-3-yl |

TABLE 3-continued

Exemplary compounds of Structure (C):

| Compound No. | R¹ | R² | R³ | R⁷ | R⁸ |
|---|---|---|---|---|---|

Compound c-35

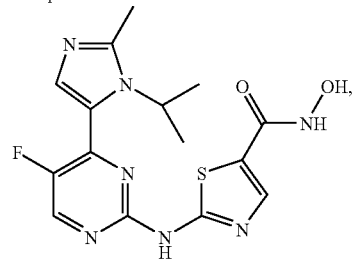

Compound c-36

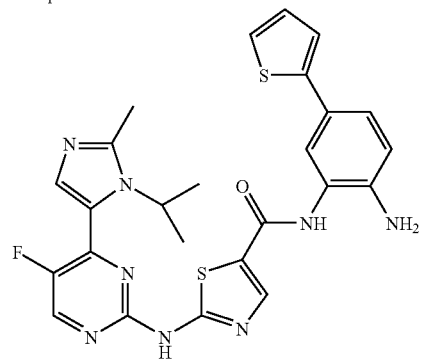

In another embodiment, the invention provides a compound of Formula (I$^b$) or a pharmaceutically acceptable salt thereof:

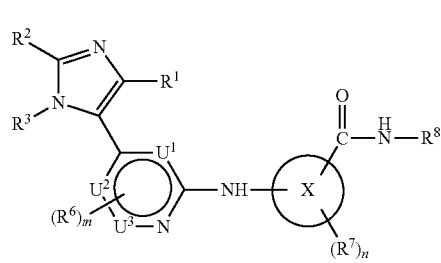

Formula (I$^b$)

wherein m, n, R¹, R², R³, R⁶, R⁷ and R⁸ are as defined above for various aspects of Formula (I); and U¹, U² and U³ are ring atoms independently selected from N and C.

In an embodiment of Formula (I$^b$), R¹, R² and R³ are independently selected from the group consisting of H, chloro, fluoro, bromo, methyl, ethyl, propyl, isopropyl, methoxy, ethoxy, acetyl, carboxyl, methylcarboxyl, cyano, methoxymethyl, ethoxyethyl, propoxyethyl, methoxyethoxy, trifluoromethyl, hydroxyethoxy, dimethylamino, diethylamino, dimethylaminomethyl, dimethylaminoethyl, diethylaminomethyl, dimethylaminoethoxy, dimethylaminocarbonyl, dimethylaminoethylamide, trifluoromethoxymethyl, trifluoroethoxymethyl, isopropylcarbonyl, 1-hydoxyethyl, 3-oxetanoxy, trifluoroethylaminomethyl, N-methyl-N-methoxyethyl-aminomethyl, cyclopropanylmethyl, cyclobutoxy, 1-cyclopropanylethoxy, cyclopropanylmethylaminomethyl, 4-methylpiperazin-1-carbonyl, isoindolin-2-yl, N-methoxyethylcarbamoyl, N-(morpholin-4-yl)-ethylcarbamoyl, dimethylaminoethylamino, N,N-dimethylaminoethylcarbamoyl, benzyl, phenylethyl, trifluoromethylphenylethyl, phenoxymethyl, fluorophenoxymethyl, phenylethylaminomethyl, benzylaminomethyl, triazinylmethyl, piperidinylmethyl, piperidinyloxy, trifluoromethylpiperidinylmethyl, pyridinyloxymethyl, pyridinylmethoxy, tetrahydropyrazinyloxy, methylpiperazinylmethyl, methanesulfonyl, pyrrolidin-1-yl, pyrrolidin-2-yl, pyrrolidin-3-yl, pyrrolidin-1-ylmethyl, pyrrolidin-2-ylmethyl, pyrrolidin-3-ylmethyl, pyrrolidin-1-ylethoxy, pyrrolidin-2-ylethoxy, pyrrolidin-3-ylethoxy, thiazol-4-yl, 2-methyl-thiazol-4-yl, imidazol-1-ylmethyl, imidazol-2-ylmethyl, imidazol-4-ylmethyl, imidazolidin-1-yl, imidazolidin-2-yl, imidazolidin-4-yl, imidazolidin-1-ylmethyl, imidazolidin-2-ylmethyl, imidazolidin-4-ylmethyl, imidazolin-1-yl, imidazolin-2-yl, imidazolin-4-yl, pyrazolidin-1-yl, pyrazolidin-3-yl, pyrazolidin-4-yl, pyrazolin-1-yl, pyrazolin-3-yl, pyrazolin-4-yl, piperidin-1-yl, piperidin-2-yl, piperidin-3-yl, piperidin-4-yl, piperidin-1-ylmethyl, piperidin-2-ylmethyl, piperidin-3-ylmethyl, piperidin-4-ylmethyl, piperazin-1-yl, piperazin-2-yl, piperazin-3-yl, morpholin-2-yl, morpholin-3-yl, morpholin-4-yl, morpholin-2-ylmethyl, morpholin-3-ylmethyl, morpholin-4-ylmethyl, morpholin-4-ylsulfonyl, morpholin-2-ylethoxy, morpholin-3-ylethoxy and morpholin-4-ylethoxy; R⁶ is halo, hydroxy, alkyl or haloalkyl; m is 0 or 1; R⁷ is fluoro, chloro, bromo, or methyl; n is 0, 1 or 2; and R⁸ is hydroxy, aryl or heteroaryl, wherein aryl or heteroaryl are substituted with —NH₂ or —OH at a ring position adjacent to attachment of the —CONH-moiety, and R⁸ is optionally further substituted with one or more groups selected from amino, halo, alkyl, alkenyl, alkynyl, haloalkyl, cycloalkyl, heterocyclyl, aryl, haloaryl, haloheterocyclyl, wherein alkyl, alkenyl, or alkynyl is optionally further substituted with one or more groups selected from halo, hydroxy, alkyl, haloalkyl and cycloalkyl.

In an embodiment, $U^1$, $U^2$ and $U^3$ are selected to be any of the following combinations: $U^1$, $U^2$ and $U^3$ are selected to be any of (a) $U^1$, $U^2$ and $U^3$ are —CH— or —CR$^6$—; (b) $U^1$ and $U^2$ are —CH— or —CR$^6$— and $U^3$ is —N—; (c) $U^1$ and $U^3$ are —CH— or —CR$^6$— and $U^2$ is —N—; and (d) $U^1$ and $U^2$ are —N— and $U^3$ is —CH— or —CR$^6$—.

In an embodiment of Formula ($I^b$) where X is phenyl, such compounds include pyridine compound of Formula ($I^b$-a) and pharmaceutically acceptable salts thereof:

wherein $R^1$, $R^2$, $R^3$, $R^6$, $R^7$ and $R^8$ are as defined for various aspects of Formula (I) above; m is 0, 1, 2, or 3; and n is 0, 1, 2, 3, or 4.

Non-limiting examples of such compounds include the compounds shown in Table 3 and selected from those of Structure (D) and pharmaceutically acceptable salts thereof, where $R^{7'}$ is $R^7$ or H:

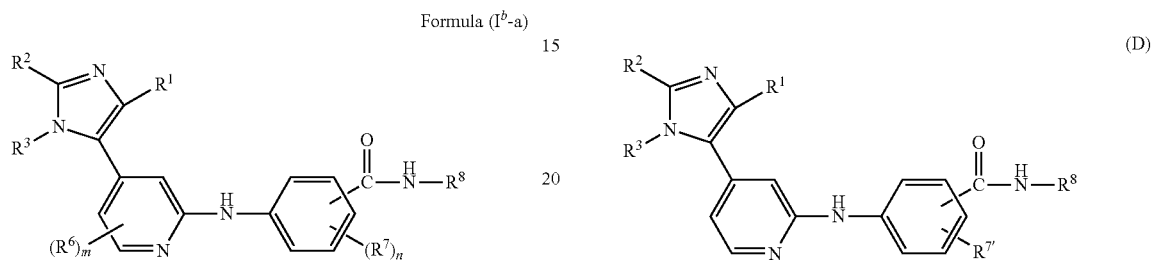

TABLE 4

Exemplary compounds of Structure (D):

| Compound No. | $R^1$ | $R^2$ | $R^3$ | $R^{7'}$ | —CONHR$^8$ attachment | $R^8$ |
|---|---|---|---|---|---|---|
| d-01 | H | —CH$_3$ | isopropyl | H | para | —OH |
| d-02 | H | —CH$_3$ | isopropyl | H | para | 2-aminophenyl |
| d-03 | H | —CH$_3$ | isopropyl | H | meta | —OH |
| d-04 | H | —CH$_3$ | isopropyl | H | meta | 2-aminophenyl |
| d-05 | —CH$_3$ | —CH$_3$ | isopropyl | H | para | —OH |
| d-06 | —CH$_3$ | —CH$_3$ | isopropyl | H | para | 2-aminophenyl |
| d-07 | —CH$_3$ | —CH$_3$ | isopropyl | H | meta | —OH |
| d-08 | —CH$_3$ | —CH$_3$ | isopropyl | H | meta | 2-aminophenyl |
| d-09 | H | —CH$_3$ | CH$_3$C(O)— | H | para | —OH |
| d-10 | H | CH$_3$OCH$_2$CH$_2$NH— | H | H | para | —OH |
| d-11 | H | (2-pyridyl)NHCH$_2$— | H | H | para | —OH |
| d-12 | H | CF$_3$CH$_2$NH— | H | H | para | —OH |
| d-13 | H | cyclopropyl-CH$_2$NH— | H | H | para | —OH |
| d-14 | H | —CH$_3$ | CH$_3$C(O)— | H | meta | —OH |
| d-15 | H | CH$_3$OCH$_2$CH$_2$NH— | H | H | meta | —OH |

TABLE 4-continued

Exemplary compounds of Structure (D):

| Compound No. | R¹ | R² | R³ | R⁷ | —CONHR⁸ attachment | R⁸ |
|---|---|---|---|---|---|---|
| d-16 | H | 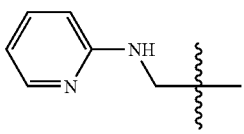 | H | H | meta | —OH |
| d-17 | H | 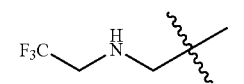 | H | H | meta | —OH |
| d-18 | H | 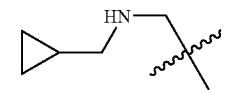 | H | H | meta | —OH |
| d-19 | H | —CH₃ | CH₃C(O)— | H | para | 2-aminophenyl |
| d-20 | H | 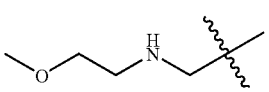 | H | H | para | 2-aminophenyl |
| d-21 | H | 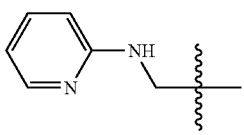 | H | H | para | 2-aminophenyl |
| d-22 | H | 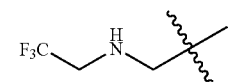 | H | H | para | 2-aminophenyl |
| d-23 | H | 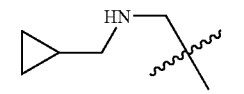 | H | H | para | 2-aminophenyl |
| d-24 | H | —CH₃ | CH₃C(O)— | H | meta | 2-aminophenyl |
| d-25 | H | 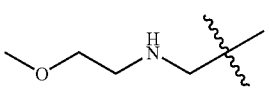 | H | H | meta | 2-aminophenyl |
| d-26 | H | 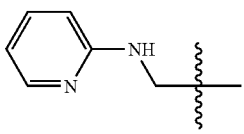 | H | H | meta | 2-aminophenyl |
| d-27 | H | 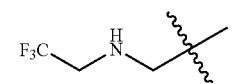 | H | H | meta | 2-aminophenyl |
| d-28 | H | 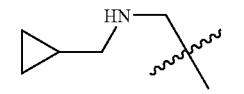 | H | H | meta | 2-aminophenyl |
| d-29 | H | —CH₃ | isopropyl | H | para | 2-amino-6-fluorophenyl |
| d-30 | H | —CH₃ | isopropyl | H | meta | 2-amino-6-fluorophenyl |
| d-31 | H | —CH₃ | isopropyl | H | para | 2-amino-5-fluorophenyl |
| d-32 | H | —CH₃ | isopropyl | H | meta | 2-amino-5-fluorophenyl |
| d-33 | H | —CH₃ | isopropyl | H | para | 2-amino-5-trifluoromethyl |

TABLE 4-continued

Exemplary compounds of Structure (D):

| Compound No. | R¹ | R² | R³ | R⁷ | —CONHR⁸ attachment | R⁸ |
|---|---|---|---|---|---|---|
| d-34 | H | —CH₃ | isopropyl | H | meta | phenyl 2-amino-5-trifluoromethyl phenyl |
| d-35 | H | —CH₃ | isopropyl | H | para | 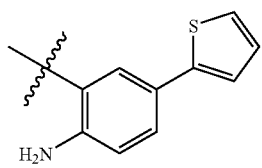 |
| d-36 | H | —CH₃ | isopropyl | H | meta | 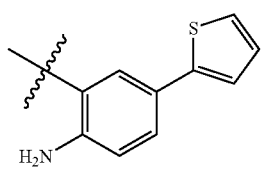 |
| d-37 | H | —CH₃ | isopropyl | ortho-F | para | —OH |
| d-38 | H | —CH₃ | isopropyl | ortho-F | para | 2-aminophenyl |
| d-39 | H | —CH₃ | isopropyl | H | para | —OH |
| d-40 | H | —CH₃ | isopropyl | H | para | 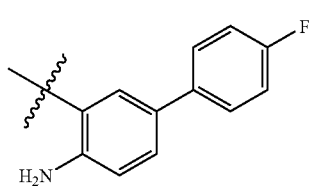 |
| d-41 | H | —CH₃ | isopropyl | ortho-F | para | —OH |
| d-42 | H | —CH₃ | isopropyl | ortho-F | para | 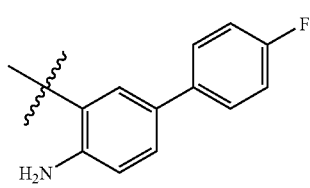 |

In another embodiment, such compounds include pyridazine compounds of Formula (I$^b$-b) and pharmaceutically acceptable salts thereof:

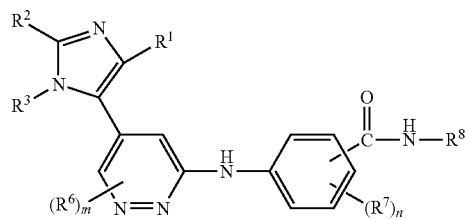

Formula (I$^b$-b)

wherein R¹, R², R³, R⁶, R⁷ and R⁸ are as defined for various aspects of Formula (I) above; m is 0, 1, or 2; and n is 0, 1, 2, 3, or 4.

Non-limiting examples of such compounds include the compounds shown in Table 4 and selected from those of Structure (E) and pharmaceutically acceptable salts thereof, where R⁷' is R⁷ or H:

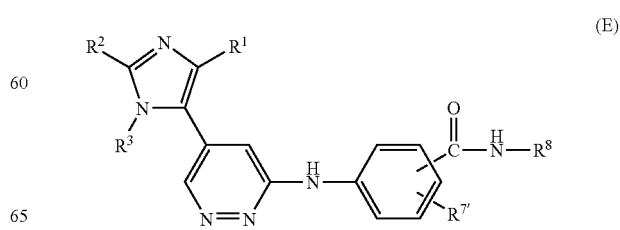

(E)

TABLE 5

Exemplary compounds of Structure (E):

| Compound No. | R¹ | R² | R³ | R⁷ | —CONHR⁸ attachment | R⁸ |
|---|---|---|---|---|---|---|
| e-01 | H | —CH₃ | isopropyl | H | para | —OH |
| e-02 | H | —CH₃ | isopropyl | H | para | 2-aminophenyl |
| e-03 | H | —CH₃ | isopropyl | H | meta | —OH |
| e-04 | H | —CH₃ | isopropyl | H | meta | 2-aminophenyl |
| e-05 | —CH₃ | —CH₃ | isopropyl | H | para | —OH |
| e-06 | —CH₃ | —CH₃ | isopropyl | H | para | 2-aminophenyl |
| e-07 | —CH₃ | —CH₃ | isopropyl | H | meta | —OH |
| e-08 | —CH₃ | —CH₃ | isopropyl | H | meta | 2-aminophenyl |
| e-09 | H | —CH₃ | CH₃C(O)— | H | para | —OH |
| e-10 | H | 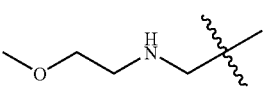 | H | H | para | —OH |
| e-11 | H | 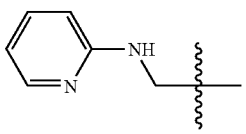 | H | H | para | —OH |
| e-12 | H | 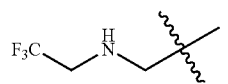 | H | H | para | —OH |
| e-13 | H | 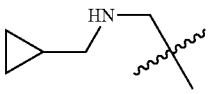 | H | H | para | —OH |
| e-14 | H | —CH₃ | CH₃C(O)— | H | meta | —OH |
| e-15 | H | 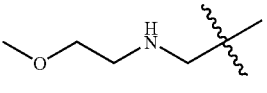 | H | H | meta | —OH |
| e-16 | H | 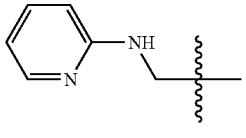 | H | H | meta | —OH |
| e-17 | H | 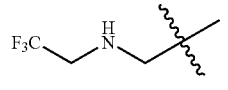 | H | H | meta | —OH |
| e-18 | H | 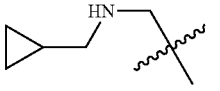 | H | H | meta | —OH |
| e-19 | H | —CH₃ | CH₃C(O)— | H | para | 2-aminophenyl |
| e-20 | H | 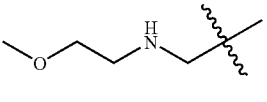 | H | H | para | 2-aminophenyl |
| e-21 | H | 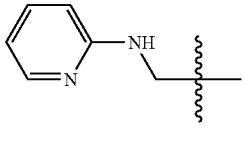 | H | H | para | 2-aminophenyl |
| e-22 | H | 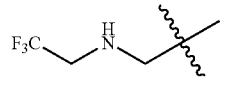 | H | H | para | 2-aminophenyl |

TABLE 5-continued

Exemplary compounds of Structure (E):

| Compound No. | R¹ | R² | R³ | R⁷ | —CONHR⁸ attachment | R⁸ |
|---|---|---|---|---|---|---|
| e-23 | H | cyclopropylmethyl-NH- | H | H | para | 2-aminophenyl |
| e-24 | H | —CH₃ | CH₃C(O)— | H | meta | 2-aminophenyl |
| e-25 | H | CH₃OCH₂CH₂-NH- | H | H | meta | 2-aminophenyl |
| e-26 | H | pyridin-2-yl-NH- | H | H | meta | 2-aminophenyl |
| e-27 | H | F₃C-CH₂-NH- | H | H | meta | 2-aminophenyl |
| e-28 | H | cyclopropylmethyl-NH- | H | H | meta | 2-aminophenyl |
| e-29 | H | —CH₃ | isopropyl | H | para | 2-amino-6-fluorophenyl |
| e-30 | H | —CH₃ | isopropyl | H | meta | 2-amino-6-fluorophenyl |
| e-31 | H | —CH₃ | isopropyl | H | para | 2-amino-5-fluorophenyl |
| e-32 | H | —CH₃ | isopropyl | H | meta | 2-amino-5-fluorophenyl |
| e-33 | H | —CH₃ | isopropyl | H | para | 2-amino-5-trifluoromethyl phenyl |
| e-34 | H | —CH₃ | isopropyl | H | meta | 2-amino-5-trifluoromethyl phenyl |
| e-35 | H | —CH₃ | isopropyl | H | para | 4-amino-3-(thiophen-2-yl)phenyl (attached at position ortho to NH₂) |
| e-36 | H | —CH₃ | isopropyl | H | meta | 4-amino-3-(thiophen-2-yl)phenyl (attached at position ortho to NH₂) |
| e-37 | H | —CH₃ | isopropyl | ortho-F | para | —OH |
| e-38 | H | —CH₃ | isopropyl | ortho-F | para | 2-aminophenyl |
| e-39 | H | —CH3 | isopropyl | H | para | —OH |
| e-40 | H | —CH3 | isopropyl | H | para | 4'-fluoro-4-amino-biphenyl-3-yl |
| e-41 | H | —CH3 | isopropyl | ortho-F | para | —OH |

TABLE 5-continued

Exemplary compounds of Structure (E):

| Compound No. | R¹ | R² | R³ | R⁷ | —CONHR⁸ attachment | R⁸ |
|---|---|---|---|---|---|---|
| e-42 | H | —CH3 | isopropyl | ortho-F | para | 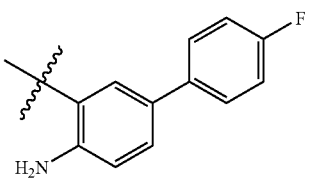 |

In another embodiment, such compounds include 1,3,5-triazine compounds of Formula (I$^b$-c) and pharmaceutically acceptable salts thereof:

(Formula (I$^b$-c))

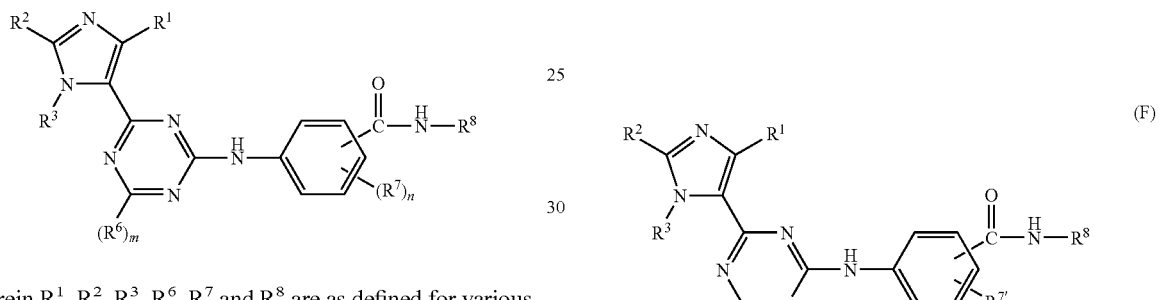

wherein R¹, R², R³, R⁶, R⁷ and R⁸ are as defined for various aspects of Formula (I) above; m is 0 or 1; and n is 0, 1, 2, 3, or 4.

Non-limiting examples of such compounds include the compounds shown in Table 5 and selected from those of Structure (F) and pharmaceutically acceptable salts thereof, where R⁷' is R⁷ or H:

(F)

TABLE 6

Exemplary compounds of Structure (F):

| Compound No. | R¹ | R² | R³ | R⁷' | —CONHR⁸ attachment | R⁸ |
|---|---|---|---|---|---|---|
| f-01 | H | —CH₃ | isopropyl | H | para | —OH |
| f-02 | H | —CH₃ | isopropyl | H | para | 2-aminophenyl |
| f-03 | H | —CH₃ | isopropyl | H | meta | —OH |
| f-04 | H | —CH₃ | isopropyl | H | meta | 2-aminophenyl |
| f-05 | —CH₃ | —CH₃ | isopropyl | H | para | —OH |
| f-06 | —CH₃ | —CH₃ | isopropyl | H | para | 2-aminophenyl |
| f-07 | —CH₃ | —CH₃ | isopropyl | H | meta | —OH |
| f-08 | —CH₃ | —CH₃ | isopropyl | H | meta | 2-aminophenyl |
| f-09 | H | —CH₃ | CH₃C(O)— | H | para | —OH |
| f-10 | H | —CH₃ | 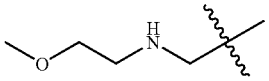 | H | para | —OH |
| f-11 | H | —CH₃ | 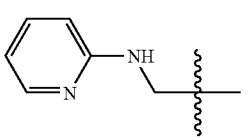 | H | para | —OH |
| f-12 | H | —CH₃ | 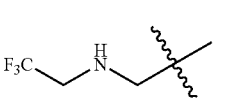 | H | para | —OH |

TABLE 6-continued

Exemplary compounds of Structure (F):

| Compound No. | R¹ | R² | R³ | R⁷ | —CONHR⁸ attachment | R⁸ |
|---|---|---|---|---|---|---|
| f-13 | H | cyclopropylmethyl-NH- | H | H | para | —OH |
| f-14 | H | —CH₃ | CH₃C(O)— | H | meta | —OH |
| f-15 | H | methoxyethyl-NH- | H | H | meta | —OH |
| f-16 | H | pyridin-2-yl-NH- | H | H | meta | —OH |
| f-17 | H | F₃C-CH₂-NH- | H | H | meta | —OH |
| f-18 | H | cyclopropylmethyl-NH- | H | H | meta | —OH |
| f-19 | H | —CH₃ | CH₃C(O)— | H | para | 2-aminophenyl |
| f-20 | H | methoxyethyl-NH- | H | H | para | 2-aminophenyl |
| f-21 | H | pyridin-2-yl-NH- | H | H | para | 2-aminophenyl |
| f-22 | H | F₃C-CH₂-NH- | H | H | para | 2-aminophenyl |
| f-23 | H | cyclopropylmethyl-NH- | H | H | para | 2-aminophenyl |
| f-24 | H | —CH₃ | CH₃C(O)— | H | meta | 2-aminophenyl |
| f-25 | H | methoxyethyl-NH- | H | H | meta | 2-aminophenyl |
| f-26 | H | pyridin-2-yl-NH- | H | H | meta | 2-aminophenyl |
| f-27 | H | F₃C-CH₂-NH- | H | H | meta | 2-aminophenyl |

TABLE 6-continued

Exemplary compounds of Structure (F):

| Compound No. | R¹ | R² | R³ | R⁷ | —CONHR⁸ attachment | R⁸ |
|---|---|---|---|---|---|---|
| f-28 | H | (cyclopropylmethyl-HN-C(CH₃)₂-) | H | H | meta | 2-aminophenyl |
| f-29 | H | —CH₃ | isopropyl | H | para | 2-amino-6-fluorophenyl |
| f-30 | H | —CH₃ | isopropyl | H | meta | 2-amino-6-fluorophenyl |
| f-31 | H | —CH₃ | isopropyl | H | para | 2-amino-5-fluorophenyl |
| f-32 | H | —CH₃ | isopropyl | H | meta | 2-amino-5-fluorophenyl |
| f-33 | H | —CH₃ | isopropyl | H | para | 2-amino-5-trifluoromethyl phenyl |
| f-34 | H | —CH₃ | isopropyl | H | meta | 2-amino-5-trifluoromethyl phenyl |
| f-35 | H | —CH₃ | isopropyl | H | para | 4-amino-3-(thiophen-2-yl)phenyl |
| f-36 | H | —CH₃ | isopropyl | H | meta | 4-amino-3-(thiophen-2-yl)phenyl |
| f-37 | H | —CH₃ | isopropyl | ortho-F | para | —OH |
| f-38 | H | —CH₃ | isopropyl | ortho-F | para | 2-aminophenyl |
| f-39 | H | —CH₃ | isopropyl | H | para | —OH |
| f-40 | H | —CH₃ | isopropyl | H | para | 4-amino-3-(4-fluorophenyl)phenyl |
| f-41 | H | —CH₃ | isopropyl | ortho-F | para | —OH |
| f-42 | H | —CH₃ | isopropyl | ortho-F | para | 4-amino-3-(4-fluorophenyl)phenyl |

In another embodiment, such compounds include 1,2,4-triazine compounds of Formula (I$^b$-d) and pharmaceutically acceptable salts thereof:

(Formula (I$^b$-d))

wherein R$^1$, R$^2$, R$^3$, R$^6$, R$^7$ and R$^8$ are as defined for various aspects of Formula (I) above; m is 0 or 1; and n is 0, 1, 2, 3, or 4.

Non-limiting examples of such compounds include the following compounds and pharmaceutically acceptable salts thereof:

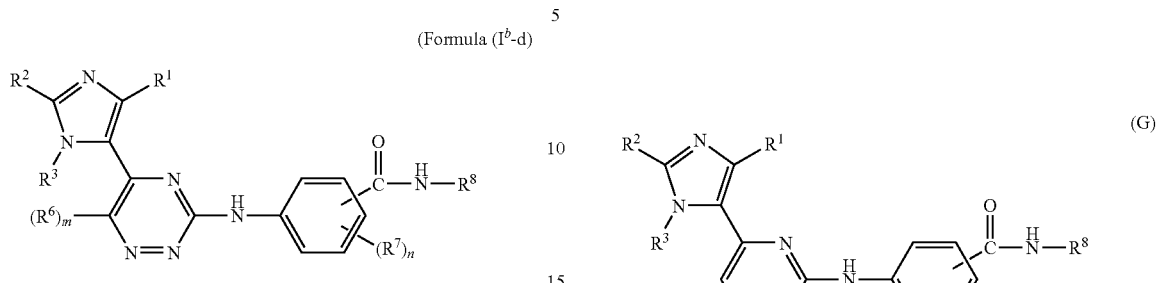

(G)

TABLE 6

Exemplary compounds of Structure (G):

| Compound No. | R$^1$ | R$^2$ | R$^3$ | R$^7$ | —CONHR$^8$ attachment | R$^8$ |
|---|---|---|---|---|---|---|
| g-01 | H | —CH$_3$ | isopropyl | H | para | —OH |
| g-02 | H | —CH$_3$ | isopropyl | H | para | 2-aminophenyl |
| g-03 | H | —CH$_3$ | isopropyl | H | meta | —OH |
| g-04 | H | —CH$_3$ | isopropyl | H | meta | 2-aminophenyl |
| g-05 | —CH$_3$ | —CH$_3$ | isopropyl | H | para | —OH |
| g-06 | —CH$_3$ | —CH$_3$ | isopropyl | H | para | 2-aminophenyl |
| g-07 | —CH$_3$ | —CH$_3$ | isopropyl | H | meta | —OH |
| g-08 | —CH$_3$ | —CH$_3$ | isopropyl | H | meta | 2-aminophenyl |
| g-09 | H | —CH$_3$ | CH$_3$C(O)— | H | para | —OH |
| g-10 | H | methoxyethyl-NH- | H | H | para | —OH |
| g-11 | H | (pyridin-2-yl)-NH- | H | H | para | —OH |
| g-12 | H | F$_3$C-CH$_2$-NH- | H | H | para | —OH |
| g-13 | H | cyclopropylmethyl-NH- | H | H | para | —OH |
| g-14 | H | —CH$_3$ | CH$_3$C(O)— | H | meta | —OH |
| g-15 | H | methoxyethyl-NH- | H | H | meta | —OH |
| g-16 | H | (pyridin-2-yl)-NH- | H | H | meta | —OH |
| g-17 | H | F$_3$C-CH$_2$-NH- | H | H | meta | —OH |

TABLE 6-continued

Exemplary compounds of Structure (G):

| Compound No. | R¹ | R² | R³ | R⁷ | —CONHR⁸ attachment | R⁸ |
|---|---|---|---|---|---|---|
| g-18 | H | HN-cyclopropylmethyl (branched) | H | H | meta | —OH |
| g-19 | H | —CH₃ | CH₃C(O)— | H | para | 2-aminophenyl |
| g-20 | H | methoxyethylamino (branched) | H | H | para | 2-aminophenyl |
| g-21 | H | pyridin-2-ylamino (branched) | H | H | para | 2-aminophenyl |
| g-22 | H | F₃C-CH₂-NH (branched) | H | H | para | 2-aminophenyl |
| g-23 | H | HN-cyclopropylmethyl (branched) | H | H | para | 2-aminophenyl |
| g-24 | H | —CH₃ | CH₃C(O)— | H | meta | 2-aminophenyl |
| g-25 | H | methoxyethylamino (branched) | H | H | meta | 2-aminophenyl |
| g-26 | H | pyridin-2-ylamino (branched) | H | H | meta | 2-aminophenyl |
| g-27 | H | F₃C-CH₂-NH (branched) | H | H | meta | 2-aminophenyl |
| g-28 | H | HN-cyclopropylmethyl (branched) | H | H | meta | 2-aminophenyl |
| g-29 | H | —CH₃ | isopropyl | H | para | 2-amino-6-fluorophenyl |
| g-30 | H | —CH₃ | isopropyl | H | meta | 2-amino-6-fluorophenyl |
| g-31 | H | —CH₃ | isopropyl | H | para | 2-amino-5-fluorophenyl |
| g-32 | H | —CH₃ | isopropyl | H | meta | 2-amino-5-fluorophenyl |
| g-33 | H | —CH₃ | isopropyl | H | para | 2-amino-5-trifluoromethyl phenyl |
| g-34 | H | —CH₃ | isopropyl | H | meta | 2-amino-5-trifluoromethyl phenyl |
| g-35 | H | —CH₃ | isopropyl | H | para | 2-amino-4-(thiophen-2-yl)phenyl |

TABLE 6-continued

Exemplary compounds of Structure (G):

| Compound No. | R¹ | R² | R³ | R⁷ | —CONHR⁸ attachment | R⁸ |
|---|---|---|---|---|---|---|
| g-36 | H | —CH₃ | isopropyl | H | meta | ![3-(thiophen-2-yl)-4-aminophenyl] |
| g-37 | H | —CH₃ | isopropyl | ortho-F | para | —OH |
| g-38 | H | —CH₃ | isopropyl | ortho-F | para | 2-aminophenyl |
| g-39 | H | —CH3 | isopropyl | H | para | —OH |
| g-40 | H | —CH3 | isopropyl | H | para | ![3-(4-fluorophenyl)-4-aminophenyl] |
| g-41 | H | —CH3 | isopropyl | ortho-F | para | —OH |
| g-42 | H | —CH3 | isopropyl | ortho-F | para | ![4'-fluoro-4-aminobiphenyl] |

In another embodiment, the invention provides a pyrimidine compound of Formula (I$^c$) and a pharmaceutically acceptable salt thereof:

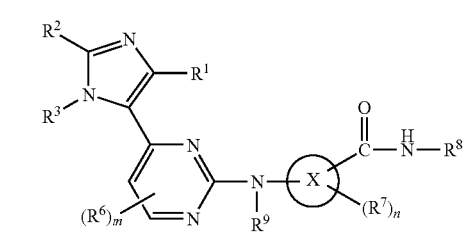

Formula (I$^c$)

wherein m, n, R¹, R², R³, R⁶, R⁷, and R⁸ are as defined above for various aspects of Formula (I); and R⁹ is a non-hydrogen substituent selected from alkyl, haloalkyl, aminoalkyl, cycloalkyl, heterocyclyl and aryl, wherein R⁹ is optionally substituted by one or more D where such an optional substitution is chemically feasible.

In an embodiment of Formula (I$^c$), R¹, R² and R³ are independently selected from the group consisting of H, methyl, ethyl, propyl, chloro, methoxy, ethoxy, methoxymethyl, ethoxyethyl, propoxyethyl, methoxyethoxy, trifluoromethyl, hydroxyethoxy, dimethylamino, diethylamino, dimethylaminomethyl, diethylaminomethyl, dimethylaminoethoxy, trifluoromethoxymethyl, trifluoroethoxymethyl, benzyl, phenylethyl, trifluoromethylphenylethyl, phenoxymethyl, fluorophenoxymethyl, phenylethylaminomethyl, benzylaminomethyl, morpholinylmethyl, morpholinylethoxy, imidazolylmethyl, triazinylmethyl, piperidinylmethyl, piperidinyloxy, trifluoromethylpiperidinylmethyl, pyridinyloxymethyl, pyridinylmethoxy, tetrahydropyrazinyloxy, methylpiperazinylmethyl, pyrrolidinylmethyl and pyrrolidinylethoxy; R⁶ is halo, hydroxy, alkyl or haloalkyl; m is 0 or 1; R⁷ is fluoro, chloro, bromo, or methyl; n is 0, 1 or 2; R⁸ is hydroxy, aryl or heteroaryl, wherein aryl or heteroaryl are substituted with —NH₂ or —OH at a ring position adjacent to attachment of the —CONH-moiety, and R⁸ is optionally further substituted with one or more groups selected from amino, halo, alkyl, alkenyl, alkynyl, haloalkyl, cycloalkyl, heterocyclyl, aryl, haloaryl, haloheterocyclyl, wherein alkyl, alkenyl, or alkynyl is optionally further substituted with one or more groups selected from halo, hydroxy, alkyl, haloalkyl and cycloalkyl; and R⁹ is alkyl, haloalkyl, aminoalkyl, cycloalkyl, heterocyclyl or aryl, wherein R⁹ is optionally substituted by one or more D where such an optional substitution is chemically feasible.

In one embodiment, the invention provides a compound selected from those of of Formula (I$^c$) and a pharmaceutically acceptable salt thereof. In embodiments where X of Formula (I$^c$) is phenyl or thiophene, compounds include those of Formula (I$^c$-a) and Formula (I$^c$-b), respectively, as well as pharmaceutically acceptable salts:

Formula (I$^c$-a)

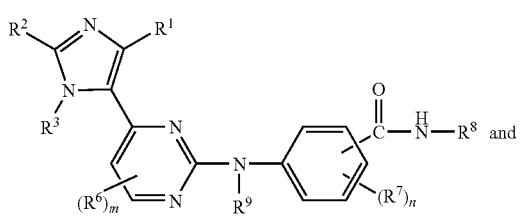

Formula (I$^c$-b)

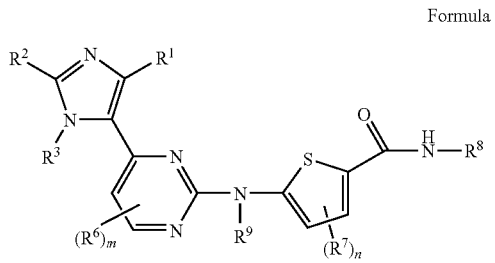

wherein m, n, R$^1$, R$^2$, R$^3$, R$^6$, R$^7$ and R$^8$ are as defined for various aspects of Formulae (I), (I$^a$) and (I$^b$) above; and R$^9$ is a non-hydrogen substituent selected from alkyl, haloalkyl, aminoalkyl, cycloalkyl, aryl, and heterocyclyl, wherein R$^9$ is optionally substituted by one or more D where such an optional substitution is chemically feasible.

In various embodiments of Formulae (I$^c$-a) and (I$^c$-b), the identity of groups R$^1$, R$^2$, R$^3$, R$^6$, R$^7$ and R$^8$ can be any of those described for the pyrimidine compounds of Formula (I$^a$-a); and R$^9$ is alkyl, haloalkyl or aminoalkyl. In particular, examples of compounds of Formulae (I$^c$-a) and (I$^c$-b) include those having the same combination or pattern of substituents given in the table for Compounds a-01 to a-38 wherein R$^9$ can be methyl, ethyl, trifluoromethyl or trifluoroethyl for each combination.

Compound Preparation

A compound of the present invention such as those of Formulae (I), (I$^a$), (I$^b$), and (I$^c$) can be prepared according to the schemes described below, but it shall be appreciated that modifications of the illustrated process or other process can also be used. Schemes A, B, and C illustrate a method to prepare a compound of Formula (I) from ketone compound 1 and guanidine compound 2.

Scheme A

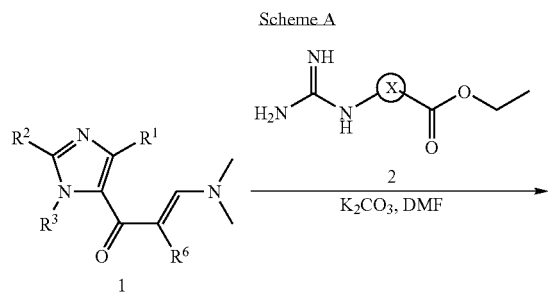

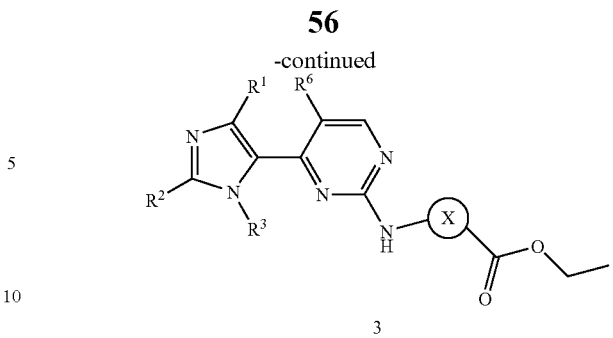

Ketone compound 1 is dissolved in a solvent such as dimethylformamide (DMF) to prepare a solution. Guanidine compound 2 containing an X aromatic group is added to the solution, and the mixture is refluxed. (For clarity, the group X in the synthetic schemes is given without the R$^7$ group that is optionally attached in the compounds.) The solid product is recovered and dried to yield compound 3, containing the pyrimidine ring formed from the reaction of 1 and 2.

In various embodiments, compound 3 is converted to hydroxamates or arylamides of Formula I. Scheme B below illustrates synthesis of hydroxamates, and scheme C illustrates synthesis of arylamides (where the group R$^8$ is a substituted aryl ring) from intermediate compound 3.

Scheme B

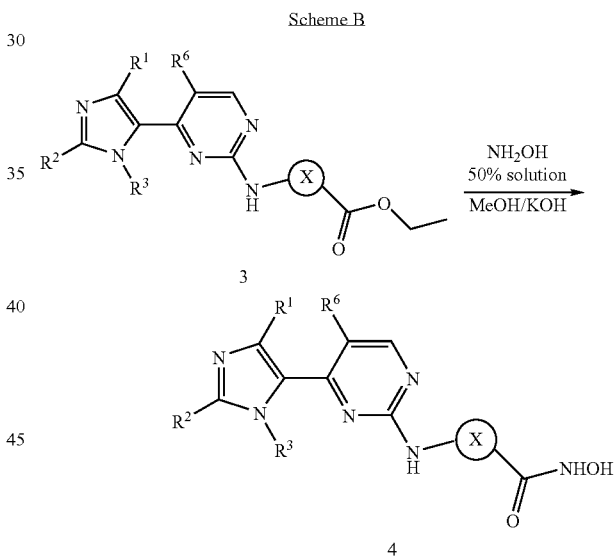

In an illustrative synthesis, compound 3 is dissolved in a solvent such as a mixture of methanol and dichloromethane and the mixture is stirred to prepare a solution. NH$_2$OH is added to the stirred solution slowly. After stirring, NaOH is added dropwise and brought to room temperature and stirred. The volatiles are evaporated under vacuum, diluted with water, and cooled. The pH of the solution is adjusted to about 7 using HCl and stirred. The resulting solid is filtered, washed with water and dried under vacuum to afford Compound 4 containing a hydroxamate group —NH$_2$OH.

In Scheme C, the intermediate ester compound 3 is converted to an arylamide compound, illustrated by compound 5, wherein T stands for NH$_2$ or OH (attached to the phenyl ring at a position adjacent to the —NHC(O)—X— moiety) and R$^{10}$ is selected from amino, halo, alkyl, cycloalkyl, heterocyclyl, aryl, haloaryl and haloheterocyclyl.

Scheme C

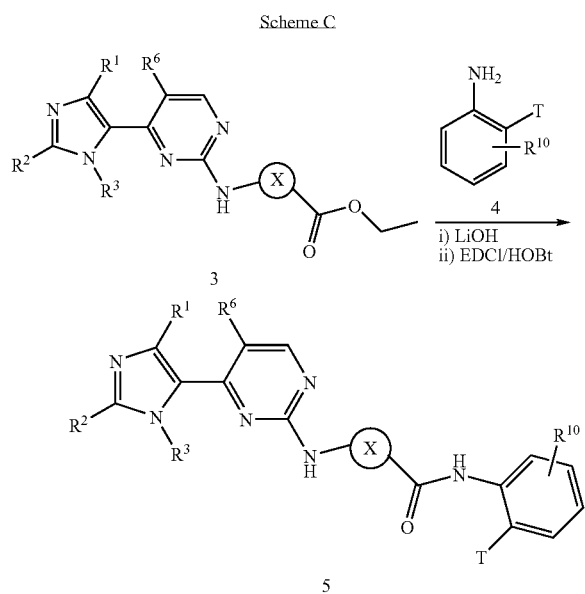

Ester compound 3 is converted to the free carboxylic acid, and is then reacted with substituted aniline 4 to yield an arylamide of formula 5. For example, LiOH is added to a stirred solution of compound 3 in a mixture of solvents. The volatiles are removed under vacuum, and the residue is diluted with water and acidified to about pH 3. The resulting solids are filtered, washed with water and dried under vacuum to furnish a carboxylic acid intermediate. The intermediate is dissolved in a solvent such as DMF and the mixture is stirred to prepare a solution. To the stirred solution is added 1-ethyl-3-(3'-dimethylaminopropyl)carbodiimide hydrochloride (EDCl) followed by hydroxybenzotriazole (HOBt). After stirring, diisopropyl ethyl amine is added and stirred. Then substituted aniline 4 (representative of substituted aryl or heteroaryl) is added, and the reaction mixture is stirred. The solvent is removed under vacuum. The residue is diluted with water and stirred. The resulting solids are filtered and purified through column chromatography to provide benzamide 5.

In various embodiments, the compounds of the present invention inhibit histone deacetylase and/or CDK and are useful to treat or ameliorate diseases mediated directly or indirectly by HDAC and/or CDK. Therefore, another aspect of the present invention is to provide a pharmaceutical composition comprising an effective amount of one or more compounds as described above.

In one embodiment of the invention, a pharmaceutical composition is provided comprising, in addition to one or more compounds described herein, at least one pharmaceutically-acceptable diluent, adjuvant, excipient, or carrier. The composition can take any suitable form for the desired route of administration. Where the composition is to be administered orally, any suitable orally deliverable dosage form can be used, including without limitation tablets, capsules (solid- or liquid-filled), powders, granules, syrups and other liquids, elixirs, inhalants, troches, lozenges, and solutions. Injectable compositions or iv infusions are also provided in the form of solutions, suspensions, and emulsions.

A pharmaceutical composition according to the present invention may contain one or more additional therapeutic agents, for example, to increase the efficacy or decrease the side effects. In some embodiments, accordingly, a pharmaceutical composition further contains one or more additional therapeutic agents selected from active ingredients useful to treat or inhibit diseases mediated directly or indirectly by HDAC and/or CDK. Examples of such active ingredients are, without limitation, agents to treat or inhibit cancer, Huntington's disease, cystic fibrosis, liver fibrosis, renal fibrosis, pulmonary fibrosis, skin fibrosis, Rheumatoid arthritis, diabetes, stroke, amyotrophic lateral sclerosis, cardiac hypertrophy, heart failure or Alzheimer's disease.

In an embodiment, an additional therapeutic agent to be included is an anti-cancer agent. Examples of an anti-cancer agent include, but are not limited to, alkylating agents such as cyclophosphamide, dacarbazine, and cisplatin; antimetabolites such as methotrexate, mercaptopurine, thioguanine, fluorouracil, and cytarabine; plant alkaloids such as vinblastine, and paclitaxel; antitumor antibiotics such as doxorubicin, bleomycin, and mitomycin; hormones/antihormones such as prednisone, tamoxifen, and flutamide; other types of anticancer agents such as asparaginase, rituximab, trastuzumab, imatinib, retinoic acid and derivatives, colony-stimulating factors, amifostine, camptothecin, topotecan, thalidomide analogs such as lenalidomide, CDK inhibitor and other HDAC inhibitor such as histone deacetylase 1 inhibitors, histone deacetylase 2 inhibitors, histone deacetylase 3 inhibitors, histone deacetylase 4 inhibitors, histone deacetylase 5 inhibitors, histone deacetylase 6 inhibitors, histone deacetylase 7 inhibitors, histone deacetylase 8 inhibitors, histone deacetylase 9 inhibitors, histone deacetylase 10 inhibitors, and histone deacetylase 11 inhibitors.

Yet another aspect of the present invention is to provide a method of inhibiting or treating diseases arising from abnormal cell proliferation and/or differentiation in animal, comprising administering to said animal a therapeutically effective amount of one or more compounds according to the present invention. In one embodiment, the method of inhibiting or treating disease comprises administering to an animal a composition comprising an effective amount of one or more compounds of the invention and a pharmaceutically-acceptable carrier. The composition to be administered may further contain a therapeutic agent such as anti-cancer agent.

A method of the present invention is particularly suitable for use with humans, but may be used with other animals, particularly mammals, such as, for example, non-human primates, companion animals, farm animals, laboratory animals, and wild and zoo animals.

A method of the present invention is particularly useful to treat diseases mediated directly or indirectly by HDAC and/or CDK since the compounds of the present invention have inhibitory activity against those molecules. In some embodiments, therefore, a method of the present invention is used in inhibiting or treating HDAC- and/or CDK-mediated diseases. Examples of such disease include, but are not limited to, cell proliferative diseases such as cancer, autosomal dominant disorders such as Huntington's disease, genetic related metabolic disorder such as cystic fibrosis, fibrosis such as liver fibrosis, renal fibrosis, pulmonary fibrosis and skin fibrosis, autoimmune diseases such as Rheumatoid arthritis, diabetes, acute and chronic neurological diseases such as stroke, amyotrophic lateral sclerosis, hypertrophy such as cardiac hypertrophy, heart failure including congestive heart failure, and Alzheimer's disease.

In an embodiment, a method according to the present invention is applied to a patient with cancer or fibrosis. In some embodiments, a method using a compound according to the present invention is used to treat or inhibit fibrosis selected from the group consisting of cystic fibrosis, injection fibrosis, endomyocardial fibrosis, pulmonary fibrosis, mediastinal fibrosis, myelofibrosis, retroperitoneal fibrosis, progressive massive fibrosis and renal fibrosis. In some other embodiments, a method using a compound according to the present invention is used to treat or inhibit a cancer selected from bladder cancer, breast cancer, colon and rectal cancer, endometrial cancer, kidney (renal cell) cancer, leukemia, lung cancer, melanoma, non-Hodgkin's lymphoma, pancreatic cancer, prostate cancer, skin cancer (non-melanoma), and thyroid cancer.

EXAMPLES

Further non-limiting description is provided in the following Examples.

Example 1

N-(2-amino-phenyl)-4-[4-(1-isopropyl-2-methylimidazol-5-yl)-pyrimidin-2-ylamino]-benzamide

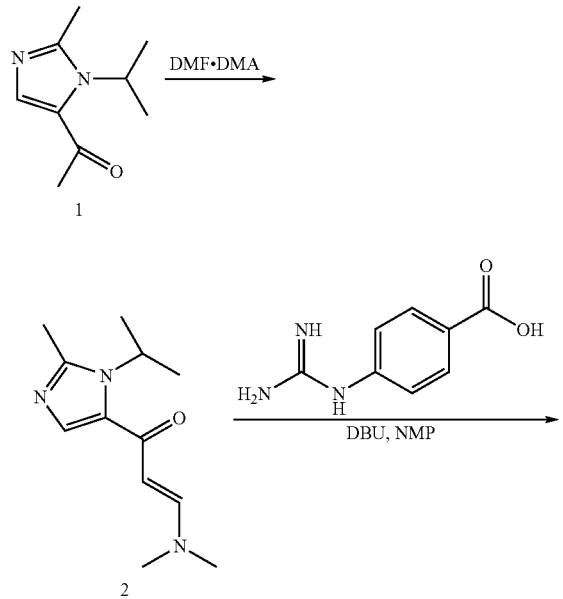

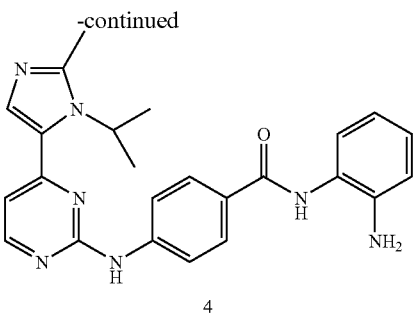

Example 1 (Compound a-02)

Preparation of Intermediate (hereinafter "Int") 3: A mixture of Int-1 (720 mg, 4.34 mmol) and N,N-dimethylformamide dimethyl acetal (DMF.DMA) (5 mL) was heated in microwave (Emry's Optimizer) at 160° C. After 4 hours, the reaction mixture was concentrated in vacuo and hexane (100 mL) was poured. The resulting solid was filtered and washed with hexanes and dried to give Int-2. MS found for $C_{12}H_{19}N_3O$ (m/z): 223.1 [M$^+$+1]. A mixture of Int-2 (222 mg, 1.0 mmol), 4-guanidinobenzoic acid hydrochloride (215 mg, 1.0 mmol) and 1,8-diazabicyclo[5.4.0]undec-7-ene (DBU) (0.3 mL, 2.0 mmol) in N-methyl-2-pyrrolidone (NMP) (4 mL) was heated in microwave (Emry's Optimizer) at 160° C. After 1 hour, the reaction mixture was diluted with water and acetonitrile and directly purified by preparative high performance liquid chromatography (HPLC) affording Int-3. MS found for $C_{18}H_{19}N_5O_2$ (m/z): 338.1 [M$^+$+1].

Preparation of Compound 4: To Int-3 (100 mg, 0.3 mmol) in NMP (4 mL), was added O-(7-azabenzotriazol-1-yl)-N,N,N',N'-tetramethyluronium hexafluorophosphate (HATU) (171 mg, 0.45 mmol), 1,2-phenylenediamine (65 mg, 0.6 mmol) and N-methylmorpholine (NMM) (0.1 mL, 0.9 mmol) and stirred for 30 minutes. The reaction mixture was diluted with water and acetonitrile and directly purified by preparative HPLC affording Compound 4 as tan solid, after lyophilization. MS found for $C_{24}H_{25}N_7$ as (M+H)$^+$ 428.6. $^1$H NMR (400 MHz, dmso-d$_6$): δ 10.01 (s, 1H); 9.59 (s, 1H); 8.64 (d, J=5.2 Hz, 1H); 8.09 (s, 1H); 7.92 (d, J=8.8 Hz, 2H); 7.79 (d, J=8.8 Hz, 2H); 7.16 (d, J=5.2 Hz, 1H); 7.13 (d, J=7.6 Hz, 6.97 (t, J=7.6 Hz, 1H); 6.81 (d, J=7.6 Hz, 1H); 6.62 (t, J=7.6 Hz, 1H); 5.59 (m, 1H); 3.28 (brs); 2.70 (s, 3H); 1.50 (d, J=6.8 Hz, 6H).

Example 2

N-hydroxy-4-[4-(1-isopropyl-2-methylimidazol-5-yl)-pyrimidin-2-ylamino]-benzamide

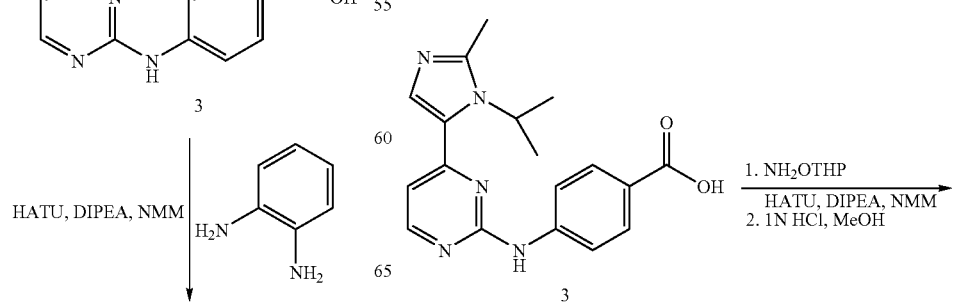

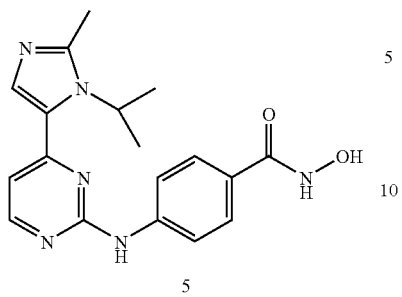

Example 2 (Compound a-01)

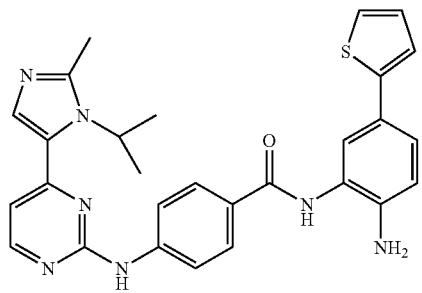

Example 3 (Compound a-35)

To Int-3 (146 mg, 0.43 mmol) in NMP (6 mL) were added HATU (247 mg, 0.65 mmol), O-(Tetrahydro-2H-pyran-2-yl) hydroxylamine (76 mg, 0.65 mmol) and NMM (0.15 mL, 1.3 mmol) and stirred. After 2 hours, additional O-(Tetrahydro-2H-pyran-2-yl)hydroxylamine (51 mg, 0.43 mmol), HATU (82 mg, 0.22 mmol) and NMM (0.1 mL) were added and stirred at room temperature for 1 hour. Then methanol (10 mL) and 1N HCl (12 mL) was added to the reaction mixture and stirred at room temperature for 1 hour. The reaction mixture was then diluted with water and acetonitrile and directly purified by preparative HPLC affording Compound 5 as tan solid, after lyophilization. MS found for $C_{18}H_{20}N_6O_2$ as $(M+H)^+$ 353.2. $^1$H NMR (400 MHz, dmso-$d_6$): δ 11.03 (s, 1H); 9.73 (s, 1H); 8.85 (s, 1H); 8.43 (d, J=5.2 Hz, 1H); 7.75 (d, J=8.8 Hz, 2H); 7.72 (d, J=8.8 Hz, 2H); 7.46 (s, 1H); 7.09 (d, J=5.2 Hz, 1H); 5.70 (m, 1H); 2.45 (s, 3H); 1.45 (d, J=6.8 Hz, 6H).

To Int-3 (75 mg, 0.3 mmol) in DMF (4 mL) were added HATU (110 mg, 0.29 mmol), tert-butyl 2-amino-4-(thiophen-2-yl)phenylcarbamate (84 mg, 0.29 mmol) and NMM (0.08 mL, 0.67 mmol) and stirred at room temperature. After 2 hours, additional tert-butyl 2-amino-4-(thiophen-2-yl)phenylcarbamate (65 mg, 0.22 mmol) and NMM (0.08 mL, 0.67 mmol) were added and stirred at room temperature. After 16 hours, the reaction mixture was concentrated in vacuo and 4.0 M HCl in dioxane (1 mL) was added and stirred at room temperature for 2 hours. The reaction mixture was then concentrated and diluted with water and acetonitrile and purified by preparative HPLC affording Compound 6, after lyophilization. MS found for $C_{28}H_{27}N_7OS$ as $(M+H)^+$ 510.1. $^1$H NMR (400 MHz, dmso-$d_6$): δ 9.81 (s, 1H); 9.58 (s, 1H); 8.46 (d, J=5.6 Hz, 1H); 7.93 (d, J=8.8 Hz, 2H); 7.84 (d, J=8.8 Hz, 2H); 7.50 (s, 1H); 7.44-7.33 (m, 1H); 7.33-7.21 (m, 3H); 7.12 (d, J=5.6 Hz, 1H); 7.03-7.00 (m, 1H); 6.79 (d, J=8.4 Hz, 1H); 5.73 (m, 1H); 2.50 (s, 3H); 1.49 (d, J=7.2 Hz, 6H).

Example 3

N-(2-amino-5-thiophen-2-yl-phenyl)-4-[4-(1-isopropyl-2-methylimidazol-5-yl)-pyrimidin-2-ylamino]-benzamide Example 4

N-(2-amino-5-fluoro-phenyl)-4-[4-(1-isopropyl-2-methylimidazol-5-yl)-pyrimidin-2-ylamino]-benzamide

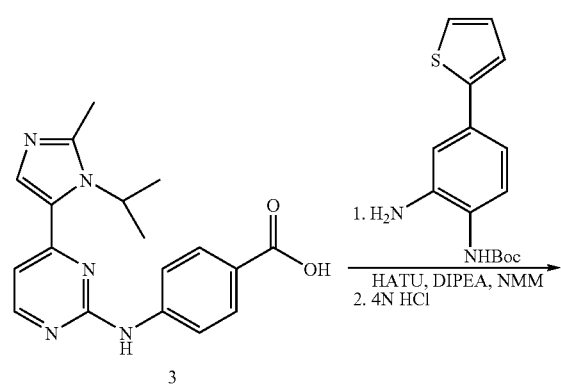

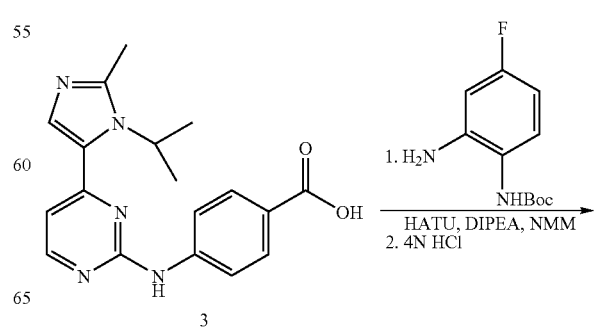

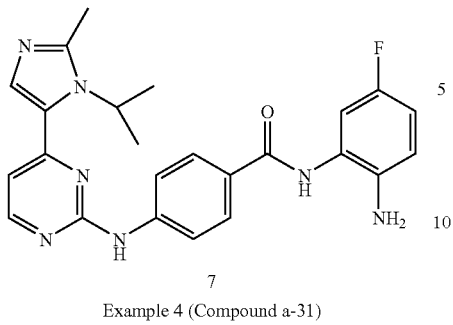

7

Example 4 (Compound a-31)

To Int-3 (100 mg, 0.3 mmol) in DMF (5 mL), were added HATU (169 mg, 0.44 mmol), tert-butyl 2-amino-4-fluorophenylcarbamate (134 mg, 0.59 mmol) and NMM (0.13 mL, 1.18 mmol) and stirred at room temperature. After 14 hours, additional tert-butyl 2-amino-4-fluorophenylcarbamate (335 mg, 1.4 mmol) and NMM (0.13 mL, 1.18 mmol) were added and stirred at room temperature. After 16 hours, the reaction mixture was concentrated in vacuo and 4.0 M HCl in dioxane (5 mL) was added and stirred at room temperature for 1 hour. The reaction mixture was then concentrated, diluted with water and acetonitrile, and purified by preparative HPLC affording Compound 7 after lyophilization. MS found for $C_{24}H_{24}FN_7O$ as $(M+H)^+$ 446.0. $^1H$ NMR (400 MHz, dmso-$d_6$): δ 9.81 (s, 1H); 9.49 (s, 1H); 8.46 (d, J=5.6 Hz, 1H); 7.92 (d, J=8.8 Hz, 2H); 7.83 (d, J=8.8 Hz, 2H); 7.49 (s, 1H); 7.15-7.11 (m, 2H); 6.79-6.74 (m, 2H); 5.71 (m, 1H); 2.50 (s, 3H); 1.49 (d, J=6.8 Hz, 6H).

Example 5

N-(2-aminophenyl)-4-(5-(1-isopropyl-2-methylimidazol-5-yl)-1,2,4-triazin-3-ylamino)benzamide

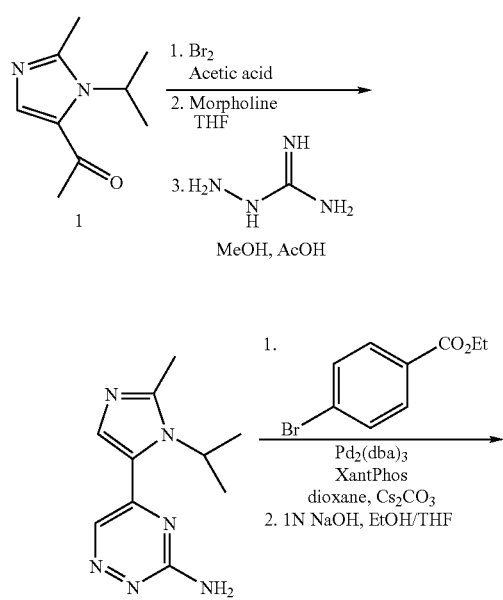

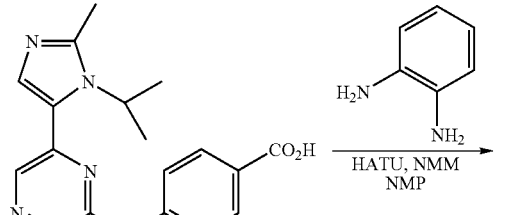

Example 5 (Compound $I^b$-g-2)

To the mixture of Int-1 (500 mg, 3.25 mmol) in acetic acid (5 mL) was added 1M solution of $Br_2$ in acetic acid (0.33 mL, 6.50 mmmol). After 2 hours at 100° C., reaction mixture was cooled to room temperature and concentrated, which was then washed with hexanes (100 mL) to give 2,2-dibromo-1-(3-isopropyl-2-methyl-3H-imidazol-4-yl)-ethanone which was used further without purification. To the above dibromide in tetrahydrofuran (THF) (5 mL) under $N_2$ was added morpholine (1.2 mL, 13.7 mmol) at room temperature and the resulting solution was heated to 67° C. After 96 hours, the reaction mixture was cooled to room temperature, the suspension was filtered through a funnel (M) and the solids were washed with THF (25 mL). The filtrate was then concentrated to give the crude aminal intermediate, which was used without further purification. The crude aminal was dissolved in MeOH (5 mL) and treated with aminoguanidine bicarbonate (442 mg, 3.25 mmol) and AcOH (0.6 mL, 9.75 mmol). The resulting suspension was stirred at room temperature for 2 hours. The resulting solution was then heated at 75° C. for 14 hours. The resulting dark brown solution was cooled to room temperature, concentrated, diluted with $H_2O$ and washed with heptane (50 mL). The aqueous layer was concentrated and diluted with water and acetonitrile and purified by preparative HPLC to give 5-(3-isopropyl-2-methyl-3H-imidazol-4-yl)-[1,2,4]triazin-3-ylamine after lyophilization. MS found for $C_{10}H_{14}N_6$ as $(M+H)^+$ 219.4.

A mixture of the above amino triazine (100 mg, 0.46 mmol), 4-bromo-benzoic acid ethyl ester (136 mg, 0.60 mmol), tris(dibenzylideneacetone)dipalladium(0) ($Pd_2(dba)_3$) (10 mg, 0.01 mmol), XantPhos (11 mg, 0.01 mmol) and $Cs_2CO_3$ (350 mg, 1.07 mmol) in dioxane (3 mL) was heated in microwave (Emry's Optimizer) at 120° C. After 30 minutes, the reaction mixture was concentrated to give 4-[5-(3-isopropyl-2-methyl-3H-imidazol-4-yl)-[1,2,4]triazin-3-ylamino]-benzoic acid ethyl ester which was used further without purification. MS found for $C_{19}H_{22}N_6O_2$ as $(M+H)^+$ 367.22. To the above crude ester in EtOH/THF (5:2) (7 mL) was added 1N NaOH (4.6 mL) and stirred at room temperature. After 12 hours, the reaction mixture was concentrated, diluted with water and washed with ether (3×). The aqueous phase was then neutralized with 1N HCl (6 mL) and the precipitated solid was filtered, washed with water and dried to give the acid which was used for the next step without purification. MS found for $C_{17}H_{18}N_6O_2$ as $(M+H)^+$ 339.08.

To the above carboxylic acid (130 mg, 0.39 mmol) in NMP (4 mL), was added HATU (234 mg, 0.62 mmol), 1,2-phenylenediamine (84 mg, 0.77 mmol) and NMM (0.2 mL, 1.54 mmol) and stirred at room temperature for 1 hour. The reaction mixture was then diluted with water and acetonitrile and directly purified by preparative HPLC affording the title compound as tan solid, after lyophilization. MS found for $C_{23}H_{24}N_8O$ as $(M+H)^+$ 429.02. $^1$H NMR (400 MHz, dmso-$d_6$): δ 10.37 (s, 1H); 9.69 (s, 1H); 9.21 (s, 1H); 8.27 (s, 1H); 8.04 (d, J=8.4 Hz, 2H); 7.82 (d, J=8.4 Hz, 2H); 7.17 (d, J=7.6 Hz, 1H); 7.04 (m, 1H); 6.85 (d, J=7.6 Hz, 1H); 6.69 (m, 1H); 5.77 (m, 1H); 2.67 (s, 3H); 1.53 (d, J=7.2 Hz, 6H).

Example 6

N-(2-amino-5-(trifluoromethyl)phenyl)-4-(4-(1-isopropyl-2-methylimidazol-5-yl)pyrimidin-2-ylamino)benzamide

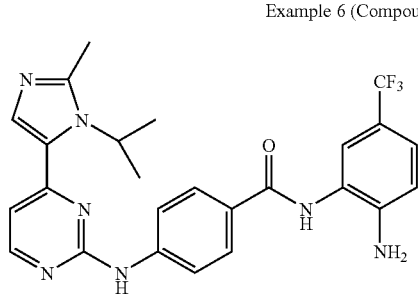

Example 6 (Compound I$^a$-a-33)

Similar procedure from Example 3 was followed to obtain the title compound using tert-butyl 2-amino-4-trifluoromethylphenylcarbamate. $C_{25}H_{24}F_3N_7O$ 496.05 (M+1). $^1$H NMR (400 MHz, dmso-$d_6$): δ 9.79 (s, 1H); 9.54 (s, 1H); 8.44 (d, J=5.2 Hz, 1H); 7.94 (d, J=8.8 Hz, 2H); 7.84 (d, J=8.8 Hz, 2H); 7.47 (m, 2H); 7.25 (d, J=8.8 Hz, 1H); 7.12 (d, J=5.6 Hz, 1H); 6.85 (d, J=8.4 Hz, 1H); 5.75 (m, 1H); 5.61 (brs, 2H); 2.49 (s, 3H); 1.48 (d, J=6.8 Hz, 6H).

Example 7

N-(2-amino-5-(thiophen-2-yl)phenyl)-4-(5-(1-isopropyl-2-methylimidazol-5-yl)-1,2,4-triazin-3-ylamino)benzamide

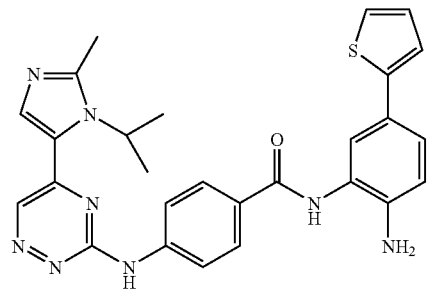

Example 7 (Compound I$^b$-g-35)

Similar procedure from Example 5 was followed to obtain the title compound using tert-butyl 2-amino-4-(thiophen-2-yl)phenylcarbamate. $C_{27}H_{26}N_8OS$ 511.04 (M+1). $^1$H NMR (400 MHz, dmso-$d_6$): δ 10.12 (s, 1H); 9.63 (s, 1H); 9.18 (s, 1H); 8.00 (d, J=8.4 Hz, 2H); 7.91 (s, 1H); 7.83 (d, J=8.4 Hz, 2H); 7.44 (d, J=2.4 Hz, 1H); 7.33-7.21 (m, 3H); 7.03 (m, 1H); 6.80 (d, J=8.4 Hz, 1H); 5.83 (m, 1H); 5.01 (brs, 2H); 2.52 (s, 3H); 1.50 (d, J=7.2 Hz, 6H).

Example 8

N-hydroxy-5-(4-(1-isopropyl-2-methylimidazol-5-yl)pyrimidin-2-ylamino)thiophene-2-carboxamide

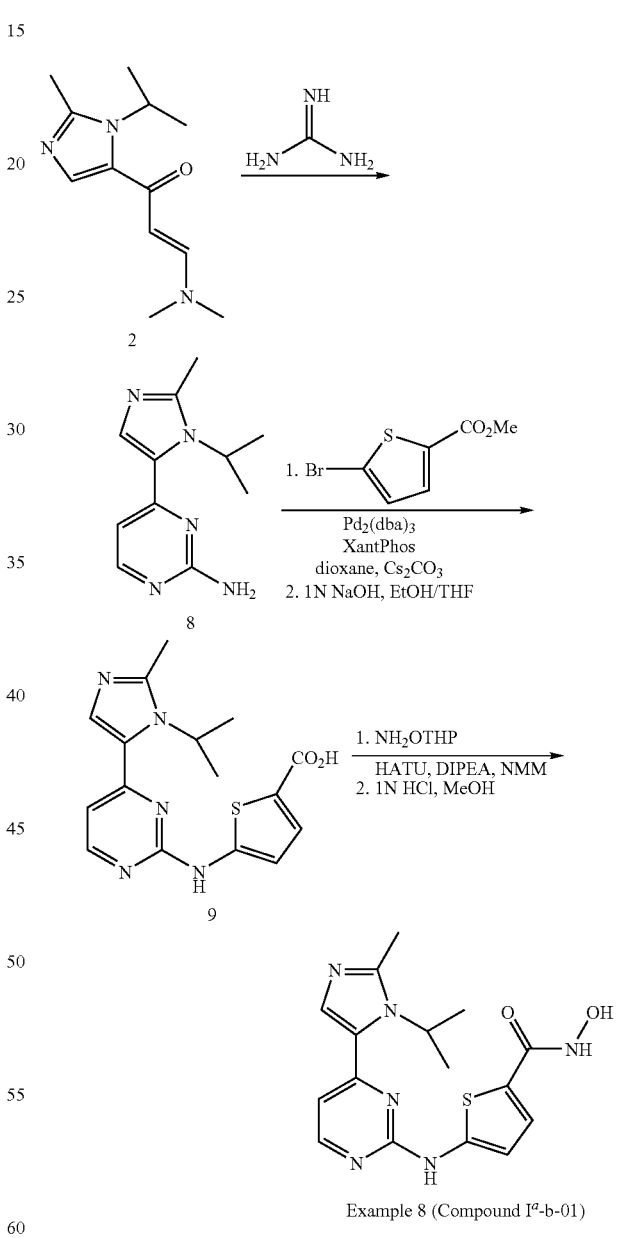

Example 8 (Compound I$^a$-b-01)

A mixture of Int-2 (439 mg, 1.97 mmol) and guanidine carbonate (791 mg, 4.39 mmol) in 2-methoxyethanol (8 mL) was heated in microwave (Emry's Optimizer) at 160° C. After 30 minutes, the reaction mixture was diluted with water and extracted with dichloromethane (DCM) (3×40 mL) and the combined DCM layers were dried (MgSO$_4$). Filtration and concentration gave Int-8 which was used for the next step without purification. MS found for $C_{11}H_{15}N_5$ as $(M+H)^+$ 218.10.

A mixture of the Int-8 (217 mg, 1 mmol), 5-bromothiophene-2-carboxylic acid methyl ester (332 mg, 1.5 mmol), $Pd_2(dba)_3$ (18 mg, 0.02 mmol), XantPhos (29 mg, 0.05 mmol) and $Cs_2CO_3$ (488 mg, 1.5 mmol) in dioxane (5 mL) was heated in a pressure vessel at 130° C. After 13 hours, the reaction mixture was concentrated to give the coupled product which was used further without purification. MS found for $C_{17}H_{19}N_5O_2S$ as $(M+H)^+$ 358.31. To the above crude ester in MeOH/THF (8:3) (11 mL) was added 3N NaOH (3.0 mL) and stirred at 60° C. After 48 hours, the reaction mixture was concentrated, diluted with water and washed with ether (3×). The aqueous phase was then neutralized with 6N HCl (1.5 mL) and the precipitated solid was filtered, washed with water and dried to give Int-9, which was used for the next step without purification. MS found for $C_{16}H_{17}N_5O_2S$ as $(M+H)^+$ 344.16.

To Int-9 (91 mg, 0.27 mmol) in DMF (3 mL), was added HATU (151 mg, 0.39 mmol), O-(tetrahydro-2H-pyran-2-yl) hydroxylamine (62 mg, 0.53 mmol) and NMM (0.1 mL, 0.8 mmol) and stirred. After 24 hours, additional O-(tetrahydro-2H-pyran-2-yl)hydroxylamine (62 mg, 0.53 mmol), HATU (151 mg, 0.39 mmol) and NMM (0.1 mL) was added and stirred at room temperature for 48 hours. Then methanol (5 mL) and 1N HCl (5.2 mL) was added to the reaction mixture and stirred at room temperature for 24 hours. The reaction mixture was then concentrated and then diluted with water and acetonitrile and directly purified by preparative HPLC affording the title compound, after lyophilization. MS found for $C_{16}H_{18}N_6O_2S$ as $(M+H)^+$ 359.04. $^1$H NMR (400 MHz, dmso-$d_6$): δ 10.84 (brs, 2H); 8.89 (brs, 1H); 8.47 (d, J=5.2 Hz, 1H); 7.45 (m, 2H); 7.10 (d, J=5.6 Hz, 1H); 6.66 (d, J=4.0 Hz, 1H); 5.68 (m, 1H); 2.48 (s, 3H); 1.48 (d, J=7.2 Hz, 6H).

Example 9

N-(4-amino-4'-fluorobiphenyl-3-yl)-4-(4-(1-isopropyl-2-methylimidazol-5-yl)pyrimidin-2-ylamino) benzamide Example 9 (Compound I$^a$-a-40)

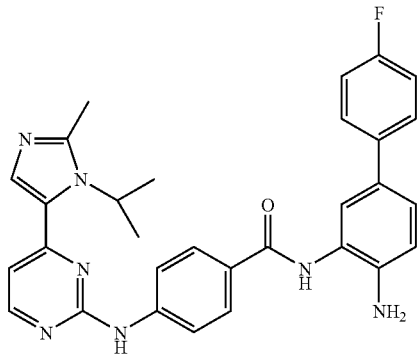

Similar procedure from Example 3 was followed to obtain the title compound using (3-amino-4'-fluoro-biphenyl-4-yl)-carbamic acid tert-butyl ester instead of tert-butyl 2-amino-4-(thiophen-2-yl)phenylcarbamate. MS found for $C_{30}H_{28}FN_7O$ as $(M+H)^+$ 522.04. $^1$H NMR (400 MHz, dmso-$d_6$): δ 9.81 (s, 1H); 9.55 (s, 1H); 8.46 (d, J=5.6 Hz, 1H); 7.93 (d, J=8.8 Hz, 2H); 7.80 (d, J=8.8 Hz, 2H); 7.55-7.42 (m, 3H); 7.24-7.14 (m, 5H); 6.81 (d, J=8.0 Hz, 1H); 5.66 (m, 1H); 2.50 (s, 3H); 1.46 (d, J=6.8 Hz, 6H).

Example 10

N-(2-amino-5-(thiophen-2-yl)phenyl)-5-(4-(1-isopropyl-2-methylimidazol-5-yl)pyrimidin-2-ylamino) thiophene-2-carboxamide Example 10 (Compound 1$^a$-b-35)

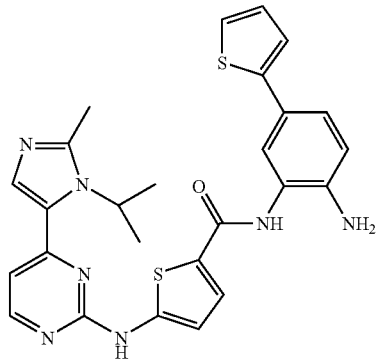

Similar procedure from Example 8 was followed to obtain the title compound using Int-9 and (2-amino-4-thiophen-2-yl-phenyl)-carbamic acid tert-butyl ester. MS found for $C_{26}H_{25}N_7S_2O$ as $(M+H)^+$ 515.95. $^1$NMR (400 MHz, dmso-$d_6$): δ 11.19 (brs, 1H); 9.51 (s, 1H); 8.69 (d, J=5.2 Hz, 1H); 8.07 (s, 1H); 7.77 (d, J=4.0 Hz, 1H); 7.36-7.16 (m, 4H); 6.99 (t, J=5.2 Hz, 1H); 6.75 (m, 2H); 5.58 (m, 1H); 2.69 (s, 3H); 1.52 (d, J=6.8 Hz, 6H).

Example 11

N-(2-aminophenyl)-5-(4-(1-isopropyl-2-methylimidazol-5-yl)pyrimidin-2-ylamino)thiophene-2-carboxamide Example 11 (Compound 1$^a$-b-04)

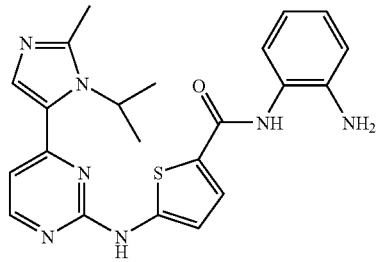

Similar procedure from Example 8 was followed to obtain the title compound using Int-9 and 1,2-phenylenediamine. MS found for $C_{22}H_{23}N_7SO$ as $(M+H)^+$ 434.03. $^1$H NMR (400 MHz, dmso-$d_6$): δ 10.92 (brs, 1H); 9.38 (s, 1H); 8.48 (d, J=5.6 Hz, 1H); 8.06 (s, 1H); 7.72 (d, J=4.0 Hz, 1H); 7.51 (s, 1H);

7.09-7.05 (m, 2H); 6.91 (t, J=8 Hz, 1H); 6.71 (m, 1H); 6.53 (t, J=8 Hz, 1H); 5.68 (m, 1H); 2.48 (s, 3H); 1.48 (d, J=7.2 Hz, 6H).

Example 12

N-(2-aminophenyl)-4-(4-(1-isopropyl-2-methylimidazol-5-yl)-1,3,5-triazin-2ylamino)benzamide

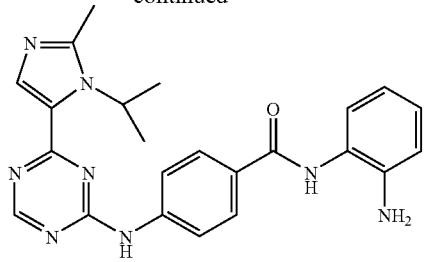

Example 12 (Compound $I^b$-f-02)

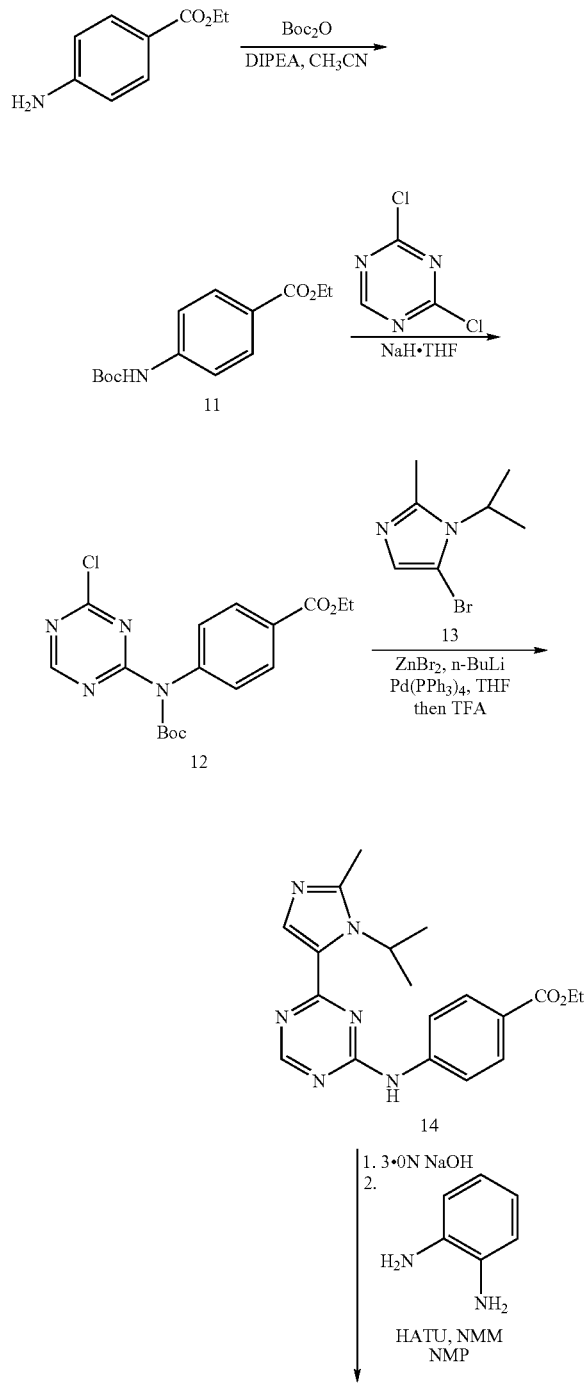

To a solution of 4-aminobenzoic acid ethyl ester (6.6 g, 40.25 mmol) in acetonitrile (35 mL) and N,N-diisopropylethylamine (DIPEA) (14 mL, 80.5 mmol), di-tert-butyl carbonate (17.5 g, 80.5 mmol) in acetonitrile (30 mL) was added and stirred at 70° C. After 48 hours, the reaction mixture was cooled to room temperature and the resulting solid was filtered and washed with acetonitrile and dried. $^1$H NMR (400 MHz, CDCl$_3$): δ 7.96 (d, J=8.8 Hz, 2H); 7.41 (d, J=8.8 Hz, 2H); 6.65 (s, 1H); 4.35 (q, J=7.6 Hz, 2H); 1.51 (s, 9H); 1.36 (t, J=7.2 Hz, 3H). To a suspension of NaH (60%, 392 mg, 9.8 mmol) in THF (5 mL) at 0° C., 4-tert-butoxycarbonylaminobenzoic acid ethyl ester (1 g, 3.92 mmol) in THF (20 mL) was added. After 5 minutes at 0° C., the ice bath was removed and the reaction mixture was stirred at room temperature for 1 hour. Then 2,4-dichloro-[1,3,5]triazine (1 g, 6.7 mmol) was added and stirred at room temperature. After 16 hours, the reaction mixture was diluted with water and extracted with ethyl acetate (3×). The combined ethyl acetate layers were washed with brine and dried (MgSO$_4$). Filtration and concentration followed by purification [Flash Chromatography (SiO$_2$, 2:8/EtOAc:Hexanes)] gave Int-12. MS found for C$_{17}$H$_{19}$ClN$_4$O$_4$ as (M+H)$^+$ 378.81. $^1$H NMR (400 MHz, CDCl$_3$): δ 8.69 (s, 1H); 8.12 (d, J=8.4 Hz, 2H); 7.25 (d, J=8.4 Hz, 4.39 (q, J=6.8 Hz, 2H); 1.44 (s, 9H); 1.36 (t, J=6.8 Hz, 3H).

To a solution of 1-isopropyl-2-methyl-1H-imidazole (3.4 g, 27.4 mmol) [prepared from 2-methylimidazole and 2-iodopropane in DMF with K$_2$CO$_3$ as base. MS found for C$_7$H$_{12}$N$_2$ as (M+H)$^+$ 125.06. $^1$H NMR (400 MHz, CDCl$_3$): δ 6.84 (d, J=1.2 Hz, 1H); 6.82 (d, J=1.2 Hz, 1H); 4.23 (septet, J=6.8 Hz, 1H); 2.31 (s, 3H); 1.36 (d, J=6.8 Hz, 3H); $^{13}$C NMR (400 MHz, CDCl$_3$): δ 143.52, 127.06, 114.62, 47.26, 23.26, 13.10] in isopropyl acetate (70 mL) was added K$_2$CO$_3$ (757 mg, 5.48 mmol) and stirred at room temperature for 5 minutes. Then N-bromosuccinimide (NBS) (4.4 g, 24.67 mmol) was slowly added in three portions (over 30 minutes). After 1 hour, the reaction was quenched with water (15 mL). The organic layer was separated and then washed with aqueous K$_2$CO$_3$ (50 mL) solution. The aqueous layer was then back extracted with isopropyl acetate (3×) and the combined organic layers were washed with brine and dried (MgSO$_4$). Filtration and concentration followed by purification [Flash Chromatography (SiO$_2$, 97:3/EtOAc:Methanol)] gave Int-13. MS found for C$_7$H$_{11}$BrN$_2$ as (M+H)$^+$ 204.92. $^1$H NMR (400 MHz, CDCl$_3$): δ 6.79 (s, 1H); 4.53 (septet, J=7.2 Hz, 1H); 2.41 (s, 3H); 1.48 (d, J=7.2 Hz, 3H).

To a solution of 5-bromo-1-isopropyl-2-methyl-1H-imidazole (355 mg, 1.76 mmol) in dry THF (8 mL) under N$_2$ at −78° C. was added n-BuLi (2.5 M in hexanes, 0.8 mL, 1.98 mmol) and the reaction mixture was stirred at that temperature for 1 hour. Then freshly dried zinc bromide (446 mg, 1.98 mmol) in dry THF (10 mL) was added. The reaction mixture was slowly warmed up to room temperature and Int-12 (500 mg, 1.32 mmol) and Pd(PPh₃)₄ (76 mg, 0.7 mmol) were added. After heating for 12 hours at 70° C., the reaction mixture was cooled to room temperature and concentrated. It was then diluted with ethyl acetate and washed with saturated NaHCO₃, brine, and then dried (MgSO₄). Filtration and concentration gave 4-{tert-butoxycarbonyl-[4-(3-isopropyl-2-methyl-3H-imidazol-4-yl)-[1,3,5]triazin-2-yl]-amino}-benzoic acid ethyl ester, which was used for the next step without purification. MS found for $C_{24}H_{30}N_6O_4$ as (M+H)⁺ 467.38. The above butoxycarbonyl (Boc) compound was dissolved in DCM (20 mL) and treated with trifluoroacetic acid (TFA) (5 mL) and stirred at room temperature for 10 minutes. The reaction mixture was then diluted with DCM and washed with saturated NaHCO₃, brine, and then dried (MgSO₄). Filtration and concentration gave 4-[4-(3-isopropyl-2-methyl-3H-imidazol-4-yl)-[1,3,5]triazin-2-ylamino]-benzoic acid ethyl ester which was used for the next step without purification. MS found for $C_{19}H_{22}N_6O_2$ as (M+H)⁺ 367.31.

To the above ester in EtOH/THF (10:3) (13 mL) was added 3N NaOH (4.5 mL) and stirred at room temperature. After 14 hours, the reaction mixture was concentrated, diluted with water and washed with ether (30 mL). The aqueous phase was then neutralized with 6N HCl (1.5 mL) and then extracted with ethyl acetate and dried (MgSO₄). The mixture was then filtered, concentrated and diluted with water and acetonitrile and directly purified by preparative HPLC giving 4-[4-(3-isopropyl-2-methyl-3H-imidazol-4-yl)-[1,3,5]triazin-2-ylamino]-benzoic acid. MS found for $C_{17}H_{18}N_6O_2$ as (M+H)⁺ 339.06. To the above carboxylic acid (150 mg, 0.4 mmol) in NMP (3 mL), was added HATU (228 mg, 0.60 mmol), 1,2-phenylenediamine (95 mg, 0.90 mmol) and NMM (0.2 mL, 1.60 mmol) and stirred for 16 hours. The reaction mixture was diluted with water and acetonitrile and directly purified by preparative HPLC affording the title compound, after lyophilization. MS found for $C_{23}H_{24}N_8O$ as (M+H)⁺ 429.09. ¹H NMR (400 MHz, dmso-d₆): δ 9.85 (s, 1H); 9.21 (s, 1H); 8.85 (s, 1H); 8.30 (s, 1H); 7.99 (d, J=8.4 Hz, 2H); 7.79 (m, 2H); 7.21 (d, J=7.6 Hz, 1H); 7.08-6.84 (m, 3H); 5.89 (septet, J=6.8 Hz, 1H); 2.71 (s, 3H); 1.53 (d, J=6.8 Hz, 6H).

Example 13

N-(4-amino-4'-fluorobiphenyl-3-yl)-5-(4-(1-isopropyl-2-methylimidazol-5-yl)pyrimidin-2-ylamino)thiophene-2-carboxamide Example 13 (Compound I^a-b-33)

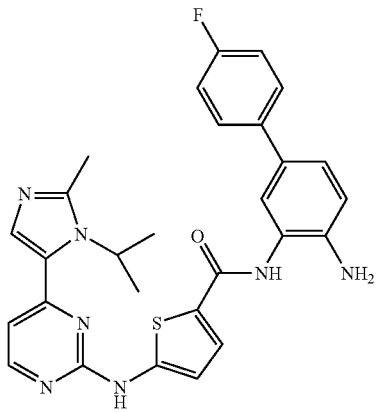

Similar procedure from Example 8 was followed to obtain the title compound using Int-9 and (3-amino-4'-fluoro-biphenyl-4-yl)-carbamic acid tert-butyl ester. MS found for $C_{28}H_{26}N_7FOS$ as (M+H)⁺ 528.00. ¹H NMR (400 MHz, dmso-d₆): δ 10.90 (brs, 1H); 8.46 (d, J=5.2 Hz, 1H); 8.09 (s, 1H); 7.75 (d, J=4.4 Hz, 1H); 7.53-7.37 (m, 3H); 7.23-7.07 (m, 4H); 6.80 (d, J=8.4 Hz, 1H); 6.72 (d, J=4.0 Hz, 1H); 5.68 (m, 1H); 4.99 (brs, 2H); 2.44 (s, 3H); 1.46 (d, J=6.8 Hz, 6H).

Example 14

N-(4-amino-4'-fluorobiphenyl-3-yl)-5-(4-(1-isopropyl-2-methylimidazol-5-yl)pyrimidin-2-ylamino)-4-methylthiophene-2-carboxamide

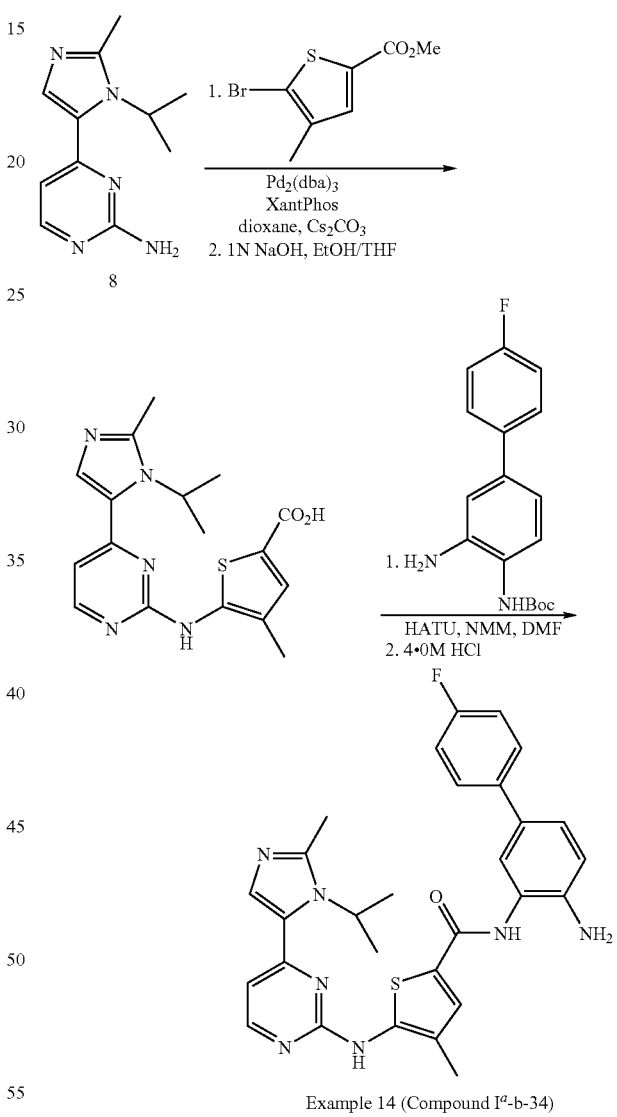

Example 14 (Compound I^a-b-34)

A mixture of Int-8 (434 mg, 2 mmol), 5-bromo-4-methyl-thiophene-2-carboxylic acid methyl ester (705 mg, 3.0 mmol), Pd₂(dba)₃ (37 mg, 0.04 mmol), XantPhos (58 mg, 0.1 mmol) and Cs₂CO₃ (1.4 g, 4.4 mmol) in dioxane (12 mL) was heated in a pressure vessel at 130° C. After 13 hours, the reaction mixture was cooled to room temperature, diluted with THF, and filtered. The filtrate was concentrated and purified by Flash Chromatography (SiO₂, 9:1:0.2/DCM: MeOH:triethylamine(TEA)) to give 5-[4-(3-isopropyl-2-methyl-3H-imidazol-4-yl)-pyrimidin-2-ylamino]-4-methylthiophene-2-carboxylic acid methyl ester. MS found for $C_{18}H_{21}N_5O_2S$ as $(M+H)^+$ 372.28.

To the above ester in MeOH/THF (10:5) (15 mL) was added 3N NaOH (5.0 mL) and stirred at 60° C. After 14 hours. The reaction mixture was concentrated, diluted with water and washed with ether (30 mL). The aqueous phase was then neutralized with 6 N HCl (1.5 mL), extracted with ethyl acetate, and then dried ($MgSO_4$). Filtration and concentration gave the acid which was used further without purification. MS found for $C_{17}H_{19}N_5O_2S$ as $(M+H)^+$ 358.24. To the above acid (70 mg, 0.2 mmol) in DMF (2 mL), was added HATU (114 mg, 0.3 mmol), (3-amino-4'-fluoro-biphenyl-4-yl)-carbamic acid tert-butyl ester (118 mg, 0.4 mmol) and NMM (0.1 mL, 0.78 mmol) and stirred at 50° C. for 16 hours. The reaction mixture was diluted with water and acetonitrile. The resulting solid was filtered, washed with water, and dried to give [4'-fluoro-3-({5-[4-(3-isopropyl-2-methyl-3H-imidazol-4-yl)-pyrimidin-2-ylamino]-4-methyl-thiophene-2-carbonyl}-amino)-biphenyl-4-yl]-carbamic acid tert-butyl ester. MS found for $C_{34}H_{36}FN_7O_3S$ as $(M+H)^+$ 642.02.

To the above Boc protected compound was added 4.0 M HCl dioxane (8.0 mL) and stirred at room temperature for 30 minutes. The reaction mixture was then concentrated and diluted with water and acetonitrile and directly purified by preparative HPLC. Lyophilization followed to give the title compound. MS found for $C_{29}H_{28}N_7FOS$ as $(M+H)^+$ 541.93. $^1H$ NMR (400 MHz, dmso-$d_6$): δ 9.67 (brs, 1H); 9.47 (s, 1H); 8.39 (d, J=5.2 Hz, 1H); 8.08 (s, 1H); 7.66 (s, 1H); 7.52-7.48 (m, 2H); 7.38 (m, 2H); 7.22-7.12 (m, 3H); 7.05 (d, J=5.2 Hz, 1H); 6.79 (d, J=8.4 Hz, 1H); 5.69 (m, 1H); 2.43 (s, 3H); 2.15 (s, 3H); 1.36 (d, J=6.8 Hz, 6).

Example 15

N-(4-amino-4'-fluorobiphenyl-3-yl)-2-(4-(1-isopropyl-2-methylimidazol-5-yl)pyrimidin-2-ylamino)thiazole-5-carboxamide

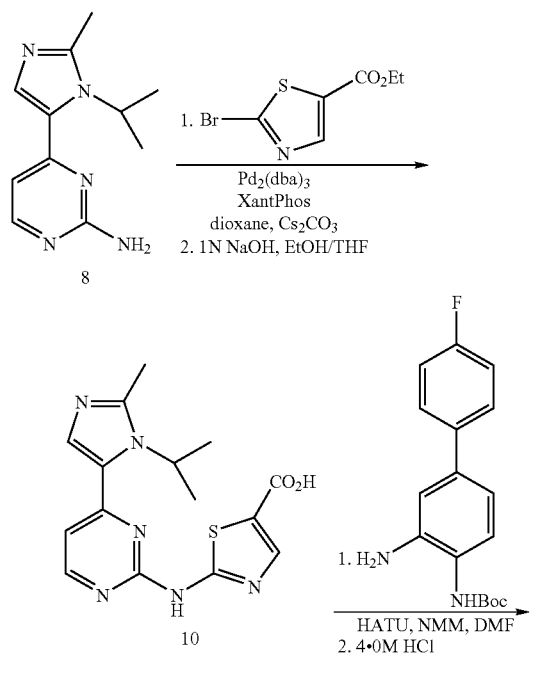

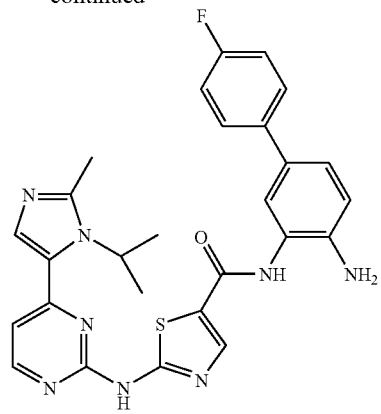

Example 15 (Compound I$^a$-c-33)

A mixture of the Int-8 (434 mg, 2 mmol), 2-bromo-thiazole-5-carboxylic acid ethyl ester (708 mg, 3.0 mmol), $Pd_2(dba)_3$ (37 mg, 0.04 mmol), XantPhos (58 mg, 0.1 mmol) and $Cs_2CO_3$ (1.4 g, 4.4 mmol) in dioxane (12 mL) was heated in a pressure vessel at 130° C. After 13 hours, the reaction mixture was cooled to room temperature, diluted with THF (30 mL), and filtered. The filtrate was concentrated and purified by Flash Chromatography ($SiO_2$, 9:1:0.2/DCM:MeOH:TEA) to give 2-[4-(3-isopropyl-2-methyl-3H-imidazol-4-yl)-pyrimidin-2-ylamino]-thiazole-5-carboxylic acid ethyl ester. MS found for $C_{17}H_{20}N_6O_2S$ as $(M+H)^+$ 373.30. To the above ester in EtOH/THF (10:5) (15 mL) was added 3N NaOH (6.0 mL) and stirred at 55° C. After 14 hours, the reaction mixture was concentrated, diluted with water and washed with ether (30 mL). The aqueous phase was then neutralized with 6N HCl (3.0 mL). The solids formed were filtered, washed with water, and dried. MS found for $C_{15}H_{16}N_6O_2S$ as $(M+H)^+$ 345.06. The acid was used further without purification.

To the above acid (212 mg, 0.62 mmol) in NMP (3 mL), was added HATU (351 mg, 0.92 mmol), (3-amino-4'-fluoro-biphenyl-4-yl)-carbamic acid tert-butyl ester (372 mg, 1.23 mmol) and NMM (0.3 mL, 2.5 mmol) and stirred at 50° C. for 16 hours. The reaction mixture was diluted with water and acetonitrile. The resulting solid was filtered, washed with water, and dried to give [4'-fluoro-3-({2-[4-(3-isopropyl-2-methyl-3H-imidazol-4-yl)-pyrimidin-2-ylamino]-thiazole-5-carbonyl}-amino)-biphenyl-4-yl]-carbamic acid tert-butyl ester. MS found for $C_{32}H_{33}FN_8O_3S$ as $(M+H)^+$ 629.23.

To the above Boc protected compound was added 4.0 M HCl in dioxane (10.0 mL). The reaction mixture was stirred at room temperature for 30 minutes. The reaction mixture was then concentrated and diluted with water and acetonitrile and directly purified by preparative HPLC. Lyophilization followed to give the title compound. MS found for $C_{27}H_{25}N_8FOS$ as $(M+H)^+$ 529.05. $^1$NMR (400 MHz, dmso-$d_6$): δ 12.01 (s, 1H); 9.58 (s, 1H); 8.54 (d, J=5.2 Hz, 1H); 8.23 (s, 1H); 7.53 (m, 3H); 7.39 (s, 1H); 7.26-7.13 (m, 4H); 6.80 (d, J=5.2 Hz, 5.78 (m, 1H); 5.06 (s, 2H); 2.45 (s, 3H); 1.44 (d, J=7.2 Hz, 6H).

Example 16

N-(2-amino-5-(thiophen-2-yl)phenyl)-2-(4-(1-iso-propyl-2-methylimidazol-5-yl)pyrimidin-2-ylamino)thiazole-5-carboxamide Example 16 (Compound 1$^a$-c-32)

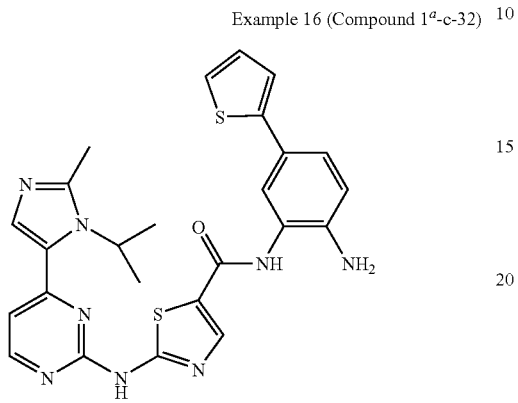

Similar procedure from Example 15 was followed to obtain the title compound using Int-10 and (2-amino-4-thiophen-2-yl-phenyl)-carbamic acid tert-butyl ester. MS found for $C_{25}H_{24}N_8S_2O$ as $(M+H)^+$ 516.89. $^1H$ NMR (400 MHz, dmso-$d_6$): δ 12.01 (brs, 1H); 9.59 (s, 1H); 8.54 (d, J=5.2 Hz, 1H); 8.23 (s, 1H); 7.53 (s, 1H); 7.37-7.18 (m, 5H); 6.75 (d, J=8.4 Hz, 1H); 5.81 (m, 1H); 5.12 (brs, 2H); 2.45 (s, 3H); 1.44 (d, J=7.2 Hz, 6H).

Example 17

N-(2-amino-5-(thiophen-2-yl)phenyl)-5-(5-fluoro-4-(1-isopropyl-2-methylimidazol-5-yl)pyrimidin-2-ylamino)thiophene-2-carboxamide

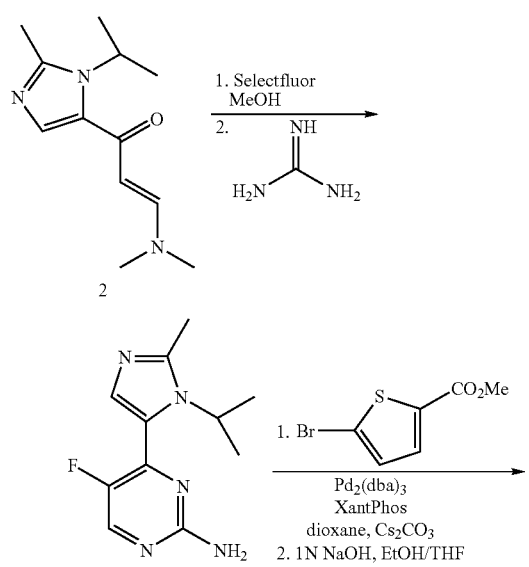

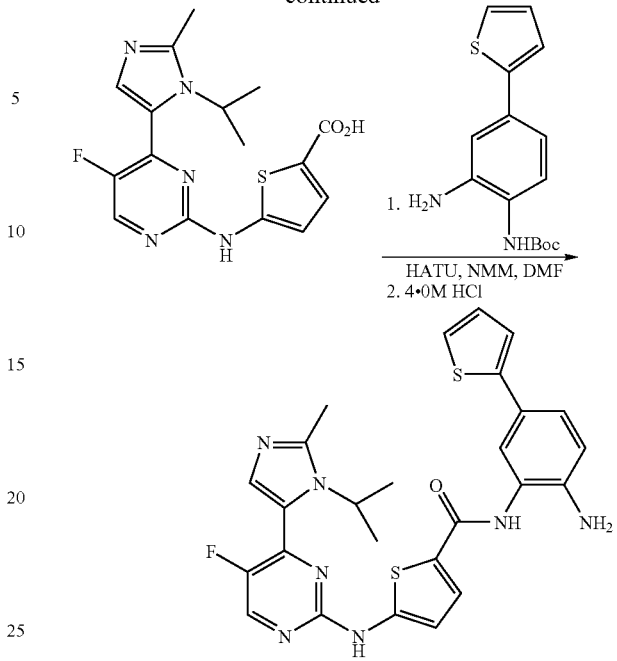

Example 17 (Compound I$^a$-b-36)

To a solution of Int-2 (640 mg, 2.88 mmol) in methanol (10 mL) at −78° C., Selectfluor (1.52 g, 4.3 mmol) was added. The reaction mixture was stirred at −78° C. for 30 minutes and then warmed up to room temperature. After 16 hours, ammonium hydroxide solution (3 mL) was added and stirred. The reaction mixture was then diluted with DCM and dried (MgSO$_4$). Filtration and concentration gave a brown solid, which was then treated with DCM (70 mL) and stirred. Insolubles were filtered and the filtrate was concentrated and purified by Flash Chromatography (SiO$_2$, 10:90/MeOH:DCM) to give 3-dimethylamino-2-fluoro-1-(3-isopropyl-2-methyl-3H-imidazol-4-yl)-propenone. MS found for $C_{12}H_{18}N_3OF$ as $(M+H)^+$ 240.28.

A mixture of 3-dimethylamino-2-fluoro-1-(3-isopropyl-2-methyl-3H-imidazol-4-yl)-propenone (550 mg, 2.33 mmol) and guanidine carbonate (884 mg, 4.9 mmol) in 2-methoxyethanol (7 mL) was heated in microwave (Emry's Optimizer) at 160° C. After 30 minutes, the reaction mixture was diluted with water and extracted with DCM. The combined DCM layers were dried (MgSO$_4$). Filtration and concentration gave 5-fluoro-4-(3-isopropyl-2-methyl-3H-imidazol-4-yl)-pyrimidin-2-ylamine, which was used for the next step without purification. MS found for $C_{11}H_{14}N_5F$ as $(M+H)^+$ 236.08.

A mixture of the above amine (235 mg, 1.71 mmol), 5-bromo-thiophene-2-carboxylic acid methyl ester (565 mg, 2.56 mmol), Pd$_2$(dba)$_3$ (31 mg, 0.03 mmol), XantPhos (49 mg, 0.09 mmol) and Cs$_2$CO$_3$ (1.1 g, 3.42 mmol) in dioxane was heated in a pressure vessel at 130° C. After 13 hours, the reaction mixture was diluted with dioxane/THF (1:1, 40 mL) and stirred. The mixture was then filtered through celite pad and washed with DCM/THF. The filtrate was then concentrated and used further without purification. MS found for $C_{17}H_{18}FN_5O_2S$ as $(M+H)^+$ 376.15. To the above crude ester in MeOH/THF (1:1) (10 mL) was added 3N NaOH (4.0 mL) and stirred at 55° C. After 16 hours, the reaction mixture was concentrated, diluted with water and washed with ether (3×). The aqueous phase was then neutralized with 6N HCl (1.5 mL) and the precipitated solid was dried to give 5-[5-fluoro-4-(3-isopropyl-2-methyl-3H-imidazol-4-yl)-pyrimidin-2-ylamino]-thiophene-2-carboxylic acid which was used for the next step without purification. MS found for $C_{16}H_{16}FN_5O_2S$ as $(M+H)^+$ 362.07.

To the above acid (1.0 equiv) in NMP (5 mL), was added HATU (1.5 equiv), (2-amino-4-thiophen-2-yl-phenyl)-carbamic acid tert-butyl ester (1.5 equiv.) and NMM (6.0 equiv). The reaction mixture was then stirred at 50° C. for 48 hours. The reaction mixture was diluted with water and acetonitrile and the resulting solid was filtered, washed with water, and dried to give [2-({5-[5-fluoro-4-(3-isopropyl-2-methyl-3H-imidazol-4-yl)-pyrimidin-2-ylamino]-thiophene-2-carbonyl}-amino)-4-thiophen-2-yl-phenyl]-carbamic acid tert-butyl ester. MS found for $C_{31}H_{32}FN_7O_3S_2$ as $(M+H)^+$ 633.97.

To the above Boc protected compound was added 4.0 M HCl in dioxane and stirred at room temperature for 30 minutes. The reaction mixture was then concentrated and diluted with water and acetonitrile and directly purified by preparative HPLC. Lyophilization followed to give the title compound. MS found for $C_{26}H_{24}N_7FOS_2$ as $(M+H)^+$ 533.93. $^1H$ NMR (400 MHz, dmso-$d_6$): δ 10.98 (s, 1H); 9.47 (s, 1H); 8.63 (d, J=2.8 Hz, 1H); 8.12 (s, 1H); 7.75 (d, J=4.4 Hz, 1H); 7.35-7.17 (m, 6H); 6.99 (m, 1H); 6.71 (m, 2H); 5.42 (m, 1H); 5.04 (brs, 2H); 2.47 (s, 3H); 1.44 (d, J=7.2 Hz, 6H).

Example 18

N-(2-aminophenyl)-2-(4-(1-isopropyl-2-methylimidazol-5-yl)pyrimidin-2-ylamino)thiazole-5-carboxamide Example 18 (Compound 1$^a$-c-2)

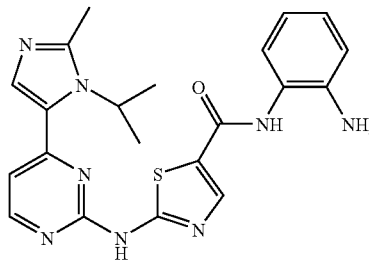

Similar procedure from Example 15 was followed to obtain the title compound using Int-10 and 1,2-phenylenediamine. MS found for $C_{21}H_{22}N_8SO$ as $(M+H)^+$ 434.98. $^1H$ NMR (400 MHz, dmso-$d_6$): δ 12.01 (brs, 1H); 9.53 (s, 1H); 8.56 (d, J=5.2 Hz, 1H); 8.23 (s, 1H); 8.12 (s, 1H); 7.55 (s, 1H); 7.28 (d, J=5.6 Hz, 1H); 7.10 (d, J=8.0 Hz, 1H); 6.94 Hz, 1H); 6.74 (d, J=8.0 Hz, 1H); 6.57 (t, J=6.8 Hz, 1H); 5.84 (m, 1H); 4.88 (brs, 1H); 2.48 (s, 3H); 1.47 (d, J=6.8 Hz, 6H).

Example 19

Biological Assays

HDAC inhibitory activity of the compounds of Examples 1-18 was measured by two types of assays in which HDAC 1 was used as a target molecule. The first assay was carried out without preincubation after addition of the enzyme. The test compound was suspended in and titrated in dimethyl sulfoxide (DMSO). It was then spotted into a 384-well test plate. The enzyme, HDAC 1, was diluted in assay buffer containing 25 mM Tris-HCl (pH 8.0), 137 mM NaCl, 2.7 mM KCl, and 0.01% Tween-20 and added to the pre-spotted compound. The peptide substrate containing a fluorophore/quencher pair was diluted in the same assay buffer and added to the compound/enzyme mix initiating the reaction. The reaction incubated at room temperature for about 45 minutes. A concentrated developer solution was diluted in the assay buffer, and added to the reaction. The reaction was incubated at room temperature for about 15 minutes and relative fluorescence was read on an instrument reader.

The second assay is similar to the first assay described above, except that preincubation is carried out for about 3 hours after the enzyme is introduced. The test compound was suspended in, and titrated in DMSO. It was then spotted into a 384-well test plate. The enzyme, HDAC 1, was diluted in the same assay buffer as used in the previous assay and added to the pre-spotted compound. The enzyme/compound mix was incubated at room temperature for about 3 hours. The peptide substrate containing a fluorophore/quencher pair was diluted in the assay buffer and added to the compound/enzyme mix initiating the reaction. The reaction incubated at room temperature for 45 minutes. A concentrated developer solution was diluted in the assay buffer, and added to the reaction. The reaction was incubated at room temperature for about 15 minutes and relative fluorescence was read on an instrument reader.

The following table shows $IC_{50}$ data for the compound tested with the protocols described above.

TABLE 1

| | $IC_{50}$ of inhibitor compounds | |
|---|---|---|
| Compound | HDAC 1 inhibitory activity ($IC_{50}$ [μM]) (3-hour preincubation) | CDK2 ($IC_{50}$ [μM]) |
| Example 1 | 0.273 | 0.03 |
| Example 2 | 0.241 | 0.01 |
| Example 3 | 0.019 | 0.04 |
| Example 4 | 0.809 | 0.02 |
| Example 5 | 0.423 | >40 |
| Example 6 | >10 | 0.01 |
| Example 7 | 0.03 | >40 |
| Example 8 | 0.656 | 0.002 |
| Example 9 | 0.04 | 0.027 |
| Example 10 | 0.034 | 0.026 |
| Example 11 | 4.37 | 0.012 |
| Example 12 | 0.153 | 0.34 |
| Example 13 | 0.054 | 0.065 |
| Example 14 | 0.028 | 0.99 |
| Example 15 | 0.049 | 1.04 |
| Example 16 | 0.032 | 2.15 |
| Example 17 | 0.037 | 0.025 |
| Example 18 | 0.41 | 2.1 |

The results indicate that the compounds have inhibitory activity against HDAC and/or CDK and thus can be useful to treat or inhibit diseases caused by abnormal activities of HDAC and/or CDK.

All patents and publications cited herein are incorporated by reference into this application in their entirety.

What is claimed is:

1. A compound selected from those of Formula (I) and pharmaceutically acceptable salts thereof:

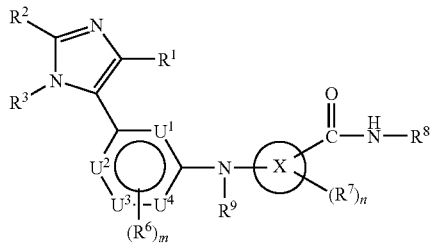

Formula (I)

wherein

R¹, R² and R³ are independently selected from the group consisting of H, halo, nitro, cyano, hydroxy, hydroxy (C$_{1-10}$ alkyl), amino(C$_{1-10}$ alkyl), haloalkyl, haloalkoxy, amino, azido, carboxyl, carbamoyl, mercapto, sulphamoyl, C$_{1-10}$ alkyl, C$_{2-10}$ alkenyl, C$_{2-10}$ alkynyl, C$_{1-10}$ alkoxy, hydroxy(C$_{1-10}$ alkoxy)(C$_{1-10}$ alkoxy), (C$_{1-10}$ alkoxy)(C$_{1-10}$alkoxy), (C$_{1-10}$alkoxy)(C$_{1-10}$alkyl), C$_{1-10}$ alkanoyl, C$_{1-10}$ alkanoyloxy, N—(C$_{1-10}$ alkyl)amino, N,N—(C$_{1-10}$ alkyl)$_2$amino, C$_{1-10}$ alkanoylamino, N—(C$_{1-10}$ alkyl)carbamoyl, N,N—(C$_{1-10}$ alkyl)$_2$carbamoyl, C$_{1-10}$ alkyl-S(O)$_a$ wherein a is 0, 1 or 2, C$_{1-10}$ alkoxycarbonyl, NH$_2$—S(O)$_2$NH—, NH$_2$—CO—NH—, N—(C$_{1-10}$ alkyl)sulphamoyl, N,N—(C$_{1-10}$ alkyl)$_2$sulphamoyl, aryl, arylalkyl, aryloxy, arylthio, cycloalkyl, cycloalkylalkyl, cycloalkyloxy, heterocyclyl, heterocyclylalkyl, heterocyclyl(C═O)—, heterocyclyloxy and heterocyclylthio, wherein each R¹ R² and R³ is optionally substituted by one or more A;

U¹, U², U³ and U⁴ are independently selected from —N—, —CH—, and —CR⁶—, with the proviso that at least one of U¹, U², U³ and U⁴ is —N—;

m is 0, 1, 2, or 3;

R⁶ is halo, hydroxy, nitro, cyano, trifluoromethyl, trifluoromethoxy, amino, carboxyl, carbamoyl, sulphamoyl, C$_{1-10}$ alkyl, C$_{2-10}$ alkenyl, C$_{2-10}$ alkynyl, C$_{1-10}$ alkoxy, C$_{1-10}$ alkanoyl, N—(C$_{1-10}$ alkyl)amino, N,N—(C$_{1-10}$ alkyl)$_2$ amino, C$_{1-10}$ alkanoylamino, N—(C$_{1-10}$ alkyl) carbamoyl, N,N—(C$_{1-10}$ alkyl)$_2$ carbamoyl, C$_{1-10}$ alkyl-S(O)$_a$ wherein a is 0, 1 or 2, NH$_2$—S(O)$_2$NH—, N—(C$_{1-10}$ alkyl)sulphamoyl or N,N—(C$_{1-10}$ alkyl)$_2$sulphamoyl; wherein R⁶ is optionally substituted by one or more B;

X is phenyl, 5-membered heteroaryl, or 6-membered heteroaryl, wherein the heteroaryl contains one or more heteroatoms selected from N, S and O;

R⁷ represents one or more optional non-hydrogen substituents on ring X, wherein when present, each R⁷ is independently selected from hydroxy, halo, nitro, cyano, trifluoromethyl, trifluoromethoxy, amino, carboxyl, carbamoyl, sulphamoyl, C$_{1-10}$ alkyl, C$_{2-10}$ alkenyl, C$_{2-10}$ alkynyl, C$_{1-10}$ alkoxy, C$_{1-10}$ alkanoyl, N—(C$_{1-10}$ alkyl) amino, N,N—(C$_{1-10}$ alkyl)$_2$ amino, C$_{1-10}$ alkanoylamino, N—(C$_{1-10}$ alkyl)carbamoyl, N,N—(C$_{1-10}$ alkyl)$_2$ carbamoyl, C$_{1-10}$ alkyl-S(O)$_a$ wherein a is 0, 1 or 2, NH$_2$—S(O)$_2$NH—, N—(C$_{1-10}$ alkyl)sulphamoyl, N,N—(C$_{1-10}$ alkyl)$_2$sulphamoyl, cycloalkyl, aryl and heterocyclyl;

n is 0, 1, 2, 3 or 4;

R⁸ is hydroxy, aryl or heteroaryl, wherein aryl or heteroaryl is substituted with —NH$_2$ or —OH and aryl or heteroaryl is optionally further substituted with one or more groups selected from amino, halo, alkyl, alkenyl, alkynyl, haloalkyl, cycloalkyl, heterocyclyl, aryl, haloaryl, haloheterocyclyl, wherein alkyl, alkenyl, or alkynyl is optionally further substituted with one or more groups selected from halo, hydroxy, alkyl, haloalkyl and cycloalkyl;

R⁹ is H, alkyl, haloalkyl, aminoalkyl, cycloalkyl, aryl, or heterocyclyl, wherein R⁹ is optionally substituted by one or more D; and A, B and D are independently selected from halo, nitro, cyano, hydroxy, oxo, hydroxyalkyl, haloalkyl, haloalkoxy, amino, azido, carboxyl, carbamoyl, mercapto, sulphamoyl, C$_{1-10}$ alkyl, C$_{2-10}$ alkenyl, C$_{2-10}$ alkynyl, C$_{1-10}$ alkoxy, C$_{1-10}$ alkanoyl, C$_{1-10}$ alkanoyloxy, N—(C$_{1-10}$ alkyl)amino, N,N—(C$_{1-10}$ alkyl)$_2$amino, C$_{1-10}$ alkanoylamino, N—(C$_{1-10}$ alkyl)carbamoyl, N,N—(C$_{1-10}$ alkyl)$_2$carbamoyl, C$_{1-10}$ alkyl-S(O)$_a$ wherein a is 0, 1 or 2, C$_{1-10}$ alkoxycarbonyl, N—(C$_{1-10}$ alkyl)sulphamoyl, N,N—(C$_{1-10}$ alkyl)$_2$sulphamoyl, H$_2$NS(O)$_2$NH—, N—(C$_{1-10}$ alkyl)NHS(O)$_2$NH—, N,N—(C$_{1-10}$ alkyl)$_2$NS(O)$_2$NH—, aryl, aryloxy, arylthio, cycloalkyl, cycloalkyloxy, heterocyclyl, heterocyclyl(C═O)—, heterocyclyloxy and heterocyclylthio.

2. The compound of claim 1, wherein R⁸ is hydroxy, phenyl or 5-membered or 6-membered heteroaryl, wherein phenyl or heteroaryl is substituted with —NH$_2$ or —OH at a ring position adjacent to attachment of the -CONH-moiety, and phenyl or heteroaryl is optionally further substituted with one or more substituents selected from amino, halo, alkyl, alkenyl, alkynyl, haloalkyl, cycloalkyl, heterocyclyl, aryl, haloaryl, haloheterocyclyl, wherein alkyl, alkenyl, or alkynyl is optionally further substituted with one or more groups selected from halo, hydroxy, alkyl, haloalkyl and cycloalkyl.

3. The compound according to claim 1, wherein U¹, U², U³ and U⁴ are selected to form any of the following heteroaryl moieties

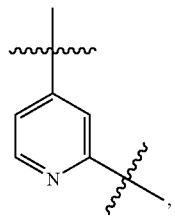 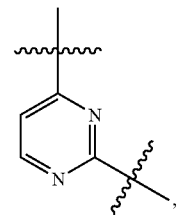

,                    ,

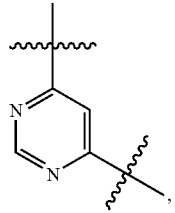 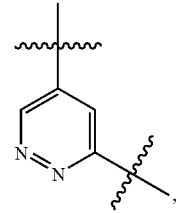

,                    ,

-continued

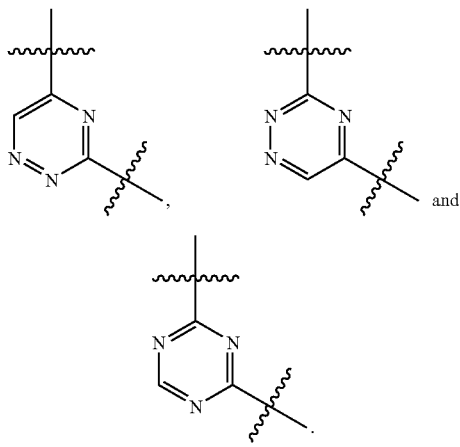

4. The compound of claim 1 selected from those of Formulae (I$^a$), (I$^b$), and (I$^c$) and pharmaceutically acceptable salts thereof:

Formula (I$^a$)

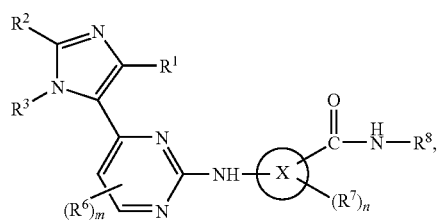

Formula (I$^b$)

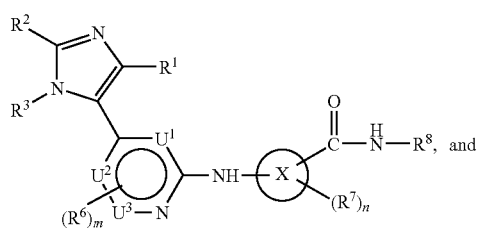

Formula (I$^c$)

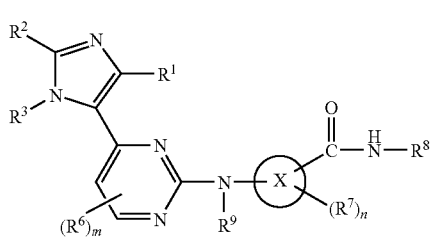

wherein U$^1$, U$^2$ and U$^3$ are selected to be any of (a) U$^1$, U$^2$ and U$^3$ are —CH— or —CR$^6$—; (b) U$^1$ and U$^2$ are —CH— or —CR$^6$— and U$^3$ is —N—; (c) U$^1$ and U$^3$ are —CH— or —CR$^6$— and U$^2$ is —N—; and (d) U$^1$ and U$^2$ are —N— and U$^3$ is —CH— or —CR$^6$—.

5. The compound of claim 4 selected from those of Formulae (I$^a$-a), (I$^a$-b), and (I$^a$-c) and pharmaceutically acceptable salts thereof:

Formula (I$^a$-a)

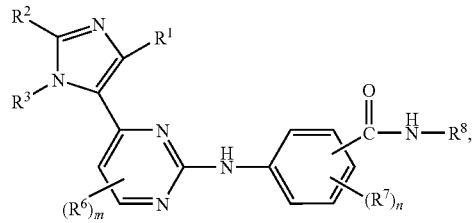

Formula (I$^a$-b)

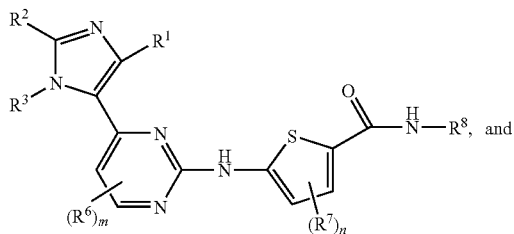

Formula (I$^a$-c)

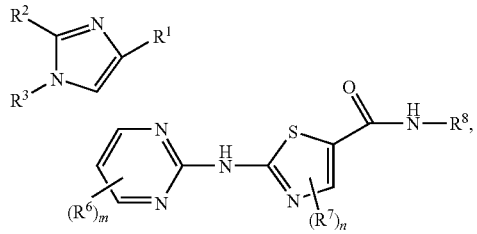

wherein

R$^1$, R$^2$ and R$^3$ are independently selected from the group consisting of H, halo, nitro, cyano, hydroxy, hydroxyalkyl, haloalkyl, haloalkoxy, amino, azido, carboxyl, carbamoyl, mercapto, sulphamoyl, C$_{1-10}$ alkyl, C$_{2-10}$ alkenyl, C$_{2-10}$ alkynyl, C$_{1-10}$ alkoxy, C$_{1-10}$ alkanoyl, C$_{1-10}$ alkanoyloxy, N—(C$_{1-10}$ alkyl)amino, N,N—(C$_{1-10}$ alkyl)$_2$amino, C$_{1-10}$ alkanoylamino, N—(C$_{1-10}$ alkyl)carbamoyl, N,N—(C$_{1-10}$ alkyl)$_2$carbamoyl, C$_{1-10}$ alkyl-S(O)$_a$ wherein a is 0, 1 or 2, C$_{1-10}$ alkoxycarbonyl, NH$_2$—S(O)$_2$NH—, N—(C$_{1-10}$ alkyl)sulphamoyl, N,N—(C$_{1-10}$ alkyl)$_2$sulphamoyl, aryl, aryloxy, arylthio, cycloalkyl, cycloalkyloxy, heterocyclyl, heterocyclyl (C=O)—, heterocycyloxy and heterocyclylthio; wherein each of R$^1$, R$^2$ and R$^3$ is optionally substituted by one or more A.

6. The compound of claim 5, wherein the compound is selected from those of Formulae (I$^a$-a), (I$^a$-b), and (I$^a$-c), and wherein R$^1$, R$^2$ and R$^3$ are independently selected from the group consisting of H, chloro, fluoro, bromo, methyl, ethyl, propyl, isopropyl, methoxy, ethoxy, acetyl, carboxyl, methylcarboxyl, cyano, methoxymethyl, ethoxyethyl, propoxyethyl, methoxyethoxy, trifluoromethyl, hydroxyethoxy, dimethylamino, diethylamino, dimethylaminomethyl, dimethylaminoethyl, diethylaminomethyl, dimethylaminoethoxy, dimethylaminocarbonyl, dimethylaminoethylamide, trifluoromethoxymethyl, trifluoroethoxymethyl, isopropylcarbonyl, 1-hydoxyethyl, 3-oxetanoxy, trifluoroethylaminomethyl, N-methyl-N-methoxyethyl-aminoethyl, cyclopropanylmethyl, cyclobutoxy, 1-cyclopropanylethoxy, cyclopropanylmethylaminomethyl, 4-methylpiperazin-1-carbonyl, isoindolin-2-yl, N-methoxyethylcarbamoyl, N-(morpholin-4-yl)-ethylcarbamoyl, dimethylaminoethylamino, methylcarboxyl, N,N-dimethylaminoethylcarbamoyl, benzyl, phenylethyl, trifluoromethylphenylethyl, phenoxymethyl, fluorophenoxymethyl, phenylethylaminomethyl, benzylaminomethyl, triazinylmethyl, piperidinylmethyl, piperidinyloxy, trifluoromethylpiperidinylmethyl, pyridinyloxymethyl, pyridinylmethoxy, tetrahydropyrazinyloxy, methylpiperazinylmethyl, methanesulfonyl, pyrrolidin-1-yl, pyrrolidin-2-yl, pyrrolidin-3-yl, pyrrolidin-1-ylmethyl, pyrrolidin-2-ylmethyl, pyrrolidin-3-ylmethyl, pyrrolidin-1-ylethoxy, pyrrolidin-2-ylethoxy, pyrrolidin-3-ylethoxy, thiazol-4-yl, 2-methyl-thiazol-4-yl, imidazol-1-ylmethyl, imidazol-2-ylmethyl, imidazol-4-ylmethyl, imidazolidin-1-yl, imidazolidin-2-yl, imidazolidin-4-yl, imidazolidin-1-ylmethyl, imidazolidin-2-ylmethyl, imidazolidin-4-ylmethyl, imidazolin-1-yl, imidazolin-2-yl, imidazolin-4-yl, pyrazolidin-1-yl, pyrazolidin-3-yl, pyrazolidin-4-yl, pyrazolin-1-yl, pyrazolin-3-yl, pyrazolin-4-yl, piperidin-1-yl, piperidin-2-yl, piperidin-3-yl, piperidin-4-yl, piperidin-1-ylmethyl, piperidin-2-ylmethyl, piperidin-3-ylmethyl, piperidin-4-ylmethyl, piperazin-1-yl, piperazin-2-yl, piperazin-3-yl, morpholin-2-yl, morpholin-3-yl, morpholin-4-yl, morpholin-2-ylmethyl, morpholin-3-ylmethyl, morpholin-4-ylmethyl, morpholin-4-ylsulfonyl, morpholin-2-ylethoxy, morpholin-3-ylethoxy and morpholin-4-ylethoxy;

$R^6$, if present, is halo, hydroxy, alkyl or haloalkyl;

m is 0, 1, or 2;

n is 0, 1, or 2;

$R^7$, if present, is independently fluoro, chloro, bromo, or methyl; and $R^8$ is hydroxy, 2-hydroxyphenyl, 2-aminophenyl, 2-amino-6-fluorophenyl, 2-amino-5-fluorophenyl, 2-amino-5-trifluoromethylphenyl, 4-aminobiphenyl-3-yl, 4'-fluoro-4-aminobiphenyl-3-yl, 2-amino-5-(thiophen-2-yl)phenyl, 5'-chloro-2-amino-5-(thiophen-2-yl)phenyl, 5'-methyl-2-amino-5-(thiophen-2-yl) phenyl, 2-amino-5-(thiophen-3-yl)phenyl, 2-aminopyridin-3-yl, 4-amino-1-phenyl-1H-pyrazol-3-yl, 2-amino-5-(3-hydroxy-3-methylbut-1-ynyl)phenyl, 2-amino-5-(4,4,4-trifluoro-3-hydroxy-3-(trifluoromethyl)but-1-ynyl)phenyl, 2-amino-5-(3-cyclopropyl-prop-1-ynyl)phenyl or 2-amino-5-(3-(1-hydroxycyclopropyl)prop-1-ynyl)phenyl.

7. The compound of claim 6 which is selected from the group consisting of:

N-hydroxy-4-(4-(1-isopropyl-2-methylimidazol-5-yl)pyrimidin-2-ylamino)benzamide;

N-(2-aminophenyl)-4-(4-(1-isopropyl-2-methylimidazol-5-yl)pyrimidin-2-ylamino)benzamide;

N-hydroxy-3-(4-(1-isopropyl-2-methylimidazol-5-yl)pyrimidin-2-ylamino)benzamide;

N-(2-aminophenyl)-3-(4-(1-isopropyl-2-methylimidazol-5-yl)pyrimidin-2-ylamino)benzamide;

N-(2-amino-5-(thiophen-2-yl)phenyl)-4-(4-(1-isopropyl-2-methylimidazol-5-yl)pyrimidin-2-ylamino)benzamide;

N-(2-amino-5-fluorophenyl)-4-(4-(1-isopropyl-2-methylimidazol-5-yl)pyrimidin-2-ylamino)benzamide;

N-(2-amino-5-(thiophen-2-yl)phenyl)-3-(4-(1-isopropyl-2-methylimidazol-5-yl)pyrimidin-2-ylamino)benzamide;

N-(2-amino-5-fluorophenyl)-3-(4-(1-isopropyl-2-methylimidazol-5-yl)pyrimidin-2-ylamino)benzamide;

N-(2-amino-5-(trifluoromethyl)phenyl)-4-(4-(1-isopropyl-2-methylimidazol-5-yl)pyrimidin-2-ylamino)benzamide;

N-(4-amino-4'-fluorobiphenyl-3-yl)-4-(4-(1-isopropyl-2-methylimidazol-5-yl)pyrimidin-2-ylamino)benzamide;

N-(4-amino-4'-fluorobiphenyl-3-yl)-2-(4-(1-isopropyl-2-methylimidazol-5-yl)pyrimidin-2-ylamino)thiazole-5-carboxamide;

N-(2-amino-5-(thiophen-2-yl)phenyl)-2-(4-(1-isopropyl-2-methylimidazol-5-yl)pyrimidin-2-ylamino)thiazole-5-carboxamide;

N-(2-aminophenyl)-2-(4-(1-isopropyl-2-methylimidazol-5-yl)pyrimidin-2-ylamino)thiazole-5-carboxamide;

N-(2-aminophenyl)-5-(4-(1-isopropyl-2-methylimidazol-5-yl)pyrimidin-2-ylamino)thiophene-2-carboxamide;

N-hydroxy-5-(4-(1-isopropyl-2-methylimidazol-5-yl)pyrimidin-2-ylamino)thiophene-2-carboxamide;

N-(2-amino-5-(thiophen-2-yl)phenyl)-5-(4-(1-isopropyl-2-methylimidazol-5-yl)pyrimidin-2-ylamino) thiophene-2-carboxamide;

N-(2-amino-5-fluorophenyl)-5-(4-(1-isopropyl-2-methylimidazol-5-yl)pyrimidin-2-ylamino)thiophene-2-carboxamide;

N-(4-amino-4'-fluorobiphenyl-3-yl)-5-(4-(1-isopropyl-2-methylimidazol-5-yl)pyrimidin-2-ylamino)thiophene-2-carboxamide;

N-(4-amino-4'-fluorobiphenyl-3-yl)-5-(4-(1-isopropyl-2-methylimidazol-5-yl)pyrimidin-2-ylamino)-4-methylthiophene-2-carboxamide;

N-(2-amino-5-(thiophen-2-yl)phenyl)-5-(5-fluoro-4-(1-isopropyl-2-methylimidazol-5-yl)pyrimidin-2-ylamino)thiophene-2-carboxamide; and pharmaceutically acceptable salts thereof.

8. The compound of claim 4 selected from those of Formulae ($I^b$-a), ($I^b$-b), ($I^b$-c), and ($I^b$-d) and pharmaceutically acceptable salts thereof:

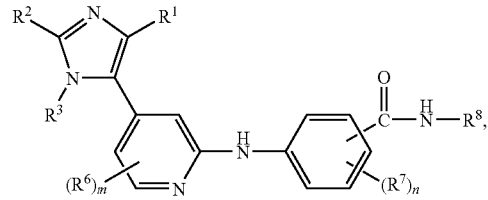

Formula (Ib-a)

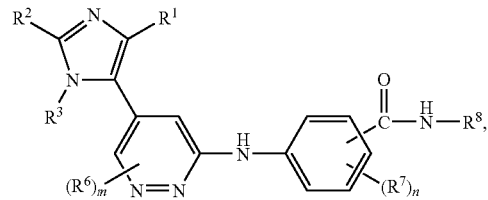

Formula (Ib-b)

-continued

Formula (Ib-c)

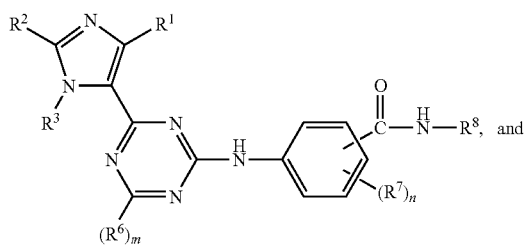

Formula (Ib-d)

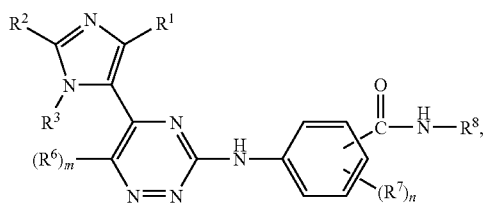

wherein
R¹, R² and R³ are independently selected from the group consisting of H, halo, nitro, cyano, hydroxy, hydroxyalkyl, haloalkyl, haloalkoxy, amino, azido, carboxyl, carbamoyl, mercapto, sulphamoyl, $C_{1-10}$ alkyl, $C_{2-10}$ alkenyl, $C_{2-10}$ alkynyl, $C_{1-10}$ alkoxy, $C_{1-10}$ alkanoyl, $C_{1-10}$ alkanoyloxy, N—($C_{1-10}$ alkyl)amino, N,N—($C_{1-10}$ alkyl)₂amino, $C_{1-10}$ alkanoylamino, N—($C_{1-10}$ alkyl)carbamoyl, N,N—($C_{1-10}$ alkyl)₂carbamoyl, $C_{1-10}$ alkyl-S(O)$_a$ wherein a is 0, 1 or 2, $C_{1-10}$ alkoxycarbonyl, NH₂—S(O)₂NH—, N—($C_{1-10}$ alkyl)sulphamoyl, N,N—($C_{1-10}$ alkyl)₂sulphamoyl, aryl, aryloxy, arylthio, cycloalkyl, cycloalkyloxy, heterocyclyl, heterocyclyl (C═O)—, heterocyclyloxy and heterocyclylthio; wherein each of R¹, R² and R³ is optionally substituted by one or more A.

9. The compound of claim 8 which is selected from the group consisting of:
N-hydroxy-4-(4-(1-isopropyl-2-methylimidazol-5-yl)pyridin-2-ylamino)benzamide;
N-(2-aminophenyl)-4-(4-(1-isopropyl-2-methylimidazol-5-yl)pyridin-2-ylamino)benzamide;
N-(2-amino-5-(thiophen-2-yl)phenyl)-4-(4-(1-isopropyl-2-methylimidazol-5-yl)pyridin-2-ylamino)benzamide;
N-(2-amino-5-fluorophenyl)-4-(4-(1-isopropyl-2-methylimidazol-5-yl)pyridin-2-ylamino)benzamide;
N-hydroxy-4-(5-(1-isopropyl-2-methylimidazol-5-yl)pyridazin-3-ylamino)benzamide;
N-(2-aminophenyl)-4-(5-(1-isopropyl-2-methylimidazol-5-yl)pyridazin-3-ylamino)benzamide;
N-(2-amino-5-(thiophen-2-yl)phenyl)-4-(5-(1-isopropyl-2-methylimidazol-5-yl)pyridazin-3-ylamino)benzamide;
N-(2-amino-5-fluorophenyl)-4-(5-(1-isopropyl-2-methylimidazol-5-yl)pyridazin-3-ylamino)benzamide;
N-hydroxy-4-(4-(1-isopropyl-2-methylimidazol-5-yl)-1,3,5-triazin-2-ylamino)benzamide;
N-(2-aminophenyl)-4-(4-(1-isopropyl-2-methylimidazol-5-yl)-1,3,5-triazin-2-ylamino)benzamide;
N-(2-amino-5-(thiophen-2-yl)phenyl)-4-(4-(1-isopropyl-2-methylimidazol-5-yl)-1,3,5-triazin-2-ylamino)benzamide;
N-(2-amino-5-fluorophenyl)-4-(4-(1-isopropyl-2-methylimidazol-5-yl)-1,3,5-triazin-2-ylamino)benzamide;
N-(2-aminophenyl)-4-(5-(1-isopropyl-2-methylimidazol-5-yl)-1,2,4-triazin-3-ylamino)benzamide;
N-(2-amino-5-(thiophen-2-yl)phenyl)-4-(5-(1-isopropyl-2-methylimidazol-5-yl)-1,2,4-triazin-3-ylamino)benzamide; and
pharmaceutically acceptable salts thereof.

10. The compound of claim 4 selected from those of Formulae (I$^c$-a) and (I$^c$-b) and pharmaceutically acceptable salts thereof:

Formula (I$^c$-a)

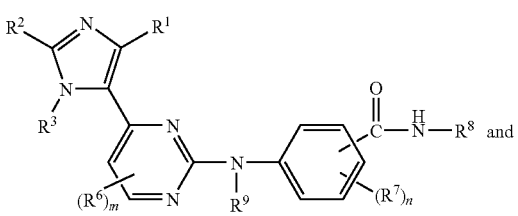

Formula (I$^c$-b)

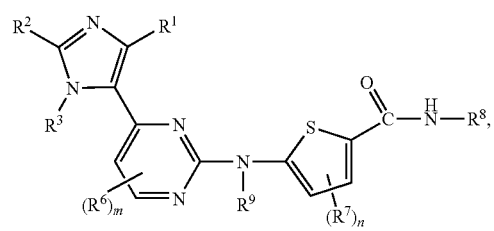

wherein R⁹ is alkyl, haloalkyl or aminoalkyl.

11. The compound of claim 10 which is selected from the group consisting of:
N-(2-aminophenyl)-4-((4-(1-isopropyl-2-methylimidazol-5-yl)pyrimidin-2-yl)(2,2,2-trifluoroethyl)amino)benzamide;
N-hydroxy-4-((4-(1-isopropyl-2-methylimidazol-5-yl)pyrimidin-2-yl)(2,2,2-trifluoroethyl)amino)benzamide;
N-(2-aminophenyl)-4-(ethyl(4-(1-isopropyl-2-methylimidazol-5-yl)pyrimidin-2-yl)amino)benzamide;
4-(ethyl(4-(1-isopropyl-2-methylimidazol-5-yl)pyrimidin-2-yl)amino)-N-hydroxybenzamide;
N-(2-aminophenyl)-4-((4-(1-isopropyl-2-methylimidazol-5-yl)pyrimidin-2-yl)(methyl)amino)benzamide;
N-hydroxy-4-((4-(1-isopropyl-2-methylimidazol-5-yl)pyrimidin-2-yl)(methyl)amino)benzamide; and
pharmaceutically acceptable salts thereof.

12. A pharmaceutical composition comprising an effective amount of one or more compounds according to claim 1 and a pharmaceutically-acceptable carrier.

13. The pharmaceutical composition according to claim 12, further comprising one or more anti-cancer agents selected from the group consisting of cyclophosphamide, dacarbazine, cisplatin, methotrexate, mercaptopurine, thioguanine, fluorouracil, cytarabine, vinblastine, paclitaxel, doxorubicin, bleomycin, mitomycin, prednisone, tamoxifen, flutamide, asparaginase, rituximab, trastuzumab, imatinib, retinoic acid, colony-stimulating factor, amifostine, lenalidomide, HDAC inhibitor, CDK inhibitor, camptothecin and topotecan.

* * * * *